United States Patent [19]

Narr et al.

[11] Patent Number: 4,518,597
[45] Date of Patent: May 21, 1985

[54] SUBSTITUTED BENZOXAZIN-2-ONES AND PHARMACEUTICAL COMPOSITIONS CONTAINING THEM

[75] Inventors: Berthold Narr; Josef Nickl; Erich Müller; Josef Roch; Walter Haarmann; Johannes-Maximilian Weisenberger, all of Biberach, Fed. Rep. of Germany

[73] Assignee: Dr. Karl Thomae GmbH, Biberach an der Riss, Fed. Rep. of Germany

[21] Appl. No.: 617,797

[22] Filed: Jun. 6, 1984

Related U.S. Application Data

[63] Continuation of Ser. No. 489,216, Apr. 27, 1983, abandoned.

[30] Foreign Application Priority Data

May 6, 1982 [DE] Fed. Rep. of Germany ....... 3217012

[51] Int. Cl.³ .................. A61K 31/535; C07D 265/18
[52] U.S. Cl. .................................. 514/228; 544/58.6; 544/54; 544/92; 514/229
[58] Field of Search ................... 544/58.6, 54, 92; 424/246, 248.5, 248.52

[56] References Cited

U.S. PATENT DOCUMENTS 3,526,621  9/1970  Bernardi et al. .................. 544/92
3,542,774  11/1970  Shavel et al. .................... 544/92 X
4,140,789  2/1979  Jaeggi et al. .................. 424/248.55
4,310,527  1/1982  Jaeggi et al. .................... 424/251

Primary Examiner—Richard L. Raymond
Attorney, Agent, or Firm—Hammond & Littell, Weissenberger & Dippert

[57] ABSTRACT

This invention is directed to novel benzoxazin-2-ones of the formula

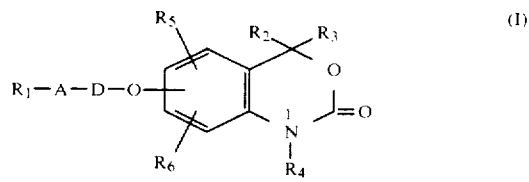

wherein
A is a sulfur atom or an SO, SO$_2$, R—N=S, or R—N=SO$_2$ group where R is a hydrogen atom or an acyl group;
D is an alkylene group;
R$_1$ is an alkyl, phenylalkyl, cycloalkyl, or phenyl group;
R$_4$ is a hydrogen atom or an alkyl group;
R$_5$ is a hydrogen or halogen atom or a nitro or alkyl group; and
R$_6$ is a hydrogen or halogen atom or an alkyl group,
having valuable pharmacological properties, particularly an antithrombotic activity. The compounds of Formula I may be prepared by the methods used for analogous compounds.

13 Claims, No Drawings

SUBSTITUTED BENZOXAZIN-2-ONES AND PHARMACEUTICAL COMPOSITIONS CONTAINING THEM

This application is a continuation of co-pending U.S. patent application Ser. No. 489,216, filed Apr. 27, 1983, abandoned.

FIELD OF THE INVENTION

This invention relates to novel substituted benzoxazin-2-ones. More particularly, this invention relates to substituted benzoxazin-2-ones, methods of preparing these compounds, pharmaceutical compositions containing them as active ingredients, and a method of using them as antithrombotics.

OBJECTS OF THE INVENTION

It is an object of the invention to provide novel substituted benzoxazin-2-ones having useful pharmacodynamic properties.

It is also an object of this invention to provide pharmaceutical compositions containing substituted benzoxazin-2-ones as active ingredients.

It is a further object of the invention to provide a method of using substituted benzoxazin-2-ones as antithrombotics.

These and other objects of the invention will become more apparent from the discussion below.

DETAILED DISCUSSION OF THE INVENTION

The present invention relates to novel substituted benzoxazin-2-ones of the formula

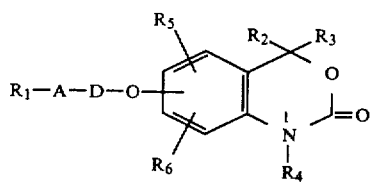

wherein

A is a sulfur atom or an SO, SO₂, R—N=S, or R—N=SO group where R is a hydrogen atom or an acyl group of an organic carboxylic acid, of an organic or inorganic sulfonic acid, or of a carbonic acid derivative;

D is a linear or branched alkylene group having from 2 to 6 carbon atoms;

$R_1$ is an alkyl group having from 1 to 3 carbon atoms, optionally substituted by a phenyl group, or a phenyl group, each phenyl group being optionally substituted by an alkyl group having from 1 to 4 carbon atoms, a halogen atom, an alkoxy group having from 1 to 3 carbon atoms, a hydroxyl group, a cyclohexyl group, a phenyl group, an amino group, or an alkanoylamino group having from 1 to 3 carbon atoms; an alkyl group having from 4 to 8 carbon atoms; a cycloalkyl group having from 3 to 7 carbon atoms; a di-substituted or tri-substituted phenyl group or a mono-substituted or di-substituted hydroxyphenyl or aminophenyl group, the substituents, which may be the same or different, being selected from the group consisting of alkyl groups having from 1 to 4 carbon atoms, alkoxy groups having from 1 to 3 carbon atoms, and halogen atoms; a pyridyl-N-oxide group; or a 5-membered or 6-membered aromatic ring, optionally substituted by one or two alkyl groups each having from 1 to 3 carbon atoms, the aromatic ring containing from 1 to 3 nitrogen atoms or 1 nitrogen atom and 1 sulfur atom, while a phenyl group may optionally be fused onto the aromatic ring via two adjacent carbon atoms;

$R_2$ and $R_3$, which may be identical or different, are each a hydrogen atom, phenyl group, alkyl group having from 1 to 6 carbon atoms, or cycloalkyl group having from 3 to 7 carbon atoms;

$R_4$ is a hydrogen atom or an alkyl group having from 1 to 3 carbon atoms;

$R_5$ is a hydrogen or halogen atom, a nitro group, or an alkyl group having from 1 to 3 carbon atoms; and $R_6$ is a hydrogen or halogen atom or an alkyl group having from 1 to 3 carbon atoms, and to pharmaceutical compositions containing said compounds. The compounds of Formula I have valuable pharmacological properties, particularly an antithrombotic activity.

In a particular embodiment of the invention wherein A, D, and $R_2$ to $R_4$ are as defined above and $R_5$ and $R_6$ are each a hydrogen atom, $R_1$ represents an alkyl group having from 1 to 3 carbon atoms, optionally substituted by a phenyl group; a phenyl group, optionally substituted by an alkyl group having from 1 to 4 carbon atoms, a halogen atom, an alkoxy group having from 1 to 3 carbon atoms, a hydroxy group, a cyclohexyl group, a phenyl group, or an alkanoylamino group having from 1 to 3 carbon atoms; an alkyl group having from 4 to 8 carbon atoms; a cycloalkyl group having from 3 to 7 carbon atoms; a di-substituted or tri-substituted phenyl group or a di-substituted hydroxyphenyl or aminophenyl group, the substituents, which may be the same or different, being selected from the group consisting of alkyl groups having from 1 to 4 carbon atoms, alkoxy groups having from 1 to 3 carbon atoms, and halogen atoms; or a pyridyl group.

The terminology "an acyl group" mentioned in the definition of R is, in particular, the acyl group of an aliphatic saturated or unsaturated alkanoic acid having from 1 to 10 carbon atoms, which may optionally be substituted, or of an optionally substituted aromatic carboxylic acid having from 6 to 12 carbon atoms. Optionally, a —CH=CH— group or one or two —CH— groups may each be replaced by an oxygen, sulfur, or nitrogen atom.

The halogen atoms mentioned in the definition of $R_1$ are, more particularly, fluorine, chlorine, or bromine atoms.

The groups A, D, and $R_1$ to $R_6$ may, for example, have the following meanings:

A may represent a sulfur atom or a sulfoxide, sulfonyl, sulfimino, N-formyl-sulfimino, N-acetyl-sulfimino, N-propionyl-sulfimino, N-pivaloyl-sulfimino, N-pentanoyl-sulfimino, N-hexanoyl-sulfimino, N-heptanoyl-sulfimino, N-octanoyl-sulfimino, N-nonanoyl-sulfimino, N-methoxyacetyl-sulfimino, N-methoxypropionyl-sulfimino, N-benzoyl-sulfimino, N-fluorobenzoyl-sulfimino, N-chlorobenzoyl-sulfimino, N-bromobenzoyl-sulfimino, N-methylbenzoyl-sulfimino, N-ethylbenzoyl-sulfimino, N-isopropylbenzoyl-sulfimino, N-tert.butylbenzoyl-sulfimino, N-difluorobenzoyl-sulfimino, N-dichlorobenzoyl-sulfimino, N-dimethylbenzoyl-sulfimino, N-trimethylbenzoyl-sulfimino, N-naphthoyl-sulfimino, N-pyridinoyl-sulfimino, N-thenoyl-sulfimino, N-acetoxybenzoyl-sulfimino, N-hydroxysulfonyl-sulfimino, N-methanesulfonyl-sulfimino, N-ethanesulfonyl-sulfimino, N-phenylsulfonyl-sulfimino, N-methyl-phenylsulfonyl-sulfimino, N-fluorophenylsulfonyl-sulfimino, N-chlorophenylsulfonyl-sulimino, N-bromophenylsulfonyl-sulfimino, N-pentamethyl-phenylsulfonyl-sulfimino, N-naphthylsulfonyl-sulfimino, N-methoxycarbonyl-sulfimino, N-ethoxycarbonyl-sulfimino, N-propoxycarbonyl-sulfimino, N-isopropoxycarbonyl-sulfimino, N-benzyloxycarbonyl-sulfimino, N-aminocarbonyl-sulfimino, N-methylaminocarbonyl-sulfimino, N-dimethylaminocarbonyl-sulfimino, sulfoximino, N-formyl-sulfoximino, N-acetyl-sulfoximino, N-propionyl-sulfoximino, N-pivaloyl-sulfoximino, N-pentanoyl-sulfoximino, N-hexanoyl-sulfoximino, N-heptanoyl-sulfoximino, N-nonanoyl-sulfoximino, N-methoxyacetyl-sulfoximino, N-methoxypropionyl-sulfoximino, N-benzoyl-sulfoximino, N-fluorobenzoyl-sulfoximino, N-chlorobenzoyl-sulfoximino, N-bromobenzoyl-sulfoximino, N-methylbenzoyl-sulfoximino, N-ethylbenzoyl-sulfoximino, N-isopropylbenzoyl-sulfoximino, N-tert.butylbenzoyl-sulfoximino, N-difluorobenzoyl-sulfoximino, N-dichlorobenzoyl-sulfoximino, N-dimethylbenzoyl-sulfoximino, N-trimethylbenzoyl-sulfoximino, N-naphthoyl-sulfoximino, N-pyridinoyl-sulfoximino, N-thenoyl-sulfoximino, N-acetoxybenzoyl-sulfoximino, N-hydroxy-sulfoximino, N-methanesulfonyl-sulfoximino, N-ethanesulfonyl-sulfoximino, N-phenylsulfonyl-sulfonyl-sulfoximino, N-methylphenylsulfonyl-sulfoximino, N-fluorophenylsulfonyl-sulfoximino, N-chlorophenylsulfonyl-sulfoximino, N-bromophenylsulfonyl-sulfoximino, N-pentamethylphenyl-sulfoximino, N-naphthylsulfonyl-sulfoximino, N-methoxycarbonyl-sulfoximino, N-ethoxycarbonyl-sulfoximino, N-propoxycarbonyl-sulfoximino, N-isopropoxycarbonyl-sulfoximino, N-benzyloxycarbonyl-sulfoximino, N-aminocarbonyl-sulfoximino, N-methylaminocarbonyl-sulfoximino, or N-dimethylaminocarbonyl-sulfoximino group;

D may represent an ethylene, n-propylene, n-butylene, n-pentylene, n-hexylene, 1-methyl-ethylene, 2-methyl-ethylene, 1-methyl-n-propylene, 2-methyl-n-propylene, 3-methyl-n-propylene, 1-methyl-n-butylene, 2-methyl-n-butylene, 3-methyl-n-butylene, 4-methyl-n-butylene, 1-methyl-n-pentylene, 2-methyl-n-pentylene, 3-methyl-n-pentylene, 4-methyl-n-pentylene, 5-methyl-n-pentylene, 1,1-dimethyl-ethylene, 1,2-dimethyl-ethylene, 2,2-dimethyl-ethylene, 1,1-dimethyl-n-propylene, 2,2-dimethyl-n-propylene, 3,3-dimethyl-n-propylene, 1,2-dimethyl-n-propylene, 1,3-dimethyl-n-propylene, 1,1-dimethyl-n-butylene, 2,2-dimethyl-n-butylene, 3,3-dimethyl-n-butylene, 4,4-dimethyl-n-butylene, 1,2-dimethyl-n-butylene, 1,3-dimethyl-n-butylene, 1,4-dimethyl-n-butylene, 2,3-dimethyl-n-butylene, 1-ethyl-ethylene, 2-ethyl-ethylene, 1-ethyl-n-propylene, 2-ethyl-n-propylene, 3-ethyl-n-propylene, 1-ethyl-n-butylene, 2-ethyl-n-butylene, 3-ethyl-n-butylene, 4-ethyl-n-butylene, 1-methyl-2-ethyl-ethylene, 1-methyl-2-ethyl-n-propylene, 1-methyl-3-ethyl-n-propylene, 1-methyl-2-propyl-ethylene, 1-propyl-ethylene, 1-butyl-ethylene, or 1-propyl-n-propylene group;

$R_1$ may represent a methyl, ethyl, n-propyl, isopropyl, n-butyl, 1-methyl-propyl, 2-methyl-propyl, tert.-butyl, n-pentyl, 1-methyl-n-butyl, 2-methyl-n-butyl, 3-methyl-n-butyl, 1-ethyl-n-propyl, tert.-pentyl, n-hexyl, n-heptyl, n-octyl, benzyl, 1-phenylethyl, 2-phenylethyl, 1-phenylpropyl, 3-phenylpropyl, fluorobenzyl, chlorobenzyl, bromobenzyl, methylbenzyl, isopropylbenzyl, methoxybenzyl, ethoxybenzyl, cyclopropyl, cyclobutyl, cyclopentyl, cyclohexyl, cycloheptyl, phenyl, fluorophenyl, chlorophenyl, bromophenyl, methylphenyl, isopropylphenyl, tert.butylphenyl, hydroxyphenyl, methoxyphenyl, ethoxyphenyl, n-propoxyphenyl, formylaminophenyl, acetylaminophenyl, propionylaminophenyl, cyclohexylphenyl, biphenylyl, difluorophenyl, dichlorophenyl, dibromophenyl, dimethoxyphenyl, methoxy-chlorophenyl, methoxy-bromophenyl, dimethyphenyl, methyl-ethylphenyl, diethylphenyl, methyl-tert.butylphenyl, methyl-chlorophenyl, methyl-bromophenyl, tert.butyl-bromophenyl, trimethylphenyl, dichloroaminophenyl, dibromo-aminophenyl, dimethyl-aminophenyl, dichloro-hydroxyphenyl, dibromo-hydroxyphenyl, dimethyl-hydroxyphenyl, di-tert.butyl-hydroxyphenyl, trimethoxyphenyl, pyridyl, pyridyl-N-oxide, methyl-pyridyl, ethyl-pyridyl, dimethyl-pyridyl, pyrimidinyl, methyl-pyrimidinyl, ethyl-pyrimidinyl, propyl-pyrimidinyl, dimethyl-pyrimidinyl, diethyl-pyrimidinyl, pyrazinyl, pyridazinyl, pyrazolyl, imidazolyl, triazolyl, indolyl, indazolyl, quinolyl, isoquinolyl, quinazolinyl, benzimidazolyl, or benzothiazolyl group;

$R_2$ and $R_3$, which may be the same or different, may each represent a hydrogen atom or a methyl, ethyl, n-propyl, isopropyl, n-butyl, 1-methyl-n-propyl, 2-methyl-n-propyl, tert.butyl, n-pentyl, 1-methyl-n-butyl, 2-methyl-n-butyl, 3-methyl-n-butyl, 1-ethyl-n-propyl, tert.pentyl, n-hexyl, phenyl, cyclopropyl, cyclobutyl, cyclopentyl, cyclohexyl, or cycloheptyl group;

$R_4$ may represent a hydrogen atom or a methyl, ethyl, n-propyl, or isopropyl group;

$R_5$ may represent a hydrogen, fluorine, chlorine, bromine, or iodine atom or a nitro, methyl, ethyl, n-propyl, or isopropyl group; and $R_6$ may represent a hydrogen, fluorine, chlorine, or bromine atom or a methyl, ethyl, n-propyl, or isopropyl group.

Preferred compounds of Formula I are those wherein
A is a sulfur atom or an SO, $SO_2$, R—N=S, or R—N=SO group where R is a hydrogen atom or a benzoyl or phenylsulfonyl group, optionally substituted by a methyl group, or an acetyl or propionyl group;

D is a linear alkylene group having from 2 to 6 carbon atoms;

$R_1$ is an alkyl group having from 1 to 8 carbon atoms; a cyclohexyl, benzyl, pyridyl, pyridyl-N-oxide, 2-benzothiazolyl, or 1,2,4-triazol-3-yl group; a 2-pyrimidinyl group optionally substituted by one or two methyl groups; a phenyl group optionally substituted by an alkyl group having from 1 to 4 carbon atoms, by a hydroxyl, methoxy, cyclohexyl, phenyl, or acetylamino group, or by a fluorine, chlorine, or bromine atom; a phenyl group di-substituted by chlorine or bromine atoms or by methyl or methoxy groups, where the substituents of the phenyl nucleus may be identical or different; or an aminophenyl or hydroxyphenyl group substituted by two alkyl groups, each having from 1 to 4 carbon atoms, or by two chlorine or bromine atoms;

$R_2$ and $R_3$, which may be the same or different, are each a hydrogen atom, an alkyl group having from 1 to 6 carbon atoms, or a phenyl or cyclohexyl group;

$R_4$ is a hydrogen atom or a methyl group;

$R_5$ is a hydrogen, fluorine, chlorine, or bromine atom or a nitro, methyl, or ethyl group; and $R_6$ is a hydrogen, chlorine, or bromine atom or a methyl or ethyl group, especially the compounds where the group —O—D—A—$R_1$ is in the 6-position.

Particularly preferred compounds are the compounds of the formula

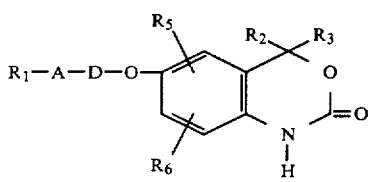

(Ia)

wherein

A is an SO, $SO_2$, H—N=SO, $CH_3CO$—N=SO, or $CH_3$—$C_6H_4SO_2N$=SO group;

D is an n-butylene group;

$R_1$ is a phenyl group optionally substituted by a fluorine, chlorine, or bromine atom or a methyl, hydroxyl, methoxy, cyclohexyl, phenyl, or acetamino group; a phenyl group di-substituted by chlorine or bromine atoms or methyl or methoxy groups, the substituents of the phenyl nucleus being the same or different; or a 4-amino-3,5-dibromophenyl, 3,5-di-tert.butyl-4-hydroxyphenyl, or pyridyl group;

$R_2$ and $R_3$, which may be the same or different, each are a hydrogen atom or a methyl group;

$R_5$ is a hydrogen, chlorine, or bromine atom or a nitro or methyl group; and $R_6$ is a hydrogen, chlorine, or bromine atom or a methyl group.

Another aspect of the invention relates to processes for the preparation of substituted benzoxazin-2-ones of Formula I. These compounds can be prepared as follows:

Method A

A hydroxy compound of the formula

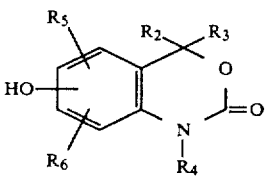

(II)

wherein $R_2$ to $R_6$ are as defined above, or a salt thereof with an inorganic or tertiary organic base, is reacted with a compound of the formula

Z—D—A—$R_1$ (III)

wherein A, D, and $R_1$ are as defined above and Z represents a nucleophilically exchangeable group such as a halogen atom or a sulfonic acid ester group, for example, a chlorine, bromine or iodine atom or a p-toluenesulfonyloxy or methanesulfonyloxy group.

The reaction is conveniently carried out in a suitable solvent or mixture of solvents such as methanol, ethanol, dioxane, tetrahydrofuran, chloroform, or toluene, but preferably in an anhydrous aprotic solvent such as acetone, dimethylformamide, or dimethylsulfoxide, optionally in the presence of an alkali metal base or an alcoholate such as sodium carbonate, potassium carbonate, sodium hydroxide, or sodium ethoxide, at temperatures of between 0° C. and the boiling temperature of the solvent used, for example, at temperatures from about 0° to 100° C., preferably at temperatures of from about 10° to 80° C. However, the reaction may also be performed without a solvent.

Method B

To prepare compounds of Formula I wherein A is an SO, $SO_2$, or R—N=SO group, a compound of the formula

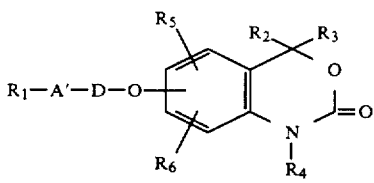

(IV)

wherein $R_1$ to $R_6$ and D are as defined above and A' is a sulfur atom or an SO or R—N=S group where R is as defined above, is oxidized.

Oxidation is preferably carried out in a solvent or mixture of solvents, for example, in water, water/pyridine, ethanol, methanol, acetone, glacial acetic acid, formic acid, dilute sulfuric acid, or trifluoroacetic acid, preferably at temperature of from about −80° to 100° C., dependent upon the oxidation agent used.

To prepare compounds of Formula I wherein A represents an SO or R—N=SO group, oxidation is conveniently carried out with one equivalent of the oxidation agent used, for example, with hydrogen peroxide in glacial acetic acid or formic acid at from about 0° to 20° C. or in acetone at from about 0° to 60° C., with a peracid such as performic acid or m-chloro-perbenzoic acid in glacial acetic acid or trifluoroacetic acid at from about 0° to 20° C., with sodium metaperiodate in aqueous methanol or ethanol at from about 15° to 25° C., with N-bromosuccinimide in ethanal at from about 10° to 50° C., with tert.butylhypochlorite in methanol at from −80° to −30° C., with iodobenzene dichloride in aqueous pyridine at from about 0° to 20° C., with chromic acid in glacial acetic acid or in acetone at from about 0° to 20° C., or with sulfuryl chloride in methylene chloride at −70° C. The thioether-chlorine complex thus obtained is conveniently hydrolyzed with aqueous ethanol.

Moreover, to prepare compounds of Formula I wherein A represents an $SO_2$ group, oxidation is conveniently carried out with one or with two or more equivalents of the oxidation agent used, for example, with hydrogen peroxide in glacial acetic acid or in formic acid at from about 20° to 100° C. or in acetone at from about 0° to 60° C., with a peracid such as performic acid or m-chloroperbenzoic acid in glacial acetic acid, trifluoroacetic acid, or chloroform at temperatures of from about 0° to 50° C., with nitric acid in glacial acetic acid at from about 0° to 20° C., or with chromic acid or potassium permanganate in glacial acetic acid, water/sulfuric acid, or acetone at from about 0° to 20° C. Thus, if A represents a sulfur atom in a compound of Formula IV, the reaction is preferably carried out with two or more equivalents of the appropriate oxidation agent and, correspondingly, with at least one equivalent if A represents the SO group.

Method C

To prepare compounds of Formula I wherein A represents a sulfur atom or an SO₂ group, a compound of the formula

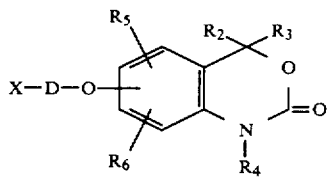

(V)

wherein D and $R_2$ to $R_6$ are as defined above and X represents a nucleophilically exchangeable group such as a halogen atom or a sulfonic acid ester group, for example, a chlorine, bromine, or iodine atom or a p-toluenesulfonyloxy or methanesulfonyloxy group, is reacted with a compound of the formula

Y—R₁  (VI)

wherein $R_1$ as defined above and Y represents an MeSO₂ group, wherein Me represents an alkali metal or alkaline earth/₂ metal atom such as a sodium, potassium, or calcium/₂ atom, or a mercapto group.

The reaction is conveniently carried out in a suitable solvent or mixture of solvents such as dioxane, tetrahydrofuran, chloroform, or toluene, preferably in an anhydrous aprotic solvent such as acetone, dimethylformamide, or dimethylsulfoxide, optionally in the presence of an alkali metal base such as sodium carbonate, potassium carbonate, or sodium hydroxide, at temperatures of between 0° C. and the boiling temperature of the solvent used, for example, at temperatures of from about 0° to 100° C., preferably at temperatures of from about 10° to 50° C. The reaction may, however, also be carried out with a solvent.

Method D

To prepare compounds of Formula I wherein A represents an H—N=SO group, a sulfoxide of the formula

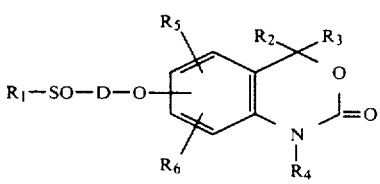

(VII)

wherein D and $R_1$ to $R_6$ are as defined above, is reacted with hydrazoic acid optionally formed in the reaction mixture. The reaction is conveniently carried out in a solvent or mixture of solvents such as methylene chloride, dimethylformamide, or tetrahydrofuran at temperatures of from about 0° to 40° C., preferably at temperatures of from 10° to 35° C. It is particularly advantageous to carry out the reaction with an alkali metal azide, for example, sodium azide, and polyphosphoric acid as the solvent.

Method E

To prepare compounds of Formula I wherein A represents an H—N=SO group, a sulfoxide of the formula

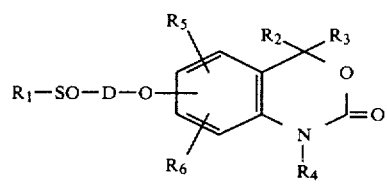

(VII)

wherein D and $R_1$ to $R_6$ are as defined above, is reacted with a compound of the formula

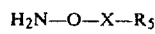

H₂N—O—X—R₅  (VIII)

wherein X represents a carbonyl or sulfonyl group and $R_5$ represents an aryl group di-substituted in the o-positions, such as a 2,4,6-trimethylphenyl or 2,4,6-triisopropylphenyl group.

The reaction is conveniently carried out in a solvent or mixture of solvents such as methylene chloride, chloroform, dimethylformamide, tetrahydrofuran, or dioxane at temperatures of from about 0° to 50° C., preferably at temperatures of from about 5° to 40° C., optionally in the presence of a catalytic amount of an acid such as p-toluenesulfonic acid. However, it is particularly advantageous to carry out the reaction by use of a compound of Formula VIII without isolation of it beforehand or by preparation of such a compound in the reaction mixture.

Method F

To prepare a compound of Formula I wherein R does not represent a hydrogen atom, a compound of the formula

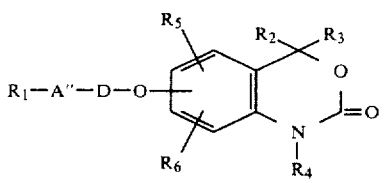

(IX)

wherein D and $R_1$ to $R_6$ are as defined above and A" represents an H—N=S or H—N=SO group, is acylated. The reaction is conveniently carried out in a solvent or mixture of solvents such as water, methylene chloride, chloroform, ether, tetrahydrofuran, dioxane, or dimethylformamide with a corresponding acylation agent, for example, with an acid in the presence of an acid-activating or dehydrating agent such as thionyl chloride, with the anhydrides thereof such as acetic anhydride, with the esters thereof such as ethyl p-toluenesulfonate or diethyl carbonate, with the halides thereof such as acetyl chloride, ethyl chloroformate, or p-toluenesulfonic acid chloride, or with a corresponding isocyanate, all of which may optionally also be used as solvents, optionally in the presence of an inorganic or tertiary organic base such as sodium hydroxide, potassium carbonate, triethylamine, or pyridine, the latter possibly serving simultaneously as solvents, at temperatures of from about −25° to 100° C., preferably at temperatures of from about −10° to 80° C.

Method G

To prepare a compound of Formula I wherein A represents an R—N═S group, a thioether of the formula

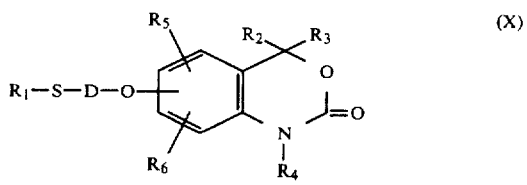

wherein $R_1$ to $R_6$ and D are as defined above, is reacted (1) with a haloamide of the formula

wherein

R' has the meanings given for R above with the exception of a hydrogen atom and

Hal represents a chlorine or bromine atom, or (2) with an alkali metal salt thereof, optionally with subsequent hydrolysis. The reaction is preferably carried out with an alkali metal salt of a compound of Formula XI, for example, the sodium salt, optionally in the presence of an inorganic base such as an alkali metal base in a solvent or mixture of solvents such as methanol, methanol/water, or ethanol, suitably at temperatures of from about 0° to 80° C., preferably at temperatures of from about 5° to 50° C.

The optional subsequent hydrolysis is carried out in the presence of an acid or base, preferably in the presence of a base such as sodium hydroxide, in a solvent or mixture of solvents such as water, methanol, methanol/water, or tetrahydrofuran/water at temperatures up to the boiling temperature of the solvent used.

Method H

To prepare a compound of Formula I wherein A represents an H—N═S or H—N═SO group, an acyl group is hydrolytically cleaved from a compound of the formula

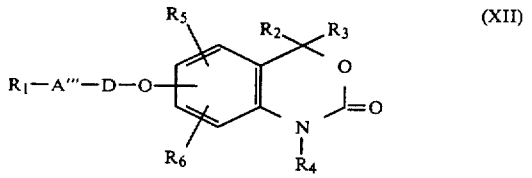

wherein D and $R_1$ to $R_6$ are as defined above and A''' represents an H—N═S or H—N═SO group substituted by a hydrolytically removable acyl group. The acyl group may be, for example, that of a carboxylic acid or of a carbonic acid derivative, such as the acetyl, propionyl, butanoyl, benzoyl, pinanoyl, nicotinoyl, ethoxycarbonyl, aminocarbonyl, or dimethylaminocarbonyl group.

The reaction is carried out in the presence of an acid or base, for example, in the presence of hydrochloric acid, sulfuric acid, sodium hydroxide solution, potassium hydroxide solution, or potassium carbonate, in a solvent or mixture of solvents such as water, methanol, water/methanol, water/ethanol, or water/tetrahydrofuran at temperatures up to the boiling point of the solvent used, for example, at temperatures of from about 50° to 90° C.

Method I

To prepare a compound of Formula I wherein R does not represent a hydrogen atom, a compound of the formula

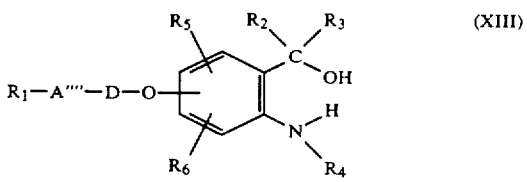

wherein D and $R_1$ to $R_6$ are as defined above and A'''' represents a sulfur atom or an SO, $SO_2$, R'—N═S, or R'—N═SO group, where R' has the meanings given for R above with the exception of a hydrogen atom, is reacted with a carbonic acid derivative of the formula

$$X-CO-X \qquad (XIV)$$

wherein X, which may represent identical or different groups, represents a nucleophilically exchangeable group such as a chlorine atom or a methoxy, ethoxy, benzyloxy, or imidazolyl group. The reaction is conveniently carried out in an inert solvent such as ether, chloroform, dioxane, toluene, or tetrahydrofuran/toluene at temperatures of from about 0° to 80° C., preferably at ambient temperature.

If, according to the invention, a compound of Formula I is obtained wherein $R_4$ represents a hydrogen atom, this compound may be converted by alkylation into a corresponding compound of Formula I wherein $R_4$ represents an alkyl group having from 1 to 3 carbon atoms. The subsequent alkylation is conveniently carried out with an alkyl halide such as methyl iodide or propyl bromide or a sulfonic acid ester such as dimethylsulfate, preferably in the presence of a base such as sodium hydroxide or pyridine, optionally in the presence of a reaction accelerator such as tetrabutylammonium hydrogen sulfate, and preferably in a solvent such as methanol, ethanol, water, sodium hydroxide solution, tetrahydrofuran, or dioxane at temperatures of from about 0° to 80° C., preferably at ambient temperature.

The compounds of Formulas II to XIV used as starting materials are known from the literature or may be obtained by conventional methods (see Examples A to O).

Thus, for example, a hydroxy compound of Formula II may be obtained by reaction of a corresponding carbonyl compound with a corresponding Grignard compound, with subsequent reaction with phosgene and splitting off of the group used as a protecting group for the hydroxyl group, and a compound of Formula V may be obtained by subsequent reaction of a hydroxy- 4H-3,1-benzoxazin-2-one thus obtained with a corresponding compound, for example, with a corresponding monohalogen or dihalogen compound. Moreover, a compound of Formula V may also be obtained by conversion of the hydroxyl group of a corresponding compound into a nucleophilically exchangeable group, for example, by means of thionyl chloride or methanesulfonyl chloride.

A compound of Formula III may be obtained by reaction of a corresponding α,ω-disubstituted alkane with a corresponding mercapto compound, with optional subsequent oxidation.

A compound of Formula IV, VII, or XII used as a starting material may be obtained by reaction of a corresponding hydroxy compound of Formula II with a corresponding compound. A compound thus obtained may subsequently be converted by oxidation into a compound of Formula IX or XII.

A compound of Formula VIII used as starting material may be obtained, for example, by reaction of a corresponding O-carbonyl-acethydroxamic acid ester or O-sulfonyl-acethydroxamic acid ester with sulfuric acid and subsequent extraction after the addition of a base.

A compound of Formula X used as starting material may be obtained, for example, by reaction of a corresponding hydroxyl or mercapto compound with a corresponding halide in the presence of a base.

A compound of Formula XI used as starting material may be obtained by reaction of a corresponding amide with a hypohalite, optionally in the presence of a base.

A compound of Formula XIII used as starting material may be obtained by reaction of a corresponding anthranilic acid ester with a corresponding Grignard compound.

Furthermore, a starting compound of Formula II thus obtained may subsequently be converted into the corresponding halogen compound by chlorination or bromination, for example, by use of chlorine, sulfuryl chloride, or bromine, or into the corresponding nitro compound by use of nitric acid.

The compounds of Formula I wherein A represents a sulfur atom or an R—N=S group are valuable intermediate products for the preparation of compounds of Formula I wherein A represents an SO, $SO_2$, or R—N=SO group.

Moreover, as already mentioned at the beginning, the novel compounds of Formula I have useful pharmacological properties, particularly as antithrombotic activity in warm-blooded animals. They increase the synthesis of aggregation-inhibiting prostaglandins in the walls of blood vessels. The compounds of Formula I also have an inhibiting effect on tumor metastasis. This is based upon the following properties of the compounds of the invention:

1. They are platelet phosphodiesterase inhibitors, which are known to be inhibitors of tumor metastasis [H. Gastpar, Thrombosis Research 5, 277–289 (1974), and K. V. Honn, Science 212, 1270–1272 (1981)].

2. The compounds inhibit primary hemostasis, even at very low doses. They prevent the aggregation of thrombocytes at an injured blood vessel and the formation of a pure clump of platelets, thus extending bleeding time considerably. With the compounds of Formula I this cannot be explained by a limitation of platelet function alone but must be due to an increased release of platelet-active PG by the endothelial cells of the blood vessel. This is confirmed by the fact that the prolongation of bleeding time does not occur if the synthesis of prostacyclin in the endothelial cells is prevented by prior administration of cyclooxygenase inhibitors. Thus, the compounds of the invention constitute a hitherto unknown optimum combination of two basic effects, namely, an increased synthesis of thrombocyte-active, c.AmP-increasing PG's by the wall of the blood vessel and inhibition of the degradation of the increased cAmP by PDE inhibition in the thrombocytes. According to HONN [K. V. Honn, Science, 212, 1270–1272 (1981)] the increase in prostaglandin-($I_2$) activity or synthesis in the wall of the blood vessel thus observed is also a cause of the inhibition of tumor metastasis.

The above pharmacological properties of the compounds of the present invention were ascertained by the standard test methods described below, and the results of these tests for a few representative species of the genus are shown in the tables, where A = 6-[4-(4-chloro-phenylsulfinyl)-butoxyl]-4,4-dimethyl-4H-3,1-benzoxazin-2-one,
B = 6-[4-(4-hydroxy-phenylsulfoximino)-butoxy]-4,4-dimethyl-4H-3,1-benzoxazin-2-one,
C = 6-[4-(4-methoxy-phenylsulfoximino)-butoxy]-4,4-dimethyl-4H-3,1-benzoxazin-2-one,
D = 6-[4-(4-methyl-phenylsulfinyl)-butoxy]-4,4-dimethyl-4H-3,1-benzoxazin-2-one,
E = 6-[4-(4-cyclohexyl-phenylsulfinyl)-butoxy]-4,4-dimethyl-4H-3,1-benzoxazin-2-one,
F = 6-[4-(3,4-dichloro-phenylsulfoximino)-butoxy]-4,4-dimethyl-4H-3,1-benzoxazin-2-one,
G = 6-[3-methoxy-phenylsulfoximino)-butoxy]-4,4-dimethyl-4H-3,1-benzoxazin-2-one,
H = 6-[4-(4-fluoro-phenylsulfoximino)-butoxy]-4,4-dimethyl-4H-3,1-benzoxazin-2-one,
I = 6-[4-(4-bromo-phenylsulfoximino)-butoxy]-4,4-dimethyl-4H-3,1-benzoxazin-2-one,
K = 6-(4-phenylsulfinyl-butoxy)-4H-3,1-benzoxazin-2-one,
L = 6-[4-(4-bromo-phenylsulfinyl)-butoxy]-4,4-dimethyl-4H-3,1-benzoxazin-2-one,
M = 6-[4-(4-bromo-3-methyl-phenylsulfoximino)-butoxy]-4,4-dimethyl-4H-3,1-benzoxazin-2-one,
N = 6-[4-(4-methyl-phenylsulfoximino)-butoxy]-4,4-dimethyl-4H-3,1-benzoxazin-2-one,
O = 6-[4-(3,4-dimethoxy-phenylsulfoximino)-butoxy]-4,4-dimethyl-4H-3,1-benzoxazin-2-one,
P = 6-[4-(4-amino-3,5-dibromo-phenylsulfinyl)-butoxy]-4,4-dimethyl-4H-3,1-benzoxazin-2-one,
Q = 6-[4-(4-biphenylyl-sulfoximino)-butoxy]-4,4-dimethyl-4H-3,1-benzoxazin-2-one,
R = 6-[4-(3,4-dimethoxy-N-acetyl-phenylsulfoximino)-butoxy]-4,4-dimethyl-4H-3,1-benzoxazin-2-one,
S = 6-[4-(3,5-di-tert.butyl-4-hydroxy-N-acetyl-phenylsulfoximino)-butoxy]-4,4-dimethyl-4H-3,1-benzoxazin-2-one,
T = 7-bromo-4,4-dimethyl-6-[4-(4-methyl-phenylsulfoximino)-butoxy]-4H-3,1-benzoxazin-2-one,
U = 7-chloro-4,4-dimethyl-6-[4-(4-methyl-phenylsulfinyl)-butoxy]-4H-3,1-benzoxazin-2-one, and
V = 7-bromo-6-[4-(3,4-dichloro-phenylsulfinyl)-butoxy]-4,4-dimethyl-4H-3,1-benzoxazin-2-one.

1. PDE Inhibition

Principle cAMP is hydrolyzed to AMP by phosphodiesterase (PDE) from various sources, including blood platelets. PDE-inhibitors inhibit this hydrolysis, the PDE-inhibition being dependent upon the concentration.

Method

The phosphodiesterase used was prepared by centrifugal extraction at 10,000 g from human blood platelets which were frozen in water and then thawed.

A quantity of 0.3 ml of a mixture containing 0.1 mol/liter of trihydroxy-aminomethane (pH 7.4), 3 mmols/liter of magnesium chloride, 1 mmol/liter of AMP, 1 μmol/liter of $^3$H-cAMP (specific activity about 10 MBq/μmol), PDE, and the inhibitor under investigation (water in the case of the control) was incubated for 15 minutes at 37° C. The incubation was stopped by the addition of 0.5 ml of zinc sulfate (0.266 mol/liter) and 0.5 ml of barium hydroxide (0.226 mol/liter), the precipitate was centrifuged, and the activity remaining in the unreacted $^3$H-cAMP in the supernatant was determined. From a comparison of the results for inhibitor and control cases, the concentration of the respective inhibitor necessary for a 50% inhibiting effect ($IC_{50}$) was calculated.

Results

The results are set forth in the following table:

TABLE I

| Compound | $IC_{50}$ (μmol/l) |
|---|---|
| A | 0.24 |
| B | 0.23 |
| C | 0.13 |
| D | 0.21 |
| E | 0.078 |
| F | 0.042 |
| G | 0.077 |
| H | 0.18 |
| I | 0.11 |
| K | 1.5 |
| L | 0.24 |
| M | 0.066 |
| N | 0.065 |
| O | 0.20 |
| P | 0.056 |
| Q | 0.0068 |
| R | 0.71 |
| S | 0.077 |
| T | 0.001 |
| U | 0.0034 |
| V | 0.0038 |

The inhibiting effect on tumor metastasis can also be demonstrated, according to Gastpar et al. [see Thrombosis Research 5, 227–289 (1974)], as an effect which prevents tumor cell embolism. The test compound is administered before the transplanting of the tumor cells, and the survival rate of the test animals, for example, rats, is determined by comparison with controls.

2. Antithrombotic activity

Method

The thrombocyte aggregation is determined in platelet-rich plasma from healthy test subjects using the method of Born and Cross [J. Physiol. 170, 397 (1964)]. To inhibit coagulation, the blood is mixed with 3.14 percent of sodium citrate in a volume ratio of 1:10.

Collagen-induced aggregation

The pattern of the decrease in optical density of the platelet suspension after administration of the aggregation-initiating substance is measured photometrically and recorded. The speed of aggregation is deduced from the angle of inclination of the density curve. The point of the curve where there is the most light transmittance is used to calculate the optical density.

The quantity of collagen used is as small as possible, but sufficient to produce an irreversible reaction curve. The standard commercial collagen made by Hormonchemie of Munich is used. Before the collagen is administered, the plasma is incubated with the substance for ten minutes at 37° C.

From the measurements obtained, and $EC_{50}$ is obtained graphically, relating to a 50% change in optical density by way of an inhibition of aggregation.

Results

The following table shows the results obtained:

TABLE II

| Substance | $EC_{50}$ (μmol/l) |
|---|---|
| A | 0.34 |
| B | 0.28 |
| C | 0.27 |
| D | 0.33 |
| E | 0.32 |
| F | 0.21 |
| G | 0.27 |
| H | 0.32 |
| I | 0.33 |
| K | 1.90 |
| L | 0.42 |
| Compound | |
| M | 0.25 |
| N | 0.22 |
| O | 0.27 |
| P | 0.55 |
| Q | 0.25 |
| R | 2.30 |
| S | 2.20 |
| T | 0.069 |
| U | 0.028 |
| V | 0.044 |

3. Determination of the prolongation of bleeding time

Preliminary remarks

Humans, as well as other warm-blooded animals, have an ingenious mechanism which protects them from blood loss through injury. This system consists of blood platelets (thrombocytes), which quickly seal up injured vessels due to their adhesive properties, thus bringing about primary hemostasis. In addition to this purely cellular hemostatic mechanism, the body has a blood coagulation system. In this system plasma factors (proteins) are activated and finally convert liquid plasma fibrinogen to a fibrin coagulum. The system of primary hemostasis, which is regulated mainly by the thrombocytes, and the coagulation system complement each other in their common aim of protecting the body effectively from blood loss.

With some diseases it is found that coagulation and thrombocyte aggregation also take place in intact blood vessels. The influence on the coagulation system of coumarin and heparin is known and can easily be measured using known coagulation tests wherein the coagulation time is prolonged under the influence of these substances. (Plasma recalcification time, Quick's test, thrombin time, etc.).

Since, in the event of injury, the first rapid cessation of bleeding is effected by the adhesion and aggregation of the thrombocytes at the vessel wall, the functioning of the thrombocytes can easily be determined by measuring the bleeding time with a standardized injury. The normal bleeding time in humans is between 1 and 3 minutes, assuming that there are sufficient intact, effective thrombocytes. If the number of thrombocytes is normal and the bleeding time is prolonged, this signifies an abnormality in the thrombocytes. This is found in some inborn errors of thrombocyte function. If, on the other hand, it is desired to prevent spontaneous aggregation of the thrombocytes and occlusion in the arterial system by drugs, successful therapy affecting the thrombocytes should prolong the bleeding time. Therefore, with use of an antithrombotic substance, a prolongation of the bleeding time is expected. Also, there should be a normal coagulation time since the plasma coagulation system is not affected.

Literature: W. D. Keidel: *Kurzgefasstes Lehrbuch der Physiologie*, Georg Thieme Verlag, Stuttgart 1967, page 31: The Process of Hemostasis.

Method

To measure the bleeding time, 10 mg/kg of the test compounds were administered orally to conscious mice. After one hour, 0.5 mm of the tip of the tail of each mouse was cut off, and droplets of blood were gently removed with filter paper every 30 seconds. The number of drops of blood thus obtained gives a bleeding time (5 animals per experiment).

Results

The results in the following table represent the prolongation of the bleeding time in percent as compared to a control group.

TABLE III

| Compound | Prolongation of Bleeding Time after One Hour (%) |
|---|---|
| A | >248 |
| B | >263 |
| C | >241 |
| D | >250 |
| E | 46 |
| F | >275 |
| G | >245 |
| H | >211 |
| I | >220 |
| K | 121 |
| L | >266 |
| M | 100 |
| N | 63 |
| O | >227 |
| P | 73 |
| Q | 128 |
| R | >241 |
| S | >226 |
| T | 60 |
| U | >230 |
| V | 100 |

4. Acute toxicity

The acute toxicity of the test compounds was determined, as a guide, in groups of ten mice, after oral administration of a single dose (observation period: 14 days):

TABLE IV

| Compound | Approximate Acute Toxicity |
|---|---|
| A | 1000 mg (0 out of 10 animals died) |
| B | 1000 mg (0 out of 10 animals died) |
| C | 1000 mg (0 out of 10 animals died) |
| D | 1000 mg (0 out of 10 animals died) |
| E | 1000 mg (0 out of 10 animals died) |
| R | 1000 mg (0 out of 10 animals died) |
| S | 1000 mg (0 out of 10 animals died) |

TABLE IV-continued

| Compound | Approximate Acute Toxicity |
|---|---|
| T | 1000 mg (0 out of 10 animals died) |
| U | 1000 mg (0 out of 10 animals died) |
| V | 1000 mg (0 out of 10 animals died) |

In view of the pharmacological properties mentioned above, the novel compounds of the invention are suitable for the treatment or prophylaxis of thromboembolic diseases such as coronary infarct, cebebral infarct, so-called transient ischaemic attacks, and amaurosis fugax, for the prophylaxis of arteriosclerosis, and for prophylaxis of metastasis.

For such treatment, the compounds of Formula I can be processed, optionally in combination with other active ingredients, in manner known per se, together with one or more inert conventional carriers and/or diluents, such as corn starch, lactose, sucrose, microcrystalline cellulose, magnesium stearate, polyvinylpyrrolidone, citric acid, tartaric acid, water, water/ethanol, water/glycerine, water/sorbitol, water/polyethyleneglycol, propyleneglycol, cetyl stearyl alcohol, carboxymethylcellulose, or fatty substances such as hard fat, or suitable mixtures thereof, to form conventional galenic preparations such as tablets, coated tablets, capsules, powders, infusions, suspensions, solutions, or suppositories. The daily dose for adults is from about 22.5 to 300 mg (from about 0.3 to 4 mg/kg of body weight), preferably from about 22.5 to 150 mg (from about 0.3 to 2 mg/kg of body weight), generally administered in the form of several, preferably from 2 to 4, individual doses to achieve the desired results. Dependent upon the type and body weight of the patient to be treated, on the type and severity of the disease, on the type of preparation and on the route of administration as well as on the period or interval over which the administration takes place, it may, however, be necessary to deviate from the above dosages. Thus it may be sufficient in some cases to administer more or less than the above-mentioned amounts of active ingredient. The optimum dosage and route of administration of the active ingredients which are necessary in each case can easily be determined by one skilled in the art.

The following examples are intended to illustrate the invention and should not be construed as limiting the invention thereto.

EXAMPLES

PREPARATION OF STARTING COMPOUNDS

EXAMPLE A

6-Methoxy-4,4-dimethyl-4H-3,1-benzoxazin-2-one (a) 2-Amino-5-methoxy-phenyl-dimethyl-carbinol A solution of 261 ml (4.2 mol) of methyl iodide in 100 ml of absolute ether is added dropwise, under stirring, to a suspension of 102 gm (4.2 mol) of magnesium chips in 300 ml of absolute ether over a period of two and one-half hours, and the resulting mixture is stirred for a further half hour. Then, over a period of half an hour, a solution of 181.2 gm (1 mol) of methyl 5-methoxy-anthranilate in 1.5 liters of absolute ether is added dropwise, under cooling to ensure that the temperature does not exceed 20° to 25° C. After stirring for one hour, the mixture is poured onto ice water containing ammonium chloride, the ether phase is separated, washed with water containing ammonium chloride, and dried with sodium sulfate, and the ether is distilled off.

(b) 6-Methoxy-4,4-dimethyl-4H-3,1-benzoxazin-2-one

The residue of 2-amino-5-methoxy-phenyl-dimethyl-carbinol remaining after the ether has been distilled off is dissolved, without further purification, in 1.5 liters of chloroform, 276.4 gm (2 mol) of potassium carbonate are added, and the resulting mixture is heated to 40° C. Over the course of two hours, 600 ml of a 20% solution of phosgene in toluene (1.2 mol) are added dropwise to this solution rapidly enough for the temperature of the reaction mixture to be between 40° and 50° C.; occasionally, foaming may occur. After all the solution has been added, the mixture is left to stand overnight at ambient temperature.

Then, 1 liter of water is added, the chloroform/toluene phase is separated, and the aqueous phase is extracted several times with chloroform to which some methanol has been added. The combined organic extracts are washed with water and dried with sodium sulfate, and the solvent is distilled off. The crystalline residue is recrystallized from toluene/ethyl acetate (9:1).

M.p.: 182°-183° C.,

Yield: 130 gm (64% of theory, based upon methyl 5-methoxy-anthranilate used).

By use of procedures analogous to that described above, the following compounds are prepared:

(i) 6-methoxy-4,4-di-n-hexyl-4H-3,1-benzoxazin-2-one, prepared from methyl 5-methoxy-anthranilate, n-hexylmagnesium bromide, and phosgene.
M.p.: 101°-103° C.,
Yield: 70.8% of theory.

(ii) 6-methoxy-4,4-diphenyl-4H-3,1-benzoxazin-2-one, prepared from methyl 5-methoxy-anthranilate, phenylmagnesium bromide, and phosgene.
M.p.: 237° C.,
Yield: 69.5% of theory.

(iii) 6-methoxy-4,4-dicyclohexyl-4H-3,1-benzoxazin-2-one, prepared from methyl 5-methoxy-anthranilate, cyclohexylmagnesium bromide, and phosgene.
M.p.: 269°-271° C.,
Yield: 50.4% of theory.

(iv) 6-methoxy-4-isopropyl-4H-3,1-benzoxazin-2-one, prepared from 5-methoxy-2-amino-benzaldehyde (prepared from 5-methoxy-2-nitro-benzaldehyde and Pt/H$_2$ at 30 bar and 35° C.), isopropylmagnesium iodide, and phosgene.
M.p.: 124°-125° C.,
Yield: 37.1% of theory.

(v) 6-methoxy-4-ethyl-4H-3,1-benzoxazin-2-one, prepared from 5-methoxy-2-amino-benzaldehyde, ethylmagnesium bromide, and phosgene.
M.p.: 88°-89° C.,
Yield: 30.2% of theory.

(vi) 6-methoxy-4-phenyl-4H-3,1-benzoxazin-2-one, prepared from 5-methoxy-2-amino-benzaldehyde, phenylmagnesium bromide, and phosgene.
M.p.: 157°-158° C.,
Yield: 36.3% of theory.

(vii) 6-methoxy-4,4-diethyl-4H-3,1-benzoxazin-2-one, prepared from methyl 5-methoxy-anthranilate, ethylmagnesium bromide, and phosgene.
M.p.: 123°-125° C.,
Yield: 90.1% of theory.

(viii) 6-methoxy-4-methyl-4H-3,1-benzoxazin-2-one, prepared from 5-methoxy-2-amino-benzaldehyde, methylmagnesium iodide, and phosgene.
M.p.: 120°-121° C.,
Yield: 20.2% of theory.

(ix) 5-methoxy-4,4-dimethyl-4H-3,1-benzoxazin-2-one, prepared from methyl 6-methoxy-anthranilate, methylmagnesium iodide, and phosgene.
M.p.: 139°-141° C.,
Yield: 22% of theory.

(x) 7-methoxy-4,4-dimethyl-4H-3,1-benzoxazin-2-one, prepared from methyl 4-methoxy-anthranilate, methylmagnesium iodide, and phosgene.
M.p. 119°-121° C.,
Yield: 62% of theory.

(xi) 8-methoxy-4,4-dimethyl-4H-3,1-benzoxazin-2-one, prepared from methyl 3-methoxy-anthranilate, methylmagnesium iodide, and phosgene.
M.p.: 95°-96° C.,
Yield: 42.1% of theory.

(xii) 6-methoxy-4,4,7-trimethyl-4H-3,1-benzoxazin-2-one, prepared from methyl 5-methoxy-4-methyl-anthranilate, methylmagnesium iodide, and phosgene.
M.p.: 134°-135° C.,
Yield: 45.5% of theory.

(xiii) 6-methoxy-4,4,8-trimethyl-4H-3,1-benzoxazin-2-one, prepared from methyl 5-methoxy-3-methyl-anthranilate, methylmagnesium iodide, and phosgene.
M.p.: 218°-219° C.,
Yield: 65.8% of theory.

(xiv) 6-methoxy-5,7-dichloro-4,4-dimethyl-4H-3,1-benzoxazin-2-one, prepared from methyl 5-methoxy-4,6-dichloro-anthranilate, methylmagnesium iodide, and phosgene.
M.p.: 203°-204° C.,
Yield: 44.0% of theory.

(xv) 6-methoxy-5,7-dimethyl-4H-3,1-benzoxazin-2-one, prepared from methyl 5-methoxy-4,6-dimethyl-anthranilate, methylmagnesium iodide, and phosgene.
M.p.: 152°-153° C.,
Yield: 38.7% of theory.

EXAMPLE B

6-Methoxy-4H-3,1-benzoxazin-2-one (a) 2-Amino-5-methoxy-benzyl alcohol

A quantity of 181.2 gm (1 mol) of 5-methoxy-2-nitrobenzaldehyde (prepared by methylation of 2-nitro-5-hydroxy-benzaldehyde with methyl iodide/potassium tert.-butoxide in dimethylsulfoxide) is dissolved in 1.8 liters of methanol, mixed with 50 gm of Raney nickel, and hydrogenated at ambient temperature and at 5 bar. After ten hours, the hydrogen uptake has ended. The catalyst is removed by suction filtration, and the methanol is distilled off.

(b) 6-Methoxy-4H-3,1-benzoxazin-2-one

The residue remaining after the methanol has been distilled off is dissolved, without further purification, in 1 liter of chloroform and mixed with 175 gm (1.25 mol) of potassium carbonate. Five hundred fifty-three milliliters (1.05 mol) of a 20% solution of phosgene in toluene is carefully added dropwise to this suspension at 50° C., under stirring. After stirring at ambient temperature for a further two hours, the mixture is poured onto ice water, the chloroform/toluene phase is separated, and the aqueous phase is extracted several times with chloroform/methanol (5:1). The combined organic extracts are washed with water and dried with sodium sulfate, and the solvents are distilled off. The residue is purified by column chromatography [silica gel; chloroform/acetone (19:1)]. The crystals remaining after the eluant has been distilled off melt at 154°–156° C.

Yield: 110.5 gm (61.7% of theory).

Analogously to the procedure described above, the following compound is obtained: 6-methoxy-7-chloro-4H-3,1-benzoxazin-2-one.

M.p.: 208°–210° C.,
Yield: 38.7% of theory.

EXAMPLE C

6-Hydroxy-4,4-dimethyl-4H-3,1-benzoxazin-2-one

An amount of 237.5 gm (1.146 mol) of 6-methoxy-4,4-dimethyl-4H-3,1-benzoxazin-2-one is dissolved in 2.4 liters of dry ethylene chloride, and 125 ml (330.3 gm = 1.3 mol) of boron tribromide are added thereto dropwise, under stirring, at −30° to −40° C. After the addition is complete, the mixture is allowed to return to ambient temperature and left overnight. Then, 1 liter of 50% ethanol is added dropwise, under cooling and stirring, and the mixture is evaporated down to about 500 ml and then diluted with 3 liters of water. The precipitate is subjected to suction filtration and dried.

M.p.: 202°–204° C. (from ethyl acetate/petroleum ether),
Yield: 223.3 gm (99.8% of theory).

By use of procedures analogous to that described above, the following compounds are prepared:

(i) 6-hydroxy-4H-3,1-benzoxazin-2-one,
M.p.: 244°–245° C.,
Yield: 78.5% of theory.
(ii) 6-hydroxy-4,4-di-n-hexyl-4H-3,1-benzoxazin-2-one,
M.p.: 144°–146° C.,
Yield: 92.4% of theory.
(iii) 6-hydroxy-4,4-diphenyl-4H-3,1-benzoxazin-2-one,
M.p.: 239° C. (decomp.),
Yield: 90.0% of theory.
(iv) 6-hydroxy-4-isopropyl-4H-3,1-benzoxazin-2-one,
M.p.: 215°–216° C.,
Yield: 77.6% of theory.
(v) 6-hydroxy-4-ethyl-4H-3,1-benzoxazin-2-one,
M.p.: 216°–218° C.,
Yield: 68.5% of theory.
(vi) 6-hydroxy-4,4-dicyclohexyl-4H-3,1-benzoxazin-2-one,
M.p.: >280° C.,
Yield: 97.8% of theory.
(vii) 6-hydroxy-4,4-diethyl-4H-3,1-benzoxazin-2-one,
M.p.: 194°–195° C.,
Yield: 95.5% of theory.
(viii) 6-hydroxy-4-methyl-4H-3,1-benzoxazin-2-one,
M.p.: 226° C. (decomp.),
Yield: 75.8% of theory.
(ix) 7-hydroxy-4,4-dimethyl-4H-3,1-benzoxazin-2-one,
M.p.: 180°–182° C.,
Yield: 96.8% of theory.
(x) 5-hydroxy-4,4-dimethyl-4H-3,1-benzoxazin-2-one,
M.p.: 251° C.,
Yield: 79% of theory.
(xi) 8-hydroxy-4,4-dimethyl-4H-3,1-benzoxazin-2-one,
M.p.: 203°–205° C.,
Yield: 90% of theory.
(xii) 6-hydroxy-4,4,8-trimethyl-4H-3,1-benzoxazin-2-one,
M.p.: 174° C. (decomp.),
Yield: 94.3% of theory.
(xiii) 6-hydroxy-4,4,7-trimethyl-4H-3,1-benzoxazin-2-one,
M.p. 150°–152° C.,
Yield: 85.8% of theory.
(xiv) 8-chloro-6-hydroxy-4,4-dimethyl-4H-3,1-benzoxazin-2-one,
M.p.: 196°–198° C.,
Yield: 52% of theory.
(xv) 7-chloro-6-hydroxy-4,4-dimethyl-4H-3,1-benzoxazin-2-one,
M.p.: 218°–219° C.,
Yield: 97.1% of theory.
(xvi) 7-bromo-6-hydroxy-4,4-dimethyl-4H-3,1-benzoxazin-2-one,
M.p.: 157°–158° C.,
Yield: 96% of theory.
(xvii) 8-bromo-6-hydroxy-4,4-dimethyl-4H-3,1-benzoxazin-2-one,
M.p.: 212°–214° C.,
Yield: 46.7% of theory.
(xviii) 7,8-dibromo-6-hydroxy-4,4-dimethyl-4H-3,1-benzoxazin-2-one,
M.p.: 194°–195° C.,
Yield: 24% of theory.
(xix) 6-hydroxy-7-chloro-4H-3,1-benzoxazin-2-one
M.p.: 250° C. (decomp.),
Yield: 96.2% of theory.
(xx) 6-hydroxy-5,7-dichloro-4,4-dimethyl-4H-3,1-benzoxazin-2-one,
M.p.: 215°–217° C.,
Yield: 88.0% of theory.
(xxi) 6-hydroxy-5,7-dimethyl-4H-3,1-benzoxazin-2-one,
M.p.: 210°–211° C.,
Yield: 70.5% of theory.

EXAMPLE D 6-(5-Bromo-pentoxy)-4,4-dimethyl-4H-3,1-benzoxazin-2-one

A solution of 19.3 gm (0.1 mol) of 6-hydroxy-4,4-dimethyl-4H-3,1-benzoxazin-2-one in 200 ml of dimethyl sulfoxide is heated at ambient temperature with 41.5 gm (0.3 mol) of potassium carbonate and 92 gm (0.4 mol) of 1,5-dibromopentane, whereupon the temperature rises to 45° C. After stirring a further two hours, ice water is added, and the resulting mixture is extracted with chloroform. The chloroform phase is washed with water and dried with sodium sulfate, and the chloroform is distilled off. The residue is recrystallized from ethyl acetate/petroleum ether.

M.p.: 113°–115° C.,
Yield: 26.9 gm (78.6% of theory).

By use of procedures analogous to that described above, the following compounds are prepared:

(i) 6-(3-chloropropoxy)-4-isopropyl-4H-3,1-benzoxazin-2-one, prepared from 6-hydroxy-4-isopropyl-4H-3,1-benzoxazin-2-one and 3-bromo-propylchloride.
M.p.: 104°–105° C., Yield: 68.0% of theory.
(ii) 6-(3-chloro-propoxy)-4,4-dimethyl-4H-3,1-benzoxazin-2-one, prepared from 6-hydroxy-4,4-dimethyl-4H-3,1-benzoxazin-2-one and 3-bromopropylchloride.
M.p.: 137°-138° C.,
Yield: 71.6% of theory.
(iii) 6-(6-bromo-hexyloxy)-4,4-dimethyl-4H-3,1-benzoxazin-2-one, prepared from 6-hydroxy-4,4-dimethyl-4H-3,1-benzoxazin-2-one and 1,6-dibromohexane.
M.p.: 125°-126° C.,
Yield: 59.2% of theory.
(iv) 6-(2-chloro-ethyl)-4,4-dimethyl-4H-3,1-benzoxazin-2-one, prepared from 6-hydroxy-4,4-dimethyl-4H-3,1-benzoxazin-2-one and (2-chloroethyl)benzenesulfonate.
M.p.: 128°-129° C.,
Yield: 34.4% of theory.

EXAMPLE E 6-(4-Acetoxy-butoxy)-4H-3,1-benzoxazin-2-one

One hundred two grams (0.62 mol) of 6-hydroxy-4H-3,1-benzoxazin-2-one are dissolved in 1 liter of dimethylsulfoxide and mixed with 227 gm (1.64 mol) of potassium carbonate and 166 gm (0.73 mol) of 4-acetoxybutylbromide. The reaction mixture is stirred for six hours at 50° C., and then ice water is added. The precipitate is subjected to suction filtration, washed with water, and dried.
M.p.: 119°-121° C.,
Yield: 142.8 gm (82.7% of theory).

By use of procedures analogous to that described above, the following compounds are prepared.
(i) 6-(4-acetoxy-butoxy)-4,4-dimethyl-4H-3,1-benzoxazin-2-one, Oil, RF value: 0.8 [silica gel plate; chloroform/ethanol (9:1)], Yield: 100% of theory.
(ii) 6-(4-acetoxy-butoxy)-4,4-di-n-hexyl-4H-3,1-benzoxazin-2-one, Oil, RF value: 0.6 [silica gel plate; chloroform/acetone (9:1)].
Yield: 100% of theory.
(iii) 6-(4-acetoxy-butoxy)-4,4-diphenyl-4H-3,1-benzoxazin-2-one, Oil, RF avalue: 0.55 [silica gel plate; chloroform/acetone (9:1)].
Yield: 81% of theory.
(iv) 6-(4-acetoxy-butoxy)-4,4-dicyclohexyl-4H-3,1-benzoxazin-2-one,
M.p.: 177°-178° C.,
Yield: 68.8% of theory.
(v) 7-(4-acetoxy-butoxy)-4,4-dimethyl-4H-3,1-benzoxazin-2-one, Oil, RF value: 0.5 [silica gel plate; ethylene chloride/ethanol (9:1)],
Yield: 100% of theory.
(vi) 8-(4-acetoxy-butoxy)-4,4-dimethyl-4H-3,1-benzoxazin-2-one,
M.p.: 154°-158° C.,
Yield: 100% of theory.
(vii) 6-(4-acetoxy-butoxy)-4,4-diethyl-4H-3,1-benzoxazin-2-one, Oil, RF value: 0.38 [silica gel plate; chloroform/ethanol (9:1)],
Yield: 95% of theory.
(viii) 6-(4-acetoxy-butoxy)-4methyl-4H-3,1-benzoxazin-2-one, Oil, RF value: 0.5 [silica gel plate; chloroform/ethanol (9:1)],
Yield: 98% of theory.
(ix) 6-(4-acetoxy-butoxy)-4,4-dimethyl-7-nitro-4H-3,1-benzoxazin-2-one, Oil, RF value: 0.8 [silica gel plate; chloroform/acetone (9:1)],
Yield: 97% of theory.
(x) 6-(4-acetoxy-butoxy)-4,4,8-trimethyl-4H-3,1-benzoxazin-2-one, Oil, RF value: 0.5 [silica gel plate; ethylene chloride/acetone (9:1)],
Yield: 98% of theory.

EXAMPLE F 6-(4-Hydroxy-butoxy)-4H-3,1-benzoxazin-2-one

A solution of 24 gm (0.6 mol) of sodium hydroxide in 100 ml of water is added dropwise to a solution of 150 gm (0.537 mol) of 6-(4-acetoxy-butoxy)-4H-3,1-benzoxazin-2-one in 500 ml of methanol, under stirring, at 10° to 15° C. After the mixture has been stirred for one hour at ambient temperature, first ice water and then 60 ml of glacial acetic acid are added. The product precipitated is subjected to suction filtration and recrystallized from water.
M.p.: 133°-134° C.,
Yield: 61.5 gm (48.4% of theory).

By use of procedures analogous to that described above, the following compounds are prepared:
(i) 6-(4-hydroxy-butoxy)-4,4-dimethyl-4H-3,1-benzoxazin-2-one,
M.p.: 124° C.,
Yield: 82.9% of theory.
(ii) 6-(4-hydroxy-butoxy)-4,4-diphenyl-4H-3,1-benzoxazin-2-one,
M.p.: 188°-189° C.,
Yield: 79% of theory.
(iii) 6-(4-hydroxy-butoxy)-4,4-di-n-hexyl-4H-3,1-benzoxazin-2-one,
M.p.: 105°-107° C.,
Yield: 56% of theory.
(iv) 6-(4-hydroxy-butoxy)-4,4-dicyclohexyl-4H-3,1-benzoxazin-2-one,
M.p.: 233°-234° C.,
Yield: 77.6% of theory.
(v) 7-(4-hydroxy-butoxy)-4,4-dimethyl-4H-3,1-benzoxazin-2-one,
M.p.: 105°-106° C.,
Yield: 53.4% of theory.
(vi) 8-(4-hydroxy-butoxy)-4,4-dimethyl-4H-3,1-benzoxazin-2-one,
M.p.: 150°-151° C.,
Yield: 73% of theory.
(vii) 6-(4-hydroxy-butoxy)-4,4-diethyl-4H-3,1-benzoxazin-2-one,
M.p.: 126°-127° C.,
Yield: 69.3% of theory.
(viii) 6-(4-hydroxy-butoxy)-4-methyl-4H-3,1-benzoxazin-2-one, Oil, RF value: 0.4 [silica gel plate; chloroform/ethanol (9:1)],
Yield: 61.6% of theory.
(ix) 6-(4-hydroxy-butoxy)-4,4-dimethyl-7-nitro-4H-3,1-benzoxazin-2-one,
M.p.: 140°-141° C.,
Yield: 37.8% of theory.
(x) 6-(4-hydroxy-butoxy)-4,4,8-trimethyl-4H-3,1-benzoxazin-2-one,
M.p.: 128°-129° C.,
Yield: 64.2% of theory.

EXAMPLE G

6-(4-Chloro-butoxy)-4H-3,1-benzoxazin-2-one

Sixty grams (0.253 mol) of 6-(4-hydroxy-butoxy)-4H-3,1-benzoxazin-2-one and 5 ml of pyridine are added to 300 ml of thionyl chloride, under stirring, at ambient temperature. After refluxing for two hours, the excess thionyl chloride is distilled off in a rotary evaporator, and the residue is taken up in chloroform and is stirred with the same volume of ice water for 30 minutes. Then, the chloroform phase is removed, washed twice with water, and dried with sodium sulfate, and the chloroform is distilled off. The residue is recrystallized from toluene/diisopropylether (3:1).

M.p. 127°-128° C.,

Yield: 53 gm (81.9% of theory).

By use of procedures analogous to that described above, the following compounds are prepared:

(i) 6-(4-chloro-butoxy)-4,4-dimethyl-4H-3,1-benzoxazin-2-one,

M.p.: 138°-139° C.,

Yield: 75.7% of theory.

(ii) 6-(4-chloro-butoxy)-4,4-di-n-hexyl-4H-3,1-benzoxazin-2-one, Oil, RF value: 0.65 [silica gel plate; chloroform/acetone (9:1)], Yield: 100% of theory.

(iii) 6-(4-chloro-butoxy)-4,4-diphenyl-4H-3,1-benzoxazin-2-one, Oil, RF value: 0.38 [silica gel plate; cyclohexane/ethyl acetate (9:1)], Yield: 28.7% of theory.

(iv) 6-(4-chloro-butoxy)-4,4-dicyclohexyl-4H-3,1-benzoxazin-2-one,

M.p.: 231°-232° C.,

Yield: 72.8% of theory.

(v) 6-(4-chloro-butoxy)-4,4-diethyl-4H-3,1-benzoxazin-2-one,

M.p.: 90°-92° C.,

Yield: 99.4% of theory.

(vi) 6-(4-chloro-butoxy)-4-methyl-4H-3,1-benzoxazin-2-one, Oil, RF value: 0.8 [silica gel plate; chloroform/ethanol (9:1)], Yield: 32.1% of theory.

(vii) 8-(4-chloro-butoxy)-4,4-dimethyl-4H-3,1-benzoxazin-2-one,

M.p: 155°-156° C.,

Yield: 93.8% of theory.

(viii) 6-(4-chloro-butoxy)-4,4,8-trimethyl-4H-3,1-benzoxazin-2-one,

M.p.: 149°-150° C.,

Yield: 95.6% of theory.

EXAMPLE H

7-(4-Methanesulfonyloxy-butoxy)-4,4-dimethyl-4H-3,1-benzoxazin-2-one

A quantity of 5.3 gm (0.02 mol) of 7-(4-hydroxy-butoxy)-4,4-dimethyl-4H-3,1-benzoxazin-2-one is dissolved in 20 ml of pyridine, and at 0° to 5° C., 4.6 gm (0.04 mol) of methanesulfonic acid chloride are added dropwise, under stirring. After stirring for a further ten minutes, ice water/hydrochloric acid is added, and the mixture is extracted with chloroform. After the extract has been washed with water and dried with sodium sulfate, the solvent is distilled off in vacuo. The solid residue is stirred with diisopropyl ether, subjected to suction filtration, and dried.

M.p.: 134°-136° C.,

Yield: 6.4 gm (93.3% of theory).

By use of analogous procedure, the following compound is prepared: 6-(4-methanesulfonyloxy-butoxy)-4,4-dimethyl-7-nitro-4H-3,1-benzoxazin-2-one, M.p.: 149°-151° C., Yield: 76.6% of theory.

EXAMPLE I

Methyl 3-methoxy-anthranilate

One hundred thirty-three grams (0.63 mol) of methyl 3-methoxy-2-nitro-benzoate are dissolved in 1000 ml of toluene and hydrogenated in an autoclave at ambient temperature and under a hydrogen pressure of 5 bar in the presence of platinum over a period of two hours. The catalyst is removed by filtration, the residue is dried with sodium sulfate, and the toluene is distilled off in vacuo. Oil, RF value: 0.8 [silica gel plate; chloroform/acetone (9:1)], Yield: 110 gm (96.4% of theory).

Due to its relative instability, the substance prepared is preferably not stored but is reacted immediately analogously to Example A.

EXAMPLE J

Methyl 6-methoxy-anthranilate hydrochloride (a) 2-Cyano-3-methoxy-aniline

One hundred ten grams (0.617 mol) of 2-methoxy-6-nitro-benzonitrile are dissolved in 1 liter of methanol and hydrogenated in the presence of 10% palladium on charcoal at ambient temperature and under a hydrogen pressure of 5 bar over a period of one hour. The catalyst is removed by filtration, the solvent is distilled off, and the residue is recrystallized from ethanol/diisopropyl ether.

M.p: 142°-143° C.,

Yield: 54.8 gm (59.9% of theory).

(b) 6-Methoxy-anthranilic acid

Fifty-four grams (0.364 mol) of the product prepared in (a) are refluxed with 800 ml of a 25% aqueous solution of potassium hydroxide for 16 hours. After cooling, the reaction solution is adjusted to a pH of 6 by the addition of acetic acid and then extracted several times, each time with one-half liter of ethyl acetate. The combined extracts are dried with sodium sulfate, and the ethyl acetate is distilled off. The residue is purified by column chromatography [silica gel; ethylene chloride/acetone (19:1)]. The uniform fractions are concentrated to dryness.

M.p: 76°-78° C.,

Yield: 37.5 gm (61.7% of theory).

(c) Methyl 6-methoxy-anthranilate hydrochloride

The acid obtained in (b) (37.5 gm=0.22 mol) is dissolved in 500 ml of methanol, and hydrogen chloride dried over concentrated sulfuric acid is introduced into the solution for two hours. A thick crystal slurry is obtained, which is mixed with 500 ml of ether, subjected to suction filtration, and washed again with ether.

M.p.: 209° C. (decomp.),

Yield: 36.5 gm (75.2% of theory).

EXAMPLE K

Methyl 4-methoxy-anthranilate (a) 3-(Isonitroso-acetamido)-anisole

One thousand four hundred eighty grams (10.38 mol) of sodium sulfate and 225 gm (1.36 mol) of chloral hydrate are dissolved in 6 liters of water and heated to 50° C. Then, a solution of 154 gm (1.25 mol) of m-anisidine in 750 ml of water and 125 ml of concentrated hydrochloric acid is added thereto, under stirring. After a further five minutes, a solution of 275 gm (3.96 mol) of hydroxyl ammonium hydrochloride in 1.25 liters of water is added, and the resulting mixture is heated to 95° C. While stirring is continued, the mixture is left to cool to ambient temperature, and the precipitate is subjected to suction filtration, washed with water, and dried.

M.p.: 165°-166° C.,
Yield: 242.5 gm (99.9% of theory).
The following compounds are prepared by analogous procedures:
(i) 4-(isonitroso-acetamido)-3-methylanisole,
M.p.: 166°-167° C.,
Yield: 94.1% of theory.
(ii) 4-(isonitroso-acetamido)-2-methylanisole,
M.p.: 169°-171° C.,
Yield: 86.2% of theory.
(iii) 2-chloro-4-(isonitroso-acetamido)-anisole,
M.p.: 208° C.,
Yield: 91.6% of theory.

(b) 6-Methoxy-isatine

One hundred forty grams (0.72 mol) of 3-isonitroso-acetamido)-anisole are stirred into 720 gm of polyphosphoric acid at 60° C. The mixture heats up to about 100° C. The reaction mixture is stirred at this temperature for a further 30 minutes and is then cooled and poured, under stirring, into 4 liters of water at 30° C. After standing overnight, the precipitate is subjected to suction filtration, washed with water, and extracted with acetone/chloroform (1:1). The solution is dried with sodium sulfate, and the solvents are distilled off. The residue is mixed with ethanol, subjected to suction filtration, and dried at ambient temperature.

M.p: 237°-238° C.,
Yield: 84.2 gm (65.9% of theory).
The following compounds are prepared by analogous procedures:
(i) 5-methoxy-7-methyl-isatine
M.p: 265°-266° C.;
Yield: 36% of theory.
(ii) 5-methoxy-6-methyl isatine,
M.p.: 254°-256° C.;
Yield: 87.2% of theory.
(iii) 6-chloro-5-methoxy-isatine,
M.p.: 247° C.,
Yield: 33.2% of theory.

(c) Methyl 4-methoxy-anthranilate

One hundred fifty-eight grams (0.89 mol) of 6-methoxy-isatine are suspended in 1300 ml of methanol and mixed with a solution of 54 gm (1.34 mol) of sodium ethoxide in 500 ml of methanol. One hundred eight milliliters (1.07 mol) of 30% hydrogen peroxide are added thereto dropwise, under stirring, and the resulting mixture is stirred for 30 minutes. The contents of the flask are concentrated down to half their volume, mixed with water, and adjusted to a pH of 5 to 6 with glacial acetic acid. After extraction with methylene chloride, the mixture is subjected to suction filtration, kieselguhr being used, and dried with sodium sulfate, and the solvent is distilled off. The residue is recrystallized from petroleum ether/cyclohexane (2:1).

M.p: 80°-82° C.,
Yield: 109 gm (67.7% of theory).
The following compounds are prepared by analogous procedures:
(i) methyl 5-methoxy-3-methyl-anthranilate,
M.p.: 81°-82° C.,
Yield: 59.6% of theory.
(ii) methyl 5-methoxy-4-methyl-anthranilate,
M.p.: 84°-86° C.,
Yield: 82.2% of theory.

EXAMPLE L

8-Chloro-6-methoxy-4,4-dimethyl-4H-3,1-benzoxazin-2-one and
7-Chloro-6-methoxy-4,4-dimethyl-4H-3,1-benzoxazin-2-one A solution of 79 gm (0.38 mol) of 6-methoxy-4,4-dimethyl-4H-3,1-benzoxazin-2-one in 1000 ml of chloroform is mixed with 56.68 gm (0.42 mol) of sulfuryl chloride and stirred for six hours at 10° to 20° C. After standing overnight, the reaction mixture is mixed with an aqueous sodium carbonate solution, the organic phase is separated off, washed with water, and dried with sodium sulfate, and the chloroform is distilled off. The residue is separated by column chromatography into its isomers [silica gel; ethylene chloride/acetone (19:1)]. The uniform fractions are evaporated to dryness, and the residue is recrystallized from ethyl acetate/diisopropyl ether.

(1) 8-chloro-6-methoxy-4,4-dimethyl-4H-3,1-benzoxazin-2-one,
M.p.: 156°-157° C.,
Yield: 47.3 gm (51.6% of theory).
(2) 7-chloro-6-methoxy-4,4-dimethyl-4H-3,1-benzoxazin-2-one,
M.p.: 165°-167° C.,
Yield: 18.9 gm (20.6% of theory).

EXAMPLE M

8-Bromo-6-methoxy-4,4-dimethyl-4H-3,1-benzoxazin-2-one and
7-Bromo-6-methoxy-4,4-dimethyl-4H-3,1-benzoxazin-2-one An amount of 82.7 gm (0.4 mol) of 6-methoxy-4,4-dimethyl-4H-3,1-benzoxazin-2-one is dissolved in 800 ml of dioxane, and 67.1 gm (21.5 ml=0.42 mol) of bromine are added dropwise at ambient temperature. After stirring for three hours, a further 67.1 gm of bromine are added, and after an additional three hours, a third batch of 67.1 gm of bromine is added. Stirring is continued overnight. The reaction mixture is then mixed with ice water and sodium bisulfite solution and extracted with ethyl acetate. The extract is washed with water and dried with sodium sulfate, and the ethyl acetate is distilled off. The residue is resolved into its isomers by column chromatography [silica gel; ethylene chloride/acetone (60:1)]. The pure fractions are concentrated by evaporation and recrystallized from ethyl acetate/diisopropylether.

(1) 8-bromo-6-methoxy-4,4-dimethyl-4H-3,1-benzoxazin-2-one,
M.p.: 128°-130° C. (still contains a small amount of 7,8-dibromo-6-methoxy-4,4-dimethyl-4H-3,1-benzoxazin-2-one),
Yield: 45 gm (39.3% of theory).
(2) 7-bromo-6-methoxy-4,4-dimethyl-4H-3,1-benzoxazin-2-one,
M.p.: 174°-175° C., Yield: 33.7 gm (29.5% of theory).

EXAMPLE N

6-Acetoxy-8-chloro-4H-3,1-benzoxazin-2-one

A quantity of 14.5 gm (0.07 mol) of 6-acetoxy-4H-3,1-benzoxazin-2-one (prepared from 6-hydroxy-4H-3,1-benzoxazin-2-one and acetic anhydride; m.p. 173°–175° C.) is dissolved in 150 ml of glacial acetic acid, mixed with 10.8 gm (6.5 ml=0.08 mol) of sulfuryl chloride, and stirred for 36 hours at ambient temperature. After addition of 30 ml of ether, the mixture is cooled to 0° C., and the precipitate is subjected to suction filtration, washed with ether, and dried.

M.p.: 204°–205° C.,

Yield: 7.7 gm (45.5% of theory).

EXAMPLE O

8-Chloro-6-hydroxy-4H-3,1-benzoxazin-2-one

An amount of 7.6 gm (31.4 mol) of 6-acetoxy-8-chloro-4H-3,1-benzoxazin-2-one is suspended in 50 ml of methanol, and 20 ml (40 mmol) of 2N sodium hydroxide solution are added, under stirring. The clear solution which is immediately produced is stirred for a further ten minutes at ambient temperature, water is added, and the mixture is made acidic with acetic acid. The precipitate is subjected to suction filtration and recrystallized from isopropanol.

M.p.: 250° C. (decomp.),

Yield: 3.3 gm (52.7% of theory).

PREPARATION OF COMPOUNDS OF FORMULA I

EXAMPLE 1

6-[4-(4-Bromo-phenylmercapto)-butoxy]-4,4-dimethyl-4H-3,1-benzoxazin-2-one

Quantities of 6.23 gm (0.033 mol) of 4-bromothiophenol and 8.28 gm (0.06 mol) of potassium carbonate are stirred into 100 ml of dimethylsulfoxide, dried over a molecular sieve in a nitrogen atmosphere at ambient temperature for 15 minutes, and then mixed with 8.51 gm (0.03 mol) of 6-(4-chlorobutoxy)-4,4-dimethyl-4H-3,1-benzoxazin-2-one. After stirring for one hour at ambient temperature, water is added in batches until a thick crystal slurry is produced. This is subjected to suction filtration, dried, and recrystallized from ethyl acetate/diisopropyl ether.

M.p.: 151°–152° C.,

Yield: 9.2 gm (70.3% of theory).

EXAMPLE 2

6-[4-(4-Bromo-3-methyl-phenylsulfinyl)-butoxy]-4,4-dimethyl-4H-3,1-benzoxazin-2-one An amount of 9.2 gm (0.02 mol) of 6-[4-(4-bromo-3-methyl-phenylmercapto)-butoxy]-4,4-dimethyl-4H-3,1-benzoxazin-2-one is dissolved in 100 ml of glacial acetic acid, and 2 ml (0.02 mol) of 30% hydrogen peroxide are added. The mixture is stirred for three hours at ambient temperature, poured onto 400 ml of water, and extracted three times with ethyl acetate. The organic phase is washed with water and dried with sodium sulfate, and the ethyl acetate is distilled off. The solid residue is recrystallized from ethyl acetate/diisopropyl ether.

M.p.: 133°–134° C.,

Yield: 8.1 gm (85.2% of theory).

EXAMPLE 3

4,4-Dimethyl-6-[4-(2-pyridylsulfonyl)-butoxy]-4H-3,1-benzoxazin-2-one

A quantity of 3.58 gm (0.01 mol) of 4,4-dimethyl-6-[4-(2-pyridylmercapto)-butoxy]-4H-3,1-benzoxazin-2-one is dissolved in 60 ml of formic acid, and 2.5 ml (0.025 mol) of 30% hydrogen peroxide are added. After stirring for three hours at ambient temperature, the mixture is diluted by the addition of batches of water and then extracted with ethyl acetate; the organic phase is dried with sodium sulfate; and the ethyl acetate is distilled off. For purification, the residue is chromatographed on a silica gel column (particle size of 0.05 to 0.2 mm) with a mixture of chloroform/ethanol (40:1), and the uniform fractions are recrystallized from ethyl acetate after the eluant mixture has been distilled off.

M.p.: 142°–143° C.,

Yield: 2.1 gm (53.8% of theory).

EXAMPLE 4

6-[4-(3,4-Dichloro-phenylsulfinyl)-butoxy]-4,4-dimethyl-4H-3,1-benzoxazin-2-one A solution of 1.9 gm (0.01 mol) of 6-hydroxy-4,4-dimethyl-4H-3,1-benzoxazin-2-one and 4.1 gm (0.0125 mol) of 4-(3,4-dichlorophenyl-sulfinyl)-butylbromide (m.p.: 63°–64° C.) in 40 ml of dimethylsulfoxide is mixed with 3.5 gm (0.025 mol) of potassium carbonate, and the mixture is stirred for three hours at 40° C. After cooling, copious amounts of ice water are added, and the mixture is extracted with chloroform. The extract is washed with water and dried with sodium sulfate, and the chloroform is distilled off. The residue is recrystallized from isopropanol/diisopropylether.

M.p.: 138° C.,

Yield: 1.9 gm (43% of theory).

EXAMPLE 5

6-(4-Phenylmercapto-butoxy)-4H-3,1-benzoxazin-2-one

An amount of 4.95 gm (0.03 mol) of 6-hydroxy-4H-3,1-benzoxazin-2-one is added to an ethanolic sodium ethoxide solution prepared from 150 ml of ethanol and 0.92 gm (9.04 mol) of sodium, and the mixture is refluxed. Ten grams (0.04 mol) of 4-phenylmercapto-butylbromide (prepared from thiophenol and excess 1,4-di-bromo-butane, Bp $_{0.03\ mb}$:=95°–104° C.) are added to the hot solution, and the mixture is refluxed for a further two hours. After cooling, the reaction solution is poured onto ice water and extracted with ethyl acetate. The extract is washed with water and dried with sodium sulfate, and the ethyl acetate is distilled off in vacuo. The residue is recrystallized from cyclohexane/ethyl acetate.

M.p.: 96°–97° C.,

Yield: 51.7% of theory.

EXAMPLE 6

6-[4-(3,4-Dichloro-phenylsulfoximino)-butoxy]-4,4-dimethyl-4H-31,-benzoxazin-2-one A solution of 32.65 gm (0.074 mol) of 6-[4-(3,4-dichloro-phenylsulfinyl)-butoxy]-4,4-dimethyl-4H-3,1-benzoxazin-2-one in 300 ml of dimethyl formamide is mixed with 66.6 gm (0.35 mol) of p-toluenesulfonic acid monohydrate and 42.9 gm (0.15 mol) of ethyl O-mesitylenesulfonyl-acethydroxamate, and the mixture is stirred for 30 hours at ambient temperature. After addition of ice water, the mixture is extracted with ethyl acetate; the ethyl acetate phase is washed with water and dried with sodium sulfate; and the ethyl acetate is distilled off in vacuo. The residue is dissolved in 200 ml of methanol, and the solution is mixed with sufficient 2N sodium hydroxide solution to produce an alkaline reaction. The reaction product is precipitated by the addition of water and extracted with ethyl acetate, and the extract is washed with water and dried with sodium sulfate. The residue remaining after the ethyl acetate has been distilled off is recrystallized from ethyl acetate/diisopropylether.

M.p.: 166°–167° C.,

Yield: 28.3 gm (83.8% of theory).

EXAMPLE 7

6-[4-(2-Pyridylsulfinyl)-butoxy]-4,4-dimethyl-4H-3,1-benzoxazin-2-one

A quantity of 3.58 gm (0.01 mol) 6-[4-(2-pyridylmercapto)-butoxy]-4,4-dimethyl-4H-3,1-benzoxazin-2-one is dissolved in 100 ml of chloroform and mixed with 4.3 gm (0.025 mol) of m-chloroperbenzoic acid, under stirring. After stirring for two hours, a further 2 gm of m-chloroperbenzoic acid are added, and the mixture is left to stand overnight. The chloroform phase is extracted with water, the organic phase is dried with sodium sulfate, and the chloroform is distilled off. The non-uniform residue is purified by column chromatography [silica gel, particle size of 0.05 to 0.2 mm; chloroform/ethanol (40:1)]. The uniform fractions are combined, and the residue is triturated with ethyl acetate/ether. The crystals thus obtained are subjected to suction filtration and dried at 50° C.

M.p.: 90°–91° C. (decomp.),

Yield: 1.0 gm (26.7% of theory).

EXAMPLE 8

6-[4-(3,4-Dichloro-phenylsulfinyl)-butoxy]-4,4-dimethyl-4H-3,1-benzoxazin-2-one

An amount of 2.14 gm (0.005 mol) of 6-[4-(3,4-dichlorophenyl-mercapto)-butoxy]-4,4-dimethyl-4H-3,1-benzoxazin-2-one is dissolved in 50 ml of methanol, mixed with a solution of 1.3 gm (0.06 mol) of sodium metaperiodate in 10 ml of water, and stirred for two hours at ambient temperature. Then, the mixture is refluxed for three hours, the volume of the reaction mixture is reduced by evaporation to about three-quarters, and water is added. The oil precipitated is separated by decanting of the solvent and is taken up in hot isopropanol/disiopropylether. Upon cooling, crystals are obtained which have a melting point of 138°–139° C.

Yield: 1.6 gm (72.4% of theory).

EXAMPLE 9

6-[4-(3,4-Dichloro-phenylsulfinyl)-butoxy]-4,4-dimethyl-4H-3,1-benzoxazin-2-one

A solution of 1 gm (0.0085 mol) of sulfurylchloride in 5 ml of methylene chloride is added dropwise, at −70° C., to a solution of 3.2 gm (0.0075 mol) of 6-[4-(3,4-dichloro-phenylmercapto)-butoxy]-4,4-dimethyl-4H-3,1-benzoxazin-2-one in 50 ml of methylene chloride, under stirring, and after it has all been added, stirring is continued at −70° C. for 15 hours. After heating to ambient temperature, aqueous soda solution is added, under vigorous stirring, and the organic phase is separated from the aqueous phase, washed with water, and dried with sodium sulfate. The residue remaining after the methylene chloride has been distilled off is recrystallized from isopropanol/diisopropyl ether.

M.p.: 138°–139° C.,

Yield: 2.1 gm (63.3% of theory).

EXAMPLE 10

6-[4-(3,4-Dichloro-phenylsulfinyl)-butoxy]-4,4-dimethyl-4H-3,1-benzoxazin-2-one

One gram (0.0056 mol) of N-bromosuccinimide is gradually added to a solution of 2.13 gm (0.005 mol) of 6-[4-(3,4-dichlorophenylmercapto)-butoxy]-4,4-dimethyl-4H-3,1-benzoxazin-2-one in 50 ml of methanol, under stirring. After reaction for 24 hours, 500 ml of water at 80° C. is added, and the precipitate is subjected to suction filtration after stirring for two hours. By recrystallization from isopropanol/diisopropylether, crystals are obtained, melting point: 136°–139° C.

Yield: 1.55 gm (70.1% of theory).

EXAMPLE 11

6-[4-(3,4-Dichloro-phenylsulfinyl)-butoxy]-1,4,4-trimethyl-4H-3,1-benzoxazin-2-one A solution of 1.1 gm (0.0025 mol) of 6-[4-(3,4-dichloro-phenylsulfinyl)-butoxy]-4,4-dimethyl-4H-3,1-benzoxazin-2-one and 1 ml of methyl iodide in 30 ml of methylene chloride are mixed with 30 ml of 2N sodium hydroxide solution (0.06 mol) and a spatula tip of tetrabutylammonium hydrogen sulfate, and the mixture is stirred for 18 hours at ambient temperature. The organic phase is separated, washed twice with water, and dried with sodium sulfate, and the methylene chloride is distilled off. The residue is purified by column chromatography [silica gel; chloroform/acetone (40:1)]. The uniform fractions are concentrated by evaporation, the residue is stirred with diisopropylether, and the crystal slurry is subjected to suction filtration and dried.

M.p.: 90°–92° C.,

Yield: 0.31 gm (27.3% of theory).

EXAMPLE 12

6-[4-(3,4-Dichloro-N-methanesulfonyl-phenylsulfoximino)-butoxy]-4,4-dimethyl-4H-3,1-benzoxazin-2-one An amount of 2.3 gm (0.005 mol) of 6-[4-(3,4-dichloro-phenylsulfoximino)-butoxy]-4,4-dimethyl-4H-3,1-benzoxazin-2-one is dissolved in 50 ml of chloroform and mixed with 0.5 ml of pyridine. Then, 1.2 gm (0.01 mol) of methanesulfonylchloride are added to this solution, and it is stirred for 20 hours at ambient temperature. The chloroform phase is washed several times with water and dried with sodium sulfate, and the chloroform is distilled off. The residue is purified by column chromatography [silica gel; chloroform/ethanol (30:1)]. The uniform fractions are concentrated by evaporation, and the residue is recrystallized from butanol/dimethylformamide.

M.p.: 198°–200° C.

Yield: 2.4 gm (89.6% of theory).

EXAMPLE 13

6-[4-(3,4-Dimethoxy-phenylmercapto)-butoxy]-4,4-dimethyl-4H-3,1-benzoxazin-2-one Prepared analogously to Example 1 from 6-(4-chlorobutoxy)-4,4-dimethyl-4H-3,1-benzoxazin-2-one and 3,4-dimethoxy-thiophenol.

M.p.: 140°–142° C.,

Yield: 65.9% of theory.

EXAMPLE 14

6-[4-(4-Methoxy-phenylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 4-methoxy-thiophenol.
M.p.: 92°–94° C.,
Yield: 55.5% of theory.

EXAMPLE 15

6-[4-(4-Hydroxy-phenylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 4-hydroxy-thiophenol.
M.p.: 152°–154° C.,
Yield: 92.8% of theory.

EXAMPLE 16

6-[4-(4-Biphenylylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 4-phenyl-thiophenol.
M.p.: 120°–122° C.,
Yield: 87.2% of theory.

EXAMPLE 17

6-[4-(3-Methoxy-phenylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 3-methoxy-thiophenol.
M.p.: 115°–116° C.,
Yield: 79.6% of theory.

EXAMPLE 18

6-[4-(3-Methyl-phenylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 3-methyl-thiophenol.
M.p.: 103°–105° C.,
Yield: 80.8% of theory.

EXAMPLE 19

6-[4-(3,5-Di-tert.butyl-4-hydroxy-phenylmercapto)-butoxy]-4,4-dimethyl-4H-3,1-benzoxazin-2-one Prepared analogously to Example 1 from 6-(4-chlorobutoxy)-4,4-dimethyl-4H-3,1-benzoxazin-2-one and 3,5-di-tert.butyl-4-hydroxy-thiophenol.
M.p.: 86°–87° C.,
Yield: 76.2% of theory.

EXAMPLE 20

6-[4-(4-Amino-3,5-dibromo-phenylmercapto)-butoxy]-4,4-dimethyl-4H-3,1-benzoxazin-2-one Prepared analogously to Example 1 from 6-(4-chlorobutoxy)-4,4-dimethyl-4H-3,1-benzoxazin-2-one and 4-amino-3,5-dibromo-thiophenol.
M.p.: 152°–155° C.,
Yield: 85.5% of theory.

EXAMPLE 21

6-(4-n-Octylmercapto-butoxy)-4,4-dimethyl-4H-3,1-benzoxazin-2-one

Prepared analogously to Example 1 from 6-(4-chlorobutoxy)-4,4-dimethyl-4H-3,1-benzoxazin-2-one and n-octylmercaptan.
Oil, RF Value: 0.8 [silica gel plate; chloroform/acetone (9:1)].
Yield: 96.1% of theory.
$C_{22}H_{35}NO_3S$: (393.59) Calculated: C: 67.14, H: 8.96, N: 3.56, S: 8.15. Found: C: 67.31, H: 9.00, N: 3.57, S: 8.25.

EXAMPLE 22

6-(4-Cyclohexylmercapto-butoxy)-4,4-dimethyl-4H-3,1-benzoxazin-2-one

Prepared analogously to Example 1 from 6-(4-chlorobutoxy)-4,4-dimethyl-4H-3,1-benzoxazin-2-one and cyclohexylmercaptan.
M.p.: 105°–107° C.,
Yield: 82.5% of theory.

EXAMPLE 23

6-[4-(4-Methyl-phenylmercapto)-butoxy]-4,4-di-n-hexyl-4H-3,1-benzoxazin-2-one

Prepared analogously to Example 1 from 6-(4-chlorobutoxy)-4,4-di-n-hexyl-4H-3,1-benzoxazin-2-one and 4-methyl-thiophenol.
M.p.: 76°–78° C.,
Yield: 78.1% of theory.

EXAMPLE 24

6-[4-(4-Cyclohexyl-phenylmercapto)-butoxy]-4,4-di-n-hexyl-4H-3,1-benzoxazin-2-one Prepared analogously to Example 1 from 6-(4-chlorobutoxy)-4,4-di-n-hexyl-4H-3,1-benzoxazin-2-one [oil, RF value: 0.7; silica gel plate; chloroform/acetone (19:1)] and 4-cyclohexyl-thiophenol.
M.p.: 87°–89° C.,
Yield: 75.4% of theory.

EXAMPLE 25

6-[4-(3,4-Dichloro-phenylmercapto)-butoxy]-4,4-di-n-hexyl-4H-3,1-benzoxazin-2-one Prepared analogously to Example 1 from 6-(4-chlorobutoxy)-4,4-di-n-hexyl-4H-3,1-benzoxazin-2-one and 3,4-dichloro-thiophenol.
M.p.: 63°–64° C.,
Yield: 67.9% of theory.

EXAMPLE 26

6-[4-(4-Acetamido-phenylmercapto)-butoxy]-4,4-di-n-hexyl-4H-3,1-benzoxazin-2-one Prepared analogously to Example 1 from 6-(4-chlorobutoxy)-4,4-di-n-hexyl-4H-3,1-benzoxazin-2-one and 4-acetamido-thiophenol.
Oil, RF value: 0.5 [silica gel plate; chloroform/ethanol (9:1)],
Yield: 98.2% of theory.

EXAMPLE 27

6-[4-(3,4-Dichloro-phenylmercapto)-butoxy]-4,4-dicyclohexyl-4H-3,1-benzoxazin-2-one Prepared analogously to Example 1 from 6-(4-chlorobutoxy)-4,4-dicyclohexyl-4H-3,1-benzoxazin-2-one and 3,4-dichloro-thiophenol.
M.p.: 181°–182° C.,
Yield: 77% of theory.

EXAMPLE 28

6-[4-(3,4-Dichloro-phenylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 3,4-dichloro-thiophenol.
M.p.: 155°–156° C.,
Yield: 72.8% of theory.

EXAMPLE 29

6-[4-(4-Acetamido-phenylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 4-acetamido-thiophenol.
M.p.: 158° C.,
Yield: 56.3% of theory.

EXAMPLE 30

6-[4-(2-Pyridylmercapto)-butoxy]-4,4-dimettyl-4H-3,1-benzoxazin-2-one

Prepared analogously to Example 1 from 6-(4-chlorobutoxy)-4,4-dimethyl-4H-3,1-benzoxazin-2-one and 2-mercaptopyridine.
M.p.: 137°–138° C.,
Yield: 72.5% of theory.

EXAMPLE 31

6-[4-(4-Cyclohexyl-phenylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 4-cyclohexyl-thiophenol.
M.p.: 109°–110° C.,
Yield: 47% of theory.

EXAMPLE 32

6-[4-(4-Methyl-phenylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 4-methyl-thiophenol.
M.p.: 120°–121° C.,
Yield: 69.1% of theory.

EXAMPLE 33

6-[4-(4-Bromo-3-methyl-phenylmercapto)-butoxy]-4,4-dimethyl-4H-3,1-benzoxazin-2-one Prepared analogously to Example 1 from 6-(4-chlorobutoxy)-4,4-dimethyl-4H-3,1-benzoxazin-2-one and 4-bromo-3-methyl-thiophenol.
M.p.: 129°–130° C.,
Yield: 57.0% of theory.

EXAMPLE 34

6-[4-(4-Fluoro-phenylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 4-fluoro-thiophenol.
M.p.: 125°–126° C.,
Yield: 75.5% of theory.

EXAMPLE 35

6-[4-(4-tert.Butyl-phenylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 4-tert.butyl-thiophenol.
M.p.: 119°–120° C.,
Yield: 76.6% of theory.

EXAMPLE 36

6-(4-Benzylmercapto-butoxy)-4,4-dimethyl-4H-3,1-benzoxazin-2-one

Prepared analogously to Example 1 from 6-(4-chlorobutoxy)-4,4-dimethyl-4H-3,1-benzoxazin-2-one and benzylmercaptan.
M.p.: 90°–92° C.,
Yield: 64.6% of theory.

EXAMPLE 37

6-(4-Methylmercapto-butoxy)-4,4-dimethyl-4H-3,1-benzoxazin-2-one

Prepared analogously to Example 1 from 6-(4-chlorobutoxy)-4,4-dimethyl-4H-3,1-benzoxazin-2-one and methylmercaptan.
M.p.: 98°–99° C.,
Yield: 75.4% of theory.

EXAMPLE 38

6-[4-(4-Methyl-phenylmercapto)-butoxy]-4,4-dicyclohexyl-4H-3,1-benzoxazin-2-one

Prepared analogously to Example 1 from 6-(4-chlorobutoxy)-4,4-dicyclohexyl-4H-3,1-benzoxazin-2-one and 4-methyl-thiophenol.
M.p.: 149°–150° C.,
Yield: 81.4% of theory.

EXAMPLE 39

6-[4-(4-Methyl-phenylmercapto)-butoxy]-4H-3,1-benzoxazin-2-one

Prepared analogously to Example 1 from 6-(4-chlorobutoxy)-4H-3,1-benzoxazin-2-one and 4-methyl-thiophenol.
M.p.: 125°–126° C.,
Yield: 74.7% of theory.

EXAMPLE 40

6-[4-(4-Cyclohexyl-phenylmercapto)-butoxy]-4,4-dicyclohexyl-4H-3,1-benzoxazin-2-one Prepared analogously to Example 1 from 6-(4-chlorobutoxy)-4,4-dicyclohexyl-4H-3,1-benzoxazin-2-one and 4-cyclohexyl-thiophenol.
M.p.: 173°–175° C.,
Yield: 82.3% of theory.

EXAMPLE 41

6-[4-(4-Cyclohexyl-phenylmercapto)-butoxy]-4H-3,1-benzoxazin-2-one

Prepared analogously to Example 1 from 6-(4-chlorobutoxy)-4H-3,1-benzoxazin-2-one and 4-cyclohexyl-thiophenol.
M.p.: 134°–135° C.,
Yield: 60.3% of theory.

EXAMPLE 42

6-[4-(4-Acetamido-phenylmercapto)-butoxy]-4,4-dicyclohexyl-4H-3,1-benzoxazin-2-one Prepared analogously to Example 1 from 6-(4-chlorobutoxy)-4,4-dicyclohexyl-4H-3,1-benzoxazin-2-one and 4-acetamido-thiophenol.
M.p.: 115° C. (decomp.),
Yield: 96.8% of theory.

EXAMPLE 43

6-[4-(4-Acetamido-phenylmercapto)-butoxy]-4H-3,1-benzoxazin-2-one

Prepared analogously to Example 1 from 6-(4-chlorobutoxy)-4H-3,1-benzoxazin-2-one and 4-acetamido-thiophenol.
M.p.: 163°–164° C.,
Yield: 71.6% of theory.

EXAMPLE 44

6-[2-(3,4-Dichloro-phenylmercapto)-ethoxy]-4,4-dimethyl-4H-3,1-benzoxazin-2-one

Prepared analogously to Example 1 from 6-(2-chloroethoxy)-4,4-dimethyl-4H-3,1-benzoxazin-2-one and 3,4-dichloro-thiophenol.
M.p.: 145°–146° C.,
Yield: 69.1% of theory.

EXAMPLE 45

6-[3-(3,4-Dichloro-phenylmercapto)-propoxy]-4,4-dimethyl-4H-3,1-benzoxazin-2-one Prepared analogously to Example 1 from 6-(3-chloropropoxy)-4,4-dimethyl-4H-3,1-benzoxazin-2-one and 3,4-dichloro-thiophenol.
M.p.: 115°–116° C.,
Yield: 88.9% of theory.

EXAMPLE 46

6-[3-(4-Cyclohexyl-phenylmercapto)-propoxy]-4,4-dimethyl-4H-3,1-benzoxazin-2-one Prepared analogously to Example 1 from 6-(3-chloropropoxy)-4,4-dimethyl-4H-3,1-benzoxazin-2-one and 4-cyclohexyl-thiophenol.
M.p.: 113°–114° C.,
Yield: 58.1% of theory.

EXAMPLE 47

6-[4-(3,4-Dimethyl-phenylmercapto)-butoxy]-4H-3,1-benzoxazin-2-one

Prepared analogously to Example 1 from 6-(4-chlorobutoxy)-4H-3,1-benzoxazin-2-one and 3,4-dimethyl-thiophenol.
M.p.: 124°–125° C.,
Yield: 73% of theory.

EXAMPLE 48

6-[5-(4-Cyclohexyl-phenylmercapto)-pentoxy]-4,4-dimethyl-4H-3,1-benzoxazin-2-one Prepared analogously to Example 1 from 6-(5-bromopentoxy)-4,4-dimethyl-4H-3,1-benzoxazin-2-one and 4-cyclohexyl-thiophenol.
M.p.: 108°–110° C.,
Yield: 62.6% of theory.

EXAMPLE 49

6-[5-(3,4-Dichloro-phenylmercapto)-pentoxy]-4,4-dimethyl-4H-3,1-benzoxazin-2-one Prepared analogously to Example 1 from 6-(5-bromopentoxy)-4,4-dimethyl-4H-3,1-benzoxazin-2-one and 3,4-dichloro-thiophenol.
M.p.: 110°–112° C.,
Yield: 81.3% of theory.

EXAMPLE 50

6-[4-tert.Butyl-phenylsulfinyl)-butoxy]-4,4-dimethyl-4H-3,1-benzoxazin-2-one

Prepared analogously to Example 2 from 6-[4-(4-tert.butyl-phenylmercapto)-butoxy]-4,4-dimethyl-4H-3,1-benzoxazin-2-one and hydrogen peroxide.
M.p.: 115° C.,
Yield: 53.8% of theory.

EXAMPLE 51

6-[4-(4-Acetamido-phenylsulfinyl)-butoxy]-4,4-dimethyl-4H-3,1-benzoxazin-2-one

Prepared analogously to Example 2 from 6-[4-(4-acetamido-phenylmercapto)-butoxy]-4,4-dimethyl-4H-3,1-benzoxazin-2-one and hydrogen peroxide.
M.p.: 180° C.,
Yield: 55.9% of theory.

EXAMPLE 52

6-(4-Phenylsulfinyl-butoxy)-4,4-dimethyl-4H-3,1-benzoxazin-2-one

Prepared analogously to Example 2 from 6-(4-phenylmercapto-butoxy)-4,4-dimethyl-4H-3,1-benzoxazin-2-one and hydrogen peroxide.
M.p.: 64°–66° C.,
Yield: 68.4% of theory.

EXAMPLE 53

6-[4-(3,4-Dichloro-phenylsulfinyl)-butoxy]-4,4-dimethyl-4H-3,1-benzoxazin-2-one

Prepared analogously to Example 2 from 6-[4-(3,4-dichloro-phenylmercapto)-butoxy]-4,4-dimethyl-4H-3,1-benzoxazin-2-one and hydrogen peroxide.
M.p.: 139°–140° C.,
Yield: 83.8% of theory.

EXAMPLE 54

6-[4-(4-Chlorophenylsulfinyl)-butoxy]-4,4-dimethyl-4H-3,1-benzoxazin-2-one

Prepared analogously to Example 2 from 6-[4-(4-chlorophenylmercapto)-butoxy]-4,4-dimethyl-4H-3,1-benzoxazin-2-one and hydrogen peroxide.
M.p.: 135°–136° C.,
Yield: 66.3% of theory.

EXAMPLE 55

6-[4-(4-Cyclohexyl-phenylsulfinyl)-butoxy]-4,4-dimethyl-4H-3,1-benzoxazin-2-one

Prepared analogously to Example 2 from 6-[4-(4-cyclohexyl-phenylmercapto)-butoxy]-4,4-dimethyl-4H-3,1-benzoxazin-2-one and hydrogen peroxide.
M.p.: 147°–148° C.,
Yield: 74.3% of theory.

EXAMPLE 56

6-[4-(4-Methyl-phenylsulfinyl)-butoxy]-4,4-dimethyl-4H-3,1benzoxazin-2-one

Prepared analogously to Example 2 from 6-[4-(4-methyl-phenylmercapto)-butoxy]-4,4-dimethyl-4H-3,1-benzoxazin-2-one and hydrogen peroxide.
M.p.: 124°–125° C.,
Yield: 76.0% of theory.

EXAMPLE 57

6-[4-(4-Fluoro-phenylsulfinyl)-butoxy]-4,4-dimethyl-4H-3,1-benzoxazin-2-one

Prepared analogously to Example 2 from 6-[4-(4-fluoro-phenylmercapto)-butoxy]-4,4-dimethyl-4H-3,1-benzoxazin-2-one and hydrogen peroxide.
M.p.: 118°–120° C.,
Yield: 79.2% of theory.

EXAMPLE 58

6-[4-(3,4-Dimethoxy-phenylsulfinyl)-butoxy]-4,4-dimethyl-4H-3,1-benzoxazin-2-one Prepared analogously to Example 2 from 6-[4-(3,4-dimethoxy-phenylmercapto)-butoxy]-4,4-dimethyl-4H-3,1-benzoxazin-2-one and hydrogen peroxide.
M.p.: 157°–158° C.,
Yield: 82.6% of theory.

EXAMPLE 59

6-[4-(4-Methoxy-phenylsulfinyl)-butoxy]-4,4-dimethyl-4H-3,1-benzoxazin-2-one

Prepared analogously to Example 2 from 6-[4-(4-methoxy-phenylmercapto)-butoxy]-4,4-dimethyl-4H-3,1-benzoxazin-2-one and hydrogen peroxide.
M.p.: 130°–133° C.,
Yield: 82.9% of theory.

EXAMPLE 60

6-[4-(4-Hydroxy-phenylsulfinyl)-butoxy]-4,4-dimethyl-4H-3,1-benzoxazin-2-one

Prepared analogously to Example 2 from 6-[4-(4-hydroxy-phenylmercapto)-butoxy]-4,4-dimethyl-4H-3,1-benzoxazin-2-one and hydrogen peroxide.
M.p.: 157°–160° C.,
Yield: 44.9% of theory.

EXAMPLE 61

6-[4-(4-Biphenylylsulfinyl)-butoxy]-4,4-dimethyl-4H-3,1-benzoxazin-2-one

Prepared analogously to Example 2 from 6-[4-(4-biphenylylmercapto)-butoxy]-4,4-dimethyl-4H-3,1-benzoxazin-2-one and hydrogen peroxide.
M.p.: 155°–157° C.,
Yield: 68.0% of theory.

EXAMPLE 62

6-[4-(3-Methoxy-phenylsulfinyl)-butoxy]-4,4-dimethyl-4H-3,1-benzoxazin-2-one

Prepared analogously to Example 2 from 6-[4-(3-methoxy-phenylmercapto)-butoxy]-4,4-dimethyl-4H-3,1-benzoxazin-2-one and hydrogen peroxide.
Oil, RF value: 0.55 [silica gel plate; chloroform/ethanol (9:1)],
Yield: 88.4% of theory.
$C_{21}H_{25}NO_5S$: (403.5) Calculated: C: 62.51, H: 6.24, N: 3.47, S: 7.95. Found: C: 62.31, H: 6.17, N: 3.33, S: 7.84.

EXAMPLE 63

6-[4-(3-Methyl-phenylsulfinyl)-butoxy]-4,4-dimethyl-4H-3,1-benzoxazin-2-one

Prepared analogously to Example 2 from 6-[4-(3-methyl-phenylmercapto)-butoxy]-4,4-dimethyl-4H-3,1-benzoxazin-2-one and hydrogen peroxide.
Oil, RF value: 0.3 [silica gel plate; chloroform/acetone (9:1)],
Yield: 87.1% of theory.
$C_{21}H_{25}NO_4S$: (387.5) Calculated: C: 65.09, H: 6.50, N: 3.61, S: 8.27. Found: C: 64.98, H: 6.65, N: 3.53, S: 8.30.

EXAMPLE 64

6-[4-(4-Amino-3,5-dibromo-phenylsulfinyl)-butoxy]-4,4-dimethyl-4H-3,1-benzoxazin-2-one Prepared analogously to Example 2 from 6-[4-(4-amino-3,5-dibromo-phenylmercapto)-butoxy]-4,4-dimethyl-4H-3,1-benzoxazin-2-one and hydrogen peroxide.
M.p.: 169°–172° C.,
Yield: 35.2% of theory.

EXAMPLE 65

6-[4-(3,5-Di-tert.butyl-4-hydroxy-phenylsulfinyl)-butoxy]-4,4-dimethyl-4H-3,1-benzoxazin-2-one Prepared analogously to Example 2 from 6-[4-(3,5-ditert.butyl-4-hydroxy-phenylmercapto)-butoxy]-4,4-dimethyl-4H-3,1-benzoxazin-2-one and hydrogen peroxide.
M.p.: 177°–179° C.,
Yield: 74.6% of theory.

EXAMPLE 66

6-[4-(4-Bromo-phenylsulfinyl)-butoxy]-4,4-dimethyl-4H-3,1-benzoxazin-2-one

Prepared analogously to Example 2, from 6-[4-(4-bromo-phenylmercapto)-butoxy]-4,4-dimethyl-4H-3,1-benzoxazin-2-one and hydrogen peroxide.
M.p.: 137°–138° C.,
Yield: 79.8% of theory.

EXAMPLE 67

6-[4-(4-Methyl-phenylsulfinyl)-butoxy]-4H-3,1-benzoxazin-2-one

Prepared analogously to Example 2 from 6-[4-(4-methyl-phenylmercapto)-butoxy]-4H-3,1-benzoxazin-2-one and hydrogen peroxide.
M.p.: 143°–144° C.,
Yield: 82.2% of theory.

EXAMPLE 68

6-[4-(4-Cyclohexyl-phenylsulfinyl)-butoxy]-4H-3,1-benzoxazin-2-one

Prepared analogously to Example 2 from 6-[4-(4-cyclohexyl-phenylmercapto)-butoxy]-4H-3,1-benzoxazin-2-one and hydrogen peroxide.
M.p.: 118°–119° C.,
Yield: 81.5% of theory.

EXAMPLE 69

6-[4-(4-Acetamido-phenylsulfinyl)-butoxy]-4H-3,1-benzoxazin-2-one

Prepared analogously to Example 2 from 6-[4-(4-acetamido-phenylmercapto)-butoxy]-4H-3,1-benzoxazin-2-one and hydrogen peroxide.
M.p.: 183°–184° C.,
Yield: 84.0% of theory.

EXAMPLE 70

6-[4-(3,4-Dimethyl-phenylsulfinyl)-butoxy]-4H-3,1-benzoxazin-2-one

Prepared analogously to Example 2 from 6-[4-(3,4-dimethyl-phenylmercapto)-butoxy]-4H-3,1-benzoxazin-2-one and hydrogen peroxide.
M.p.: 119°–120° C.,
Yield: 57.0% of theory.

EXAMPLE 71

6-(4-Phenylsulfinyl-butoxy)-4H-3,1-benzoxazin-2-one

Prepared analogously to Example 2 from 6-(4-phenylmercapto-butoxy)-4H-3,1-benzoxazin-2-one and hydrogen peroxide.
M.p.: 115°–116° C.,
Yield: 66.7% of theory.

EXAMPLE 72

6-[4-(3,4-Dichloro-phenylsulfinyl)-butoxy]-4H-3,1-benzoxazin-2-one

Prepared analogously to Example 2 from 6-[4-(3,4-dichlorophenylmercapto)-butoxy]-4H-3,1-benzoxazin-2-one and hydrogen peroxide.
M.p.: 169°–170° C.,
Yield: 91.8% of theory.

EXAMPLE 73

6-[4-(4-Chloro-phenylsulfinyl)-butoxy]-4H-3,1-benzoxazin-2-one

Prepared analogously to Example 2 from 6-[4-(4-chloro-phenylmercapto)-butoxy]-4H-3,1-benzoxazin-2-one and hydrogen peroxide.
M.p.: 169°–171° C.,
Yield: 86.0% of theory.

EXAMPLE 74

6-(4-Benzylsulfinyl-butoxy)-4,4-dimethyl-4H-3,1-benzoxazin-2-one

Prepared analogously to Example 2 from 6-(4-benzylmercapto-butoxy)-4,4-dimethyl-4H-3,1-benzoxazin-2-one and hydrogen peroxide.
M.p.: 122° C.,
Yield: 71.0% of theory.

EXAMPLE 75

6-(4-Methylsulfinyl-butoxy)-4,4-dimethyl-4H-3,1-benzoxazin-2-one

Prepared analogously to Example 2 from 6-(4-methylmercapto-butoxy)-4,4-dimethyl-4H-3,1-benzoxazin-2-one and hydrogen peroxide.
M.p.: 124°–126° C.,
Yield: 68.1% of theory.

EXAMPLE 76

6-(4-Cyclohexylsulfinyl-butoxy)-4,4-dimethyl-4H-3,1-benzoxazin-2-one

Prepared analogously to Example 2 from 6-(4-cyclohexylmercaptobutoxy)-4,4-dimethyl-4H-3,1-benzoxazin-2-one and hydrogen peroxide.
M.p.: 115° C.,
Yield: 76.9% of theory.

EXAMPLE 77

6-[4-(4-Acetamido-phenylsulfinyl)-butoxy]-4,4-dicyclohexyl-4H-3,1-benzoxazin-2-one Prepared analogously to Example 2 from 6-[4-(4-acetamido-phenylmercapto)-butoxy]-4,4-dicyclohexyl-4H-3,1-benzoxazin-2-one and hydrogen peroxide.
M.p.: 206°–207° C.,
Yield: 53.5% of theory.

EXAMPLE 78

6-[4-(4-Methyl-phenylsulfinyl)-butoxy]-4,4-dicyclohexyl-4H-3,1-benzoxazin-2-one

Prepared analogously to Example 2 from 6-[4-(4-methylphenylmercapto)-butoxy]-4,4-dicyclohexyl-4H-3,1-benzoxazin-2-one and hydrogen peroxide.
M.p.: 200°–201° C.,
Yield: 62.0% of theory.

EXAMPLE 79

6-[4-(4-Cyclohexyl-phenylsulfinyl)-butoxy]-4,4-dicyclohexyl-4H-3,1-benzoxazin-2-one Prepared analogously to Example 2 from 6-[4-(4-cyclohexyl-phenylmercapto)-butoxy]-4,4-dicyclohexyl-4H-3,1-benzoxazin-2-one and hydrogen peroxide.
M.p.: from 146° C. (decomp.),
Yield: 89.3% of theory.

EXAMPLE 80

6-[4-(3,4-Dichloro-phenylsulfinyl)-butoxy]-4,4-dicyclohexyl-4H-3,1-benzoxazin-2-one Prepared analogously to Example 2 from 6-[4-(3,4-dichloro-phenylmercapto)-butoxy]-4,4-dicyclohexyl-4H-3,1-benzoxazin-2-one and hydrogen peroxide.
M.p.: 186°–187° C.,
Yield: 49.2% of theory.

EXAMPLE 81

6-[4-(4-Methyl-phenylsulfinyl)-butoxy]-4,4-di-n-hexyl-4H-3,1-benzoxazin-2-one

Prepared analogously to Example 2 from 6-[4-(4-methylphenylmercapto)-butoxy]-4,4-di-n-hexyl-4H-3,1-benzoxazin-2-one and hydrogen peroxide.
M.p.: 78°–79° C.,
Yield: 87.3% of theory.

EXAMPLE 82

6-[4-(4-Cyclohexyl-phenylsulfinyl)-butoxy]-4,4-di-n-hexyl-4H-3,1-benzoxazin-2-one Prepared analogously to Example 2 from 6-[4-(4-cyclohexyl-phenylmercapto)-butoxy]-4,4-di-n-hexyl-4H-3,1-benzoxazin-2-one and hydrogen peroxide.
M.p.: 72°–75° C.,
Yield: 71.4% of theory.

EXAMPLE 83

6-[4-(3,4-Dichloro-phenylsulfinyl)-butoxy]-4,4-di-n-hexyl-4H-3,1-benzoxazin-2-one Prepared analogously to Example 2 from 6-[4-(3,4-dichlorophenylmercapto)-butoxy]-4,4-di-n-hexyl-4H-3,1-benzoxazin-2-one and hydrogen peroxide.
M.p.: 83°–85° C.,
Yield: 71.7% of theory.

EXAMPLE 84

6-[4-(4-Acetamido-phenylsulfinyl)-butoxy]-4,4-di-n-hexyl-4H-3,1-benzoxazin-2-one Prepared analogously to Example 2 from 6-[4-(4-acetamido-phenylmercapto)-butoxy]-4,4-di-n-hexyl-4H-3,1-benzoxazin-2-one and hydrogen peroxide.
Oil, RF value: 0.48 [silica gel plate; chloroform/ethanol (9:1)],
Yield: 43.8% of theory.
$C_{32}H_{46}N_2O_5S$: (570.79) Calc.: C: 67.34, H: 8.12, N: 4.91, S: 5.62. Found: C: 67.52, H: 7.94, N: 4.95, S: 5.78.

EXAMPLE 85

6-[2-(3,4-Dichloro-phenylsulfinyl)-ethoxy]-4,4-dimethyl-4H-3,1-benzoxazin-2-one

Prepared analogously to Example 2 from 6-[2-(3,4-dichlorophenylmercapto)-ethoxy]-4,4-dimethyl-4H-3,1-benzoxazin-2-one and hydrogen peroxide.
M.p.: 200°–201° C.,
Yield: 63.3% of theory.

EXAMPLE 86

6-[3-(3,4-Dichloro-phenylsulfinyl)-propoxy]-4,4-dimethyl-4H-3,1-benzoxazin-2-one Prepared analogously to Example 2 from 6-[3-(3,4-dichloro-phenylmercapto)-propoxy]-4,4-dimethyl-4H-3,1-benzoxazin-2-one and hydrogen peroxide.
M.p.: 157°–158° C.,
Yield: 76.3% of theory.

EXAMPLE 87

6-[3-(4-Cyclohexyl-phenylsulfinyl)-propoxy]-4,4-dimethyl-4H-3,1-benzoxazin-2-one Prepared analogously to Example 2 from 6-[3-(4-cyclohexyl-phenylmercapto)-propoxy]-4,4-dimethyl-4H-3,1-benzoxazin-2-one and hydrogen peroxide.
Oil, RF value: 0.45 [silica gel plate; chloroform/ethanol (9:1)],
$C_{25}H_{31}NO_4S$: (441.59) Calc.: C: 68.00, H: 7.08, N: 3.17, S: 7.26. Found: C: 67.75, H: 7.01, N: 3.17, S: 7.13.

EXAMPLE 88

6-[5-(4-Cyclohexyl-phenylsulfinyl)-pentoxy]-4,4-dimethyl-4H-3,1-benzoxazin-2-one Prepared analogously to Example 2 from 6-[5-(4-cyclohexyl-phenylmercapto)-pentoxy]-4,4-dimethyl-4H-3,1-benzoxazin-2-one and hydrogen peroxide.
Oil, RF value: 0.45 [silica gel plate; chloroform/ethanol (9:1)],
Yield: 63.9% of theory.
$C_{27}H_{35}NO_4S$: (469.65) Calc.: C: 69.05, H: 7.51, N: 2.98, S: 6.83. Found: C: 70.26, H: 7.74, N: 2.91, S: 6.87.

EXAMPLE 89

6-[5-(3,4-Dichloro-phenylsulfinyl)-pentoxy]-4,4-dimethyl-4H-3,1-benzoxazin-2-one Prepared analogously to Example 2 from 6-[5-(3,4-dichlorophenylmercapto)-pentoxy]-4,4-dimethyl-4H-3,1-benzoxazin-2-one and hydrogen peroxide.
M.p.: 119°–120° C.,
Yield: 83.8% of theory.

EXAMPLE 90

6-[4-(3,4-Dimethoxy-phenylsulfoximino)-butoxy]-4,4-dimethyl-4H-3,1-benzoxazin-2-one Prepared analogously to Example 6 from 6-[4-(3,4-dimethoxy-phenylsulfinyl)-butoxy]-4,4-dimethyl-4H-3,1-benzoxazin-2-one and ethyl-O-mesitylenesulfonyl-acethydroxamate.
M.p.: 162°–163° C.,
Yield: 51.3% of theory.

EXAMPLE 91

6-[4-(4-Methoxy-phenylsulfoximino)-butoxy]-4,4-dimethyl-4H-3,1-benzoxazin-2-one

Prepared analogously to Example 6 from 6-[4-(4-methoxy-phenylsulfinyl)-butoxy]-4,4-dimethyl-4H-3,1-benzoxazin-2-one and ethyl O-mesitylenesulfonyl-acethydroxamate.
M.p.: 134°–140° C.,
Yield: 47.8% of theory.

EXAMPLE 92

6-[4-(4-Hydroxy-phenylsulfoximino)-butoxy]-4,4-dimethyl-4H-3,1-benzoxazin-2-one

Prepared analogously to Example 6 from 6-[4-(4-hydroxyphenylsulfinyl)-butoxy]-4,4-dimethyl-4H-3,1-benzoxazin-2-one and ethyl O-mesitylenesulfonyl-acethydroxamate.
M.p.: 182°–184° C.,
Yield: 28.4% of theory.

EXAMPLE 93

6-[4-(3-Methoxy-phenylsulfoximino)-butoxy]-4,4-dimethyl-4H-3,1-benzoxazin-2-one

Prepared analogously to Example 6 from 6-[4-(3-methoxy-phenylsulfinyl)-butoxy]-4,4-dimethyl-4H-3,1-benzoxazin-2-one and ethyl O-mesitylenesulfonyl-acethydroxamate.
M.p.: 102°–105° C.,
Yield: 31.9% of theory.

EXAMPLE 94

6-[4-(4-Biphenylylsulfoximino)-butoxy]-4,4-dimethyl-4H-3,1-benzoxazin-2-one

Prepared analogously to Example 6 from 6-[4-(4-biphenylylsulfinyl)-butoxy]-4,4-dimethyl-4H-3,1-benzoxazin-2-one and ethyl O-mesitylenesulfonyl-acethydroxamate.
M.p.: 184°–186° C.,
Yield: 68.5% of theory.

EXAMPLE 95

6-[4-(4-Amino-3,5-dibromo-phenylsulfoximino)-butoxy]-4,4-dimethyl-4H-3,1-benzoxazin-2-one Prepared analogously to Example 6 from 6-[4-(4-amino-3,5-dibromophenylsulfinyl)-butoxy]-4,4-dimethyl-4H-3,1-benzoxazin-2-one and ethyl O-mesitylenesulfonyl-acethydroxamate.
M.p.: 206°–208° C.,
Yield: 73.8% of theory.

EXAMPLE 96

6-[4-(3,5-Di-tert.butyl-4-hydroxy-phenylsulfoximino)-butoxy]-4,4-dimethyl-4H-3,1-benzoxazin-2-one Prepared analogously to Example 6 from 6-[4-(3,5-di-tert.butyl-4-hydroxy-phenylsulfinyl)-butoxy]-4,4-dimethyl-4H-3,1-benzoxazin-2-one and ethyl O-mesitylenesulfonyl-acethydroxamate.
M.P.: 176°–178° C.,
Yield: 65.8% of theory.

EXAMPLE 97

6-[4-(3-Methyl-phenylsulfoximino)-butoxy]-4,4-dimethyl-4H-3,1-benzoxazin-2-one

Prepared analogously to Example 6 from 6-[4-(3-methyl-phenylsulfinyl)-butoxy]-4,4-dimethyl-4H-3,1-benzoxazin-2-one and ethyl O-mesitylenesulfonyl-acethydroxamate.
M.p.: 118°–120° C.,
Yield: 33% of theory.

EXAMPLE 98

6-[4-(4-Fluoro-phenylsulfoximino)-butoxy]-4,4-dimethyl-4H-3,1-benzoxazin-2-one

Prepared analogously to Example 6 from 6-[4-(4-fluoro-phenylsulfinyl)-butoxy]-4,4-dimethyl-4H-3,1-benzoxazin-2-one and ethyl O-mesitylenesulfonyl-acethydroxamate.
M.p.: 136°–138° C.,
Yield: 30.8% of theory.

EXAMPLE 99

6-[4-(4-Bromo-phenylsulfoximino)-butoxy]-4,4-dimethyl-4H-3,1-benzoxazin-2-one

Prepared analogously to Example 6 from 6-[4-(4-bromo-phenylsulfinyl)-butoxy]-4,4-dimethyl-4H-3,1-benzoxazin-2-one and ethyl O-mesitylenesulfonyl-acethydroxamate.
M.p.: 155°–157° C.,
Yield: 50% of theory.

EXAMPLE 100

6-[4-(4-Bromo-3-methyl-phenylsulfoximino)-butoxy]-4,4-dimethyl-4H-3,1-benzoxazin-2-one Prepared analogously to Example 6 from 6-[4(4-bromo-3-methyl-phenylsulfinyl)-butoxy]-4,4-dimethyl-4H-3,1-benzoxazin-2-one and ethyl O-mesitylenesulfonyl-acethydroxamate.
M.p.: 153°–154° C.,
Yield: 63.6% of theory.

EXAMPLE 101

6-[4-(4-Cyclohexyl-phenylsulfoximino)-butoxy]-4,4-dimethyl-4H-3,1-benzoxazin-2-one Prepared analogously to Example 6 from 6-[4-(4-cyclohexyl-phenylsulfinyl)-butoxy]-4,4-dimethyl-4H-3,1-benzoxazin-2-one and ethyl O-mesitylenesulfonyl-acethydroxamate.
M.p.: 168°–169° C.,
Yield: 52.8% of theory.

EXAMPLE 102

6-[4-(4-Methyl-phenylsulfoximino)-butoxy]-4,4-dimethyl-4H-3,1-benzoxazin-2-one

Prepared analogously to Example 6 from 6-[4-(4-methyl-phenylsulfinyl)-butoxy]-4,4-dimethyl-4H-3,1-benzoxazin-2-one and ethyl O-mesitylenesulfonyl-acethydroxamate.
M.p.: 147°–148° C.,
Yield: 59.2% of theory.

EXAMPLE 103

6-(4-Phenylsulfoximino-butoxy)-4,4-dimethyl-4H-3,1-benzoxazin-2-one

Prepared analogously to Example 6 from 6-(4-phenylsulfinyl-butoxy)-4,4-dimethyl-4H-3,1-benzoxazin-2-one and ethyl O-mesitylenesulfonyl-acethydroxamate.
M.p.: 152° C.,
Yield: 71.7% of theory.

EXAMPLE 104

6-[4-(4-Chloro-phenylsulfoximino)-butoxy]-4,4-dimethyl-4H-3,1-benzoxazin-2-one

Prepared analogously to Example 6 from 6-[4-(4-chloro-phenylsulfinyl)-butoxy]-4,4-dimethyl-4H-3,1-benzoxazin-2-one and ethyl O-mesitylenesulfonyl-acethydroxamate.
M.p.: 132° C.,
Yield: 61.6% of theory.

EXAMPLE 105

6-[4-(4-tert.Butyl-phenylsulfoximino)-butoxy]-4,4-dimethyl-4H-3,1-benzoxazin-2-one Prepared analogously to Example 6 from 6-[4-(4-tert.butyl-phenylsulfinyl)-butoxy]-4,4-dimethyl-4H-3,1-benzoxazin-2-one and ethyl O-mesitylenesulfonyl-acethydroxamate.
M.p.: 187° C.,
Yield: 72% of theory.

EXAMPLE 106

6-[4-(4-Acetamido-phenylsulfoximino)-butoxy]-4,4-dimethyl-4H-3,1-benzoxazin-2-one Prepared analogously to Example 6 from 6-[4-(4-acetamido-phenylsulfinyl)-butoxy]-4,4-dimethyl-4H-3,1-benzoxazin-2-one and ethyl O-mesitylenesulfonyl-acethydroxamate.
M.p.: 185° C.,
Yield: 44% of theory.

EXAMPLE 107

6-[4-(4-Methyl-phenylsulfoximino)-butoxy]-4,4-di-n-hexyl-4H-3,1-benzoxazin-2-one Prepared analogously to Example 6 from 6-[4-(4-methyl-phenylsulfinyl)-butoxy]-4,4-di-n-hexyl-4H-3,1-benzoxazin-2-one and ethyl O-mesitylenesulfonyl-acethydroxamate.
M.p.: 89°–91° C.,
Yield: 87.5% of theory.

EXAMPLE 108

6-[4-(4-Cyclohexyl-phenylsulfoximino)-butoxy]-4,4-di-n-hexyl-4H-3,1-benzoxazin-2-one Prepared analogously to Example 6 from 6-[4-(4-cyclohexyl-phenylsulfinyl)-butoxy]-4,4-di-n-hexyl-4H-3,1-benzoxazin-2-one and ethyl O-mesitylenesulfonyl-acethydroxamate.
M.p.: 78°–80° C.,
Yield: 48.3% of theory.

EXAMPLE 109

6-[4-(3,4-Dichloro-phenylsulfoximino)-butoxy]-4,4-di-n-hexyl-4H-3,1-benzoxazin-2-one Prepared analogously to Example 6 from 6-[4-(3,4-dichloro-phenylsulfinyl)-butoxy]-4,4-di-n-hexyl-4H-3,1-benzoxazin-2-one and ethyl O-mesitylenesulfonyl-acethydroxamate.
M.p.: 106°–108° C.,
Yield: 66.9% of theory.

EXAMPLE 110

6-[4-(4-Acetamido-phenylsulfoximino)-butoxy]-4,4-di-n-hexyl-4H-3,1-benzoxazin-2-one Prepared analogously to Example 6 from 6-[4-(4-acetamido-phenylsulfinyl)-butoxy]-4,4-di-n-hexyl-4H-3,1-benzoxazin-2-one and ethyl O-mesitylenesulfonyl-acethydroxamate.
M.p.: 146°–148° C.,
Yield: 78% of theory.

EXAMPLE 111

6-[4-(4-Acetamido-phenylsulfoximino)-butoxy]-4,4-dicyclohexyl-4H-3,1-benzoxazin-2-one Prepared analogously to Example 6 from 6-[4-(4-acetamido-phenylsulfinyl)-butoxy]-4,4-dicyclohexyl-4H-3,1-benzoxazin-2-one and ethyl O-mesitylenesulfonyl-acethydroxamate.
M.p.: 149°–150° C.,
Yield: 54% of theory.

EXAMPLE 112

6-[4-(4-Methyl-phenylsulfoximino)-butoxy]-4,4-dicyclohexyl-4H-3,1-benzoxazin-2-one Prepared analogously to Example 6 from 6-[4-(4-methyl-phenylsulfinyl)-butoxy]-4,4-dicyclohexyl-4H-3,1-benzoxazin-2-one and ethyl O-mesitylenesulfonyl-acethydroxamate.
M.p.: 176°–177° C.,
Yield: 58.6% of theory.

EXAMPLE 113

6-[4-(4-Cyclohexyl-phenylsulfoximino)-butoxy]-4,4-dicyclohexyl-4H-3,1-benzoxazin-2-one Prepared analogously to Example 6 from 6-[4-(4-cyclohexyl-phenylsulfinyl)-butoxy]-4,4-dicyclohexyl-4H-3,1-benzoxazin-2-one and ethyl O-mesitylenesulfonyl-acethydroxamate.
M.p.: 219°–220° C.,
Yield: 73.2% of theory.

EXAMPLE 114

6-[4-(4-Methyl-phenylsulfoximino)-butoxy]-4H-3,1-benzoxazin-2-one

Prepared analogously to Example 6 from 6-[4-(4-methylphenylsulfinyl)-butoxy]-4H-3,1-benzoxazin-2-one and ethyl O-mesitylenesulfonyl-acethydroxamate.
M.p.: 153°–154° C.,
Yield: 60% of theory.

EXAMPLE 115

6-[4-(4-Cyclohexyl-phenylsulfoximino)-butoxy]-4H-3,1-benzoxazin-2-one

Prepared analogously to Example 6 from 6-[4-(4-cyclohexyl-phenylsulfinyl)-butoxy]-4H-3,1-benzoxazin-2-one and ethyl O-mesitylenesulfonyl-acethydroxamate.
M.p.: 187°–188° C.,
Yield: 65% of theory.

EXAMPLE 116

6-[4-(4-Acetamido-phenylsulfoximino)-butoxy]-4H-3,1-benzoxazin-2-one

Prepared analogously to Example 6 from 6-[4-(4-acetamidophenylsulfinyl)-butoxy]-4H-3,1-benzoxazin-2-one and ethyl O-mesitylenesulfonyl-acethydroxamate.
M.p.: 135°–137° C.,
Yield: 64.7% of theory.

EXAMPLE 117

6-[5-(3,4-Dichloro-phenylsulfoximino)-pentoxy]-4,4-dimethyl-4H-3,1-benzoxazin-2-one Prepared analogously to Example 6 from 6-[5-(3,4-dichloro-phenylsulfinyl)-pentoxy]-4,4-dimethyl-4H-3,1-benzoxazin-2-one and ethyl O-mesitylenesulfonyl-acethydroxamate.
M.p.: 169°–170° C.,
Yield: 85.7% of theory.

EXAMPLE 118

6-[5-(4-Cyclohexyl-phenylsulfoximino)-pentoxy]-4,4-dimethyl-4H-3,1-benzoxazin-2-one Prepared analogously to Example 6 from 6-[5-(4-cyclohexyl-phenylsulfinyl)-pentoxy]-4,4-dimethyl-4H-3,1-benzoxazin-2-one and ethyl O-mesitylenesulfonyl-acethydroxamate.
M.p.: 110°–111° C.,
Yield: 67.1% of theory.

EXAMPLE 119

6-[3-(3,4-Dichloro-phenylsulfoximino)-propoxy]-4,4-dimethyl-4H-3,1-benzoxazin-2-one Prepared analogously to Example 6 from 6-[3-(3,4-dichlorophenylsulfinyl)-propoxy]-4,4-dimethyl-4H-3,1-benzoxazin-2-one and ethyl O-mesitylenesulfonyl-acethydroxamate.
M.p.: 135°–136° C.,
Yield: 67.8% of theory.

EXAMPLE 120

6-[3-(4-Cyclohexyl-phenylsulfoximino)-propoxy]-4,4-dimethyl-4H-3,1-benzoxazin-2-one Prepared analogously to Example 6 from 6-[3-(4-cyclohexyl-phenylsulfinyl)-propoxy]-4,4-dimethyl-4H-3,1-benzoxazin-2-one and ethyl O-mesitylenesulfonyl-acethydroxamate.
M.p.: 175°–176° C.,
Yield: 50.3% of theory.

EXAMPLE 121

6-[2-(3,4-Dichloro-phenylsulfoximino)-ethoxy]-4,4-dimethyl-4H-3,1-benzoxazin-2-one Prepared analogously to Example 6 from 6-[2-(3,4-dichloro-phenylsulfinyl)-ethoxy]-4,4-dimethyl-4H-3,1-benzoxazin-2-one and ethyl O-mesitylenesulfonyl-acethydroxamate.
M.p.: 139°–140° C.,
Yield: 64% of theory.

EXAMPLE 122

6-[4-Cyclohexylsulfoximino-butoxy)-4,4-dimethyl]-4H-3,1-benzoxazin-2-one

Prepared analogously to Example 6 from 6-(4-cyclohexylsulfinylbutoxy)-4,4-dimethyl-4H-3,1-benzoxazin-2-one and ethyl O-mesitylenesulfonyl-acethydroxamate.
M.p.: 108°–110° C.,
Yield: 28% of theory.

EXAMPLE 123

6-[4-Benzylsulfoximino-butoxy]-4,4-dimethyl-4H-3,1-benzoxazin-2-one

Prepared analogously to Example 6 from 6-(4-benzylsulfinyl-butoxy)-4,4-dimethyl-4H-3,1-benzoxazin-2-one and ethyl O-mesitylenesulfonyl-acethydroxamate.
M.p.: 132°–138° C.,
Yield: 75° of theory.

EXAMPLE 124

6-(4-n-Octylsulfoximino-butoxy)-4,4-dimethyl-4H-3,1-benzoxazin-2-one

Prepared analogously to Example 6 from 6-(4-n-octylsulfinyl-butoxy)-4,4-dimethyl-4H-3,1-benzoxazin-2-one and ethyl O-mesitylenesulfonyl-acethydroxamate.
M.p.: 82° C.,
Yield: 73.2% of theory.

EXAMPLE 125

6-[4-(4-Chloro-phenylmercapto)-butoxy]-4H-3,1-benzoxazin-2-one

Prepared analogously to Example 5 from 6-hydroxy-4H-3,1-benzoxazin-2-one and 4-(4-chloro-phenylmercapto)-butylchloride (prepared from 4-(4-chlorophenylmercapto)-butanol and thionyl chloride).

Oil, RF value: 0.25 [silica gel; petroleum ether/cyclohexane (1:1)],
M.p.: 143°–144° C.,
Yield: 28 % of theory.

EXAMPLE 126

6-[4-(3,4-Dichloro-phenylmercapto)-butoxy]-4H-3,1-benzoxazin-2-one

Prepared analogously to Example 5 from 6-hydroxy-4H-3,1-benzoxazin-2-one and 4-(3,4-dichloro-phenylmercapto)-butylbromide (prepared from 3,4-dichloro-thiophenol and 1,4-dibromo-butane, B.p. $_{0.1\ mb}$: 153°–160° C.).
M.p.: 128°–129° C.,
Yield: 57% of theory.

EXAMPLE 127

6-(4-Phenylmercapto-butoxy)-4,4-dimethyl-4H-3,1-benzoxazin-2-one

Prepared analogously to Example 5 from 6-hydroxy-4,4-dimethyl-4H-3,1-benzoxazin-2-one and 4-phenylmercaptobutylbromide (B.p. $_{0.03\ mb}$: 95°–104° C.).
M.p.: 108°–109° C.,
Yield: 52.5% of theory.

EXAMPLE 128

6-[4-(3,4-Dichloro-phenylmercapto)-butoxy]-4,4-dimethyl-4H-3,1-benzoxazin-2-one

Prepared analogously to Example 5 from 6-hydroxy-4,4-dimethyl-4H-3,1-benzoxazin-2-one and 4-(3,4-dichloro-phenylmercapto)-butylbromide.
M.p.: 155°–156° C.,
Yield: 53% of theory.

EXAMPLE 129

6-[4-(4-Chlorophenylmercapto)-butoxy]-4,4-dimethyl-4H-3,1-benzoxazin-2-one

Prepared analogously to Example 5 from 6-hydroxy-4,4-dimethyl-4H-3,1-benzoxazin-2-one and 4-(4-chlorophenylmercapto)-butylchloride.
M.p.: 150°–151° C.,
Yield: 55.6% of theory.

EXAMPLE 130

6-[4-(3,4-Dimethyl-phenylsulfoximino)-butoxy]-4H-3,1-benzoxazin-2-one

Prepared analogously to Example 6 from 6-[4-(3,4-dimethyl-phenylsulfinyl)-butoxy]-4H-3,1-benzoxazin-2-one and ethyl O-mesitylenesulfonyl-acethydroxamate.
M.p.: 169°–170° C.,
Yield: 82.5% of theory.

EXAMPLE 131

6-[4-(3,4-Dimethyl-phenylsulfoximino)-butoxy]-4,4-dimethyl-4H-3,1-benzoxazin-2-one Prepared analogously to Example 6 from 6-[4-(3,4-dimethyl-phenylsulfinyl)-butoxy]-4,4-dimethyl-4H-3,1-benzoxazin-2-one and ethyl O-mesitylenesulfonyl-acethydroxamate.
M.p.: 162°–163° C.,
Yield: 70.4% of theory.

EXAMPLE 132

6-[4-(3,4-Dimethyl-phenylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 3,4-dimethylthiophenol.

M.p.: 122°–123° C.,
Yield: 75.3% of theory.

EXAMPLE 133

6-[6-(3,4-Dichloro-phenylmercapto)-hexyloxy]-4,4-dimethyl-4H-3,1-benzoxazin-2-one Prepared analogously to Example 1 from 6-(6-bromohexyloxy)-4,4-dimethyl-4H-3,1-benzoxazin-2-one and 3,4-dichlorothiophenol.
M.p.: 102°–103° C.,
Yield: 77.4% of theory.

EXAMPLE 134

6-[6-(3,4-Dimethoxy-phenylmercapto)-hexyloxy]-4,4-dimethyl-4H-3,1-benzoxazin-2-one Prepared analogously to Example 1 from 6-(6-bromohexyloxy)-4,4-dimethyl-4H-3,1-benzoxazin-2-one and 3,4-dimethoxythiophenol.
M.p.: 153°–154° C.,
Yield: 89.4% of theory.

EXAMPLE 135

6-(4-Phenylsulfonyl-butoxy)-4,4-dimethyl-B 4H-3,1-benzoxazin-2-one

Prepared analogously to Example 4 from 6-hydroxy-4,4-dimethyl-4H-3,1-benzoxazin-2-one and 4-phenylsulfonylbutylbromide (melting point: 57°–58° C.).
M.p.: 155°–156° C.,
Yield: 53.7% of theory.

EXAMPLE 136

6-[6-(3,4-Dichloro-phenylsulfoximino)-hexyloxy]-4,4-dimethyl-4H-3,1-benzoxazin-2-one Prepared analogously to Example 6 from 6-[6-(3,4-dichlorophenylsulfinyl)-hexyloxy]-4,4-dimethyl-4H-3,1-benzoxazin-2-one and ethyl O-mesitylenesulfonylacethydroxamate.
M.p.: 135°–136° C.,
Yield: 84.5% of theory.

EXAMPLE 137

6-[4-(3,4-Dichlorophenylmercapto)-butoxy]-4,4-dimethyl-4H-3,1-benzoxazin-2-one

Prepared analogously to Example 4 from 6-hydroxy-4,4-dimethyl-4H-3,1-benzoxazin-2-one and 4-(3,4-dichlorophenylmercapto)-butylbromide (B.p. 0.1 mb: 153°–160° C.).
M.p.: 152°–153° C.,
Yield: 63.4% of theory.

EXAMPLE 138

6-[4-(3,4-Dichlorophenylsulfinyl)-butoxy]-4-ethyl-4H-3,1-benzoxazin-2-one

Prepared analogously to Example 4 from 4-ethyl-6-hydroxy-4H-3,1-benzoxazin-2-one and 4-(3,4-dichlorophenylsulfinyl)butylbromide.
M.p.: 83°–84° C.,
Yield: 61.9% of theory.

EXAMPLE 139

6-[4-(3,4-Dichloro-phenylsulfinyl)-butoxy]-4-isopropyl-4H-3,1-benzoxazin-2-one

Prepared analogously to Example 4 from 6-hydroxy-4-isopropyl-4H-3,1-benzoxazin-2-one and 4-(3,4-dichloro-phenylsulfinyl)-butylbromide.

M.p.: 73°–75° C.,
Yield: 48.2% of theory.

EXAMPLE 140

6-[4-(3,4-Dichloro-phenylsulfoximino)-butoxy]-4-ethyl-4H-3,1-benzoxazin-2-one

Prepared analogously to Example 6 from 6-[4-(3,4-dichloro-phenylsulfinyl)-butoxy]-4-ethyl-4H-3,1-benzoxazin-2-one and ethyl O-mesitylenesulfonyl-acethydroxamate.
M.p.: 132°–133° C.,
Yield: 60% of theory.

EXAMPLE 141

6-[4-(3,4-Dichloro-N-p-toluolsulfonyl-phenylsulfoximino)butoxy]-4,4-dimethyl-4H-3,1-benzoxazin-2-one Prepared analogously to Example 12 from 6-[4-(3,4-dichloro-phenylsulfoximino)-butoxy]-4,4-dimethyl-4H-3,1-benzoxazin-2-one and p-toluenesulfonic acid chloride.
M.p.: 174°–175° C.,
Yield: 78.4% of theory.

EXAMPLE 142

6-[4-(3,4-Dichloro-N-benzoyl-phenylsulfoximino)-butoxy]-4,4-dimethyl-4H-3,1-benzoxazin-2-one Prepared analogously to Example 12 from 6-[4-(3,4-dichloro-phenylsulfoximino)-butoxy]-4,4-dimethyl-4H-3,1-benzoxazin-2-one and benzoyl chloride.
M.p.: 189°–190° C.,
Yield: 67.6% of theory.

EXAMPLE 143

6-[4-(3,4-Dimethoxy-N-acetyl-phenylsulfoximino)-butoxy]-4,4-dimethyl-4H-3,1-benzoxazin-2-one A solution of 1 gm (0.0022 mol) of 6-[4-(3,4-dimethoxyphenylsulfoximino)-butoxy]-4,4-dimethyl-4H-3,1-benzoxazin-2-one in 10 ml of glacial acetic acid is mixed with 1.5 ml of acetic anhydride and stirred for three hours at ambient temperature. After addition of ice water, the mixture is extracted with chloroform, the chloroform phase is washed with water and dried with sodium sulfate, the chloroform is distilled off, and the residue is recrystallized from ethyl acetate.
M.p.: 155°–157° C.,
Yield: 0.95 gm (88% of theory).

EXAMPLE 144

6-[4-(4-Phenyl-N-acetyl-phenylsulfoximino)-butoxy]-4,4-dimethyl-4H-3,1-benzoxazin-2-one Prepared analogously to Example 143 from 6-[4-(4-phenylphenylsulfoximino)-butoxy]-4,4-dimethyl-4H-3,1-benzoxazin-2-one and acetic anhydride.
M.p.: 106°–108° C.,
Yield: 94.7% of theory.

EXAMPLE 145

6-[4-(3,5-Di-tert.butyl-4-hydroxy-N-acetyl-phenylsulfoximino)butoxy]-4,4-dimethyl-4H-3,1-benzoxazin-2-one Prepared analogously to Example 143 from 6-[4-(3,5-ditert.butyl-4-hydroxy-phenylsulfoximino)-butoxy]-4,4-dimethyl-4H-3,1-benzoxazin-2-one and acetic anhydride.
M.p.: 206°–207° C.,

EXAMPLE 146

6-[4-(4-Amino-3,5-dibromo-N-acetyl-phenylsulfoximino)-butoxy]-4,4-dimethyl-4H-3,1-benzoxazin-2-one Prepared analogously to Example 143 from 6-[4-(4-amino-3,5-dibromo-phenylsulfoximino)-butoxy]-4,4-dimethyl-4H-3,1-benzoxazin-2-one and acetic anhydride.

M.p.: 198°–200° C.,
Yield: 86.2% of theory.

EXAMPLE 147

6-[4-(4-tert.Butyl-N-acetyl-phenylsulfoximino)-butoxy]-4,4-dimethyl-4H-3,1-benzoxazin-2-one Prepared analogously to Example 143 from 6-[4-(4-tert.butyl-phenylsulfoximino)-butoxy]-4,4-dimethyl-4H-3,1-benzoxazin-2-one and acetic anhydride.

M.p.: 235°–237° C.,
Yield: 92.9% of theory.

EXAMPLE 148

6-[4-(4-Methyl-N-acetyl-phenylsulfoximino)-butoxy]-4,4-dimethyl-4H-3,1-benzoxazin-2-one Prepared analogously to Example 143 from 6-[4-(4-methylphenylsulfoximino)-butoxy]-4H-3,1-benzoxazin-2-one and acetic anhydride.

M.p.: 109°–110° C.,
Yield: 83.6% of theory.

EXAMPLE 149

6-[4-(4-Bromo-3-methyl-N-acetyl-phenylsulfoximino)-butoxy]-4,4-dimethyl-4H-3,1-benzoxazin-2-one Prepared analogously to Example 143 from 6-[4-(4-bromo-3-methyl-phenylsulfoximino)-butoxy]-4,4-dimethyl-4H-3,1-benzoxazin-2-one and acetic anhydride.

M.p.: 152°–154° C.,
Yield: 85.5% of theory.

EXAMPLE 150

6-[4-(3,4-Dichloro-N-acetyl-phenylsulfoximino)-butoxy]-4,4-dimethyl-4H-3,1-benzoxazin-2-one Prepared analogously to Example 143 from 6-[4-(3,4-dichlorophenyl-sulfoximino)-butoxy]-4,4-dimethyl-4H-3,1-benzoxazin-2-one and acetic anhydride.

M.p.: 156°–158° C.,
Yield: 91.3% of theory.

EXAMPLE 151

6-[4-(N-Acetyl-phenylsulfoximino)-butoxy]-4,4-dimethyl-4H-3,1-benzoxazin-2-one

Prepared analogously to Example 143 from 6-(4-phenylsulfoximinobutoxy)-4,4-dimethyl-4H-3,1-benzoxazin-2-one and acetic anhydride.

M.p.: 112°–114° C.,
Yield: 89.2% of theory.

EXAMPLE 152

6-[4-(4-Chloro-N-acetyl-phenylsulfoximino)-butoxy]-4,4-dimethyl-4H-3,1-benzoxazin-2-one Prepared analogously to Example 143 from 6-[4-(4-chlorophenylsulfoximino)-butoxy]-4,4-dimethyl-4H-3,1-benzoxazin-2-one and acetic anhydride.

M.p.: 120°–122° C.,
Yield: 86.9% of theory.

EXAMPLE 153

6-[4-(4-Methyl-N-acetyl-phenylsulfoximino)-butoxy]-4,4-di-n-hexyl-4H-3,1-benzoxazin-2-one Prepared analogously to Example 143 from 6-[4-(4-methylphenylsulfoximino)-butoxy]-4,4-di-n-hexyl-4H-3,1-benzoxazin-2-one and acetic anhydride.

Oil, RF value: 0.4 [silica gel plate; chloroform/acetone (9:1)],
Yield: 98.9% of theory.
$C_{33}H_{48}N_2O_5S$: (584.82) Calc.: C: 67.78, H: 8.27, S: 5.48. Found: C: 67.89, H: 8.31, S: 5.60.

EXAMPLE 154

6-[4-(4-Cyclohexyl-N-acetyl-phenylsulfoximino)-butoxy]-4,4-di-n-hexyl-4H-3,1-benzoxazin-2-one Prepared analogously to Example 143 from 6-[4-(4-cyclohexyl-phenylsulfoximino)-butoxy]-4,4-di-n-hexyl-4H-3,1-benzoxazin-2-one and acetic anhydride.

M.p.: 134°–136° C.,
Yield: 81.9% of theory.

EXAMPLE 155

6-[4-(3,4-Dichloro-N-acetyl-phenylsulfoximino)-butoxy]-4,4-di-n-hexyl-4H-3,1-benzoxazin-2-one Prepared analogously to Example 143 from 6-[4-(3,4-dichloro-phenylsulfoximino)-butoxy]-4,4-di-n-hexyl-4H-3,1-benzoxazin-2-one and acetic anhydride.

Oil, RF value: 0.54 [silica gel plate; chloroform/acetone (9:1)],
Yield: 68.8% of theory.
$C_{32}H_{44}Cl_2N_2O_5S$: (639.70) Calc.: C: 60.08, H: 6.93, Cl: 11.08, S: 5.01. Found: C: 59.87, H: 7.13, Cl: 11.20, S: 4.95.

EXAMPLE 156

6-[4-(4-Acetamido-N-acetyl-phenylsulfoximino)-butoxy]-4,4-di-n-hexyl-4H-3,1-benzoxazin-2-one Prepared analogously to Example 143 from 6-[4-(4-acetamido-phenylsulfoximino)-butoxy]-4,4-di-n-hexyl-4H-3,1-benzoxazin-2-one and acetic anhydride.

M.p.: 122°–124° C.,
Yield: 83.6% of theory.

EXAMPLE 157

6-[4-(4-Acetamido-N-acetyl-phenylsulfoximino)-butoxy]-4,4-dicyclohexyl-4H-3,1-benzoxazin-2-one Prepared analogously to Example 143 from 6-[4-(4-acetamido-phenylsulfoximino)-butoxy]-4,4-dicyclohexyl-4H-3,1-benzoxazin-2-one and acetic anhydride.

M.p.: 146° C. (decomp.),
Yield: 78.3% of theory.

EXAMPLE 158

6-[4-(4-Methyl-N-acetyl-phenylsulfoximino)-butoxy]-4,4-dicyclohexyl-4H-3,1-benzoxazin-2-one Prepared analogously to Example 143 from 6-[4-(4-methylphenylsulfoximino)-butoxy]-4,4-dicyclohexyl-4H-3,1-benzoxazin-2-one and acetic anhydride.

M.p.: 148°–149° C.,
Yield: 78.9% of theory.

EXAMPLE 159

6-[4-(4-Acetamido-N-acetyl-phenylsulfoximino)-butoxy]-4H-3,1-benzoxazin-2-one

Prepared analogously to Example 143 from 6-[4-(4-acetamido-phenylsulfoximino)-butoxy]-4H-3,1-benzoxazin-2-one and acetic anhydride.
M.p.: 200°–201° C.,
Yield: 73.7% of theory.

EXAMPLE 160

6-[4-(4-Methyl-N-acetyl-phenylsulfoximino)-butoxy]-4H-3,1-benzoxazin-2-one

Prepared analogously to Example 143 from 6-[4-(4-methylphenylsulfoximino)-butoxy]-4H-3,1-benzoxazin-2-one and acetic anhydride.
Oil, RF value: 0.62 [silica gel plate; chloroform/ethyl acetate (9:1)],
Yield: 45% of theory.

EXAMPLE 161

6-[4-(4-Cyclohexyl-N-acetyl-phenylsulfoximino)-butoxy]-4H-3,1-benzoxazin-2-one

Prepared analogously to Example 143 from 6-[4-(4-cyclohexyl-phenylsulfoximino)-butoxy]-4H-3,1-benzoxazin-2-one and acetic anhydride.
M.p.: 124°–125° C.,
Yield: 86.8% of theory.

EXAMPLE 162

6-[4-(4-Cyclohexyl-N-acetyl-phenylsulfoximino)-butoxy]-4,4-dicyclohexyl-4H-3,1-benzoxazin-2-one Prepared analogously to Example 143 from 6-[4-(4-cyclohexyl-phenylsulfoximino)-butoxy]-4,4-dicyclohexyl-4H-3,1-benzoxazin-2-one and acetic anhydride.
M.p.: 130° C.,
Yield: 70.2% of theory.

EXAMPLE 163

6-[5-(3,4-Dichloro-N-acetyl-phenylsulfoximino)-pentoxy]-4,4-dimethyl-4H-3,1-benzoxazin-2-one Prepared analogously to Example 143 from 6-[5-(3,4-dichloro-phenylsulfoximino)-pentoxy]-4,4-dimethyl-4H-3,1-benzoxazin-2-one and acetic anhydride.
M.p.: 126°–128° C.,
Yield: 50.6% of theory.

EXAMPLE 164

6-[5-(4-Cyclohexyl-N-acetyl-phenylsulfoximino)-pentoxy]-4,4-dimethyl-4H-3,1-benzoxazin-2-one Prepared analogously to Example 143 from 6-[5-(4-cyclohexyl-phenyl-sulfoximino)-pentoxy]-4,4-dimethyl-4H-3,1-benzoxazin-2-one and acetic anhydride.
M.p.: 95°–96° C.,
Yield: 83.5% of theory.

EXAMPLE 165

6-[3-(4-Cyclohexyl-N-acetyl-phenylsulfoximino)-propoxy]-4,4-dimethyl-4H-3,1-benzoxazin-2-one Prepared analogously to Example 143 from 6-[3-(4-cyclohexyl-phenyl-sulfoximino)-propoxy]-4,4-dimethyl-4H-3,1-benzoxazin-2-one and acetic anhydride.
M.p.: 114°–115° C.,
Yield: 94.2% of theory.

EXAMPLE 166

6-[3-(3,4-Dichloro-N-acetyl-phenylsulfoximino)-propoxy]-4,4-dimethyl-4H-3,1-benzoxazin-2-one Prepared analogously to Example 143 from 6-[3-(3,4-dichloro-phenylsulfoximino)-propoxy]-4,4-dimethyl-4H-3,1-benzoxazin-2-one and acetic anhydride.
M.p.: 198°–200° C.,
Yield: 81.2% of theory.

EXAMPLE 167

6-[2-(3,4-Dichloro-N-acetyl-phenylsulfoximino)-ethoxy]-4,4-dimethyl-4H-3,1-benzoxazin-2-one Prepared analogously to Example 143 from 6-[2-(3,4-dichloro-phenylsulfoximino)-ethoxy]-4,4-dimethyl-4H-3,1-benzoxazin-2-one and acetic anhydride.
M.p.: 154°–155° C.,
Yield: 81.2% of theory.

EXAMPLE 168

6-[4-(3,4-Dimethyl-phenylsulfinyl)-butoxy]-4,4-dimethyl-4H-3,1-benzoxazin-2-one

Prepared analogously to Example 2 from 6-[4-(3,4-dimethyl-phenylmercapto)-butoxy]-4,4-dimethyl-4H-3,1-benzoxazin-2-one and hydrogen peroxide.
M.p.: 131°–132° C.,
Yield: 83.3% of theory.

EXAMPLE 169

6-[6-(3,4-Dichloro-phenylsulfinyl)-hexyloxy]-4,4-dimethyl-4H-3,1-benzoxazin-2-one Prepared analogously to Example 2 from 6-[6-(3,4-dichloro-phenylmercapto)-hexyloxy]-4,4-dimethyl-4H-3,1-benzoxazin-2-one and hydrogen peroxide.
M.p.: 156°–158° C.,
Yield: 71.5% of theory.

EXAMPLE 170

6-[6-(3,4-Dimethoxy-phenylsulfinyl)-hexyloxy]-4,4-dimethyl-4H-3,1-benzoxazin-2-one Prepared analogously to Example 2 from 6-[6-(3,4-dimethoxy-phenylmercapto)-hexyloxy]-4,4-dimethyl-4H-3,1-benzoxazin-2-one and hydrogen peroxide.
M.p.: 131°–132° C.,
Yield: 61.0% of theory.

EXAMPLE 171

6-[4-(3,4-Dimethyl-N-acetyl-phenylsulfoximino)-butoxy]-4H-3,1-benzoxazin-2-one

Prepared analogously to Example 143 from 6-[4-(3,4-dimethyl-phenyl-sulfoximino)-butoxy]-4H-3,1-benzoxazin-2-one and acetic anhydride.
Resin, RF value: 0.7 [silica gel plate; chloroform/ethanol (9:1)],
Yield: 90.2% of theory.
$C_{22}H_{26}N_2O_5S$: (430.53) Calc.: C: 61.38, H: 6.09, N: 6.51, S: 7.45. Found: C: 61.79, H: 6.32, N: 6.24, S: 7.38.

EXAMPLE 172

6-[4-(3,4-Dimethyl-N-acetyl-phenylsulfoximino)-butoxy]-4,4-dimethyl-4H-3,1-benzoxazin-2-one Prepared analogously to Example 143 from 6-[4-(3,4-dimethyl-phenyl-sulfoximino)-butoxy]-4,4-dimethyl-4H-3,1-benzoxazin-2-one and acetic anhydride.
M.p.: 146° C.,

EXAMPLE 173

6-[6-(3,4-Dimethoxy-phenylsulfoximino)-hexyloxy]-4,4-dimethyl-4H-3,1-benzoxazin-2-one Prepared analogously to Example 6 from 6-[6-(3,4-dimethoxy-phenylsulfinyl)-hexyloxy]-4,4-dimethyl-4H-3,1-benzoxazin-2-one and ethyl O-mesitylenesulfonyl-acethydroxamate.

M.p.: 108°–109° C.,
Yield: 83.9% of theory.

EXAMPLE 174

6-[3-(3,4-Dichloro-phenylmercapto)-propoxy]-4-isopropyl-4H-3,1-benzoxazin-2-one

Prepared analogously to Example 1 from 6-(3-chloropropoxy)-4-isopropyl-4H-3,1-benzoxazin-2-one and 3,4-dichloro-thiophenol.

M.p.: 109°–111° C.,
Yield: 75.5% of theory.

EXAMPLE 175

4-Isopropyl-6-[3-(3,4-dimethoxy-phenylmercapto)-propoxy]-4H-3,1-benzoxazin-2-one Prepared analogously to Example 1 from 6-(3-chloropropoxy)-4-isopropyl-4H-3,1-benzoxazin-2-one and 3,4-dimethoxy-thiophenol.

M.p.: 102–103° C.,
Yield: 84.2% of theory.

EXAMPLE 176

6-[4-(3,4-Dichloro-N-acetyl-phenylsulfoximino)-butoxy]-4-ethyl-4H-3,1-benzoxazin-2-one Prepared analogously to Example 143 from 6-[4-(3,4-dichloro-phenylsulfoximino)-butoxy]-4-ethyl-4H-3,1-benzoxazin-2-one and acetic anhydride.

M.p.: 156°–158° C.,
Yield: 87.3% of theory.

EXAMPLE 177

6-[3-(3,4-Dichloro-phenylsulfinyl)-propoxy]-4-isopropyl-4H-3,1-benzoxazin-2-one

Prepared analogously to Example 2 from 6-[3-(3,4-dichloro-phenylmercapto)-propoxy]-4-isopropyl-4H-3,1-benzoxazin-2-one and hydrogen peroxide.

M.p.: 58°–60° C.,
Yield: 83.3% of theory.

EXAMPLE 178

6-[3-(3,4-Dimethoxy-phenylsulfinyl)-propoxy]-4-isopropyl-4H-3,1-benzoxazin-2-one Prepared analogously to Example 2 from 6-[3-(3,4-dimethoxy-phenylmercapto)-propoxy]-4-isopropyl-4H-3,1-benzoxazin-2-one and hydrogen peroxide.

M.p.: 58°–60° C.,
Yield: 91.1% of theory.

EXAMPLE 179

6-[6-(3,4-Dichloro-N-acetyl-phenylsulfoximino)-hexyloxy]-4,4-dimethyl-4H-3,1-benzoxazin-2-one Prepared analogously to Example 143 from 6-[6-(3,4-dichloro-phenylsulfoximino)-hexyloxy]-4,4-dimethyl-4H-3,1-benzoxazin-2-one and acetic anhydride.

Oil, RF value: 0.64 [silica gel plate; chloroform/ethanol (9:1)],
Yield: 83.1% of theory.
$C_{24}H_{28}Cl_2N_2O_5S$: (527.48) Calc.: C: 54.65, H: 5.35, S: 6.08. Found: C: 54.30, H: 5.34, S: 6.06.

EXAMPLE 180

6-[4-(3,4-Dichloro-phenylsulfoximino)-butoxy]-4-isopropyl-4H-3,1-benzoxazin-2-one Prepared analogously to Example 6 from 6-[4-(3,4-dichloro-phenylsulfinyl)-butoxy]-4-isopropyl-4H-3,1-benzoxazin-2-one and ethyl O-mesitylenesulfonyl-acethydroxamate.

M.p.: 123°–125° C.,
Yield: 47.7% of theory.

EXAMPLE 181

6-[6-(3,4-Dimethoxy-N-acetyl-phenylsulfoximino)-hexyloxy]-4,4-dimethyl-4H-3,1-benzoxazin-2-one Prepared analogously to Example 143 from 6-[6-(3,4-dimethoxy-phenylsulfoximino)-hexyloxy]-4,4-dimethyl-4H-3,1-benzoxazin-2-one and acetic anhydride.

Oil, RF value: 0.65 [silica gel plate; chloroform/ethanol (9:1)],
Yield: 83.5% of theory.
$C_{26}H_{34}N_2O_7S$: (518.63) Calc.: C: 60.21, H: 6.61, S: 6.18. Found: C: 59.90, H: 6.59, S: 6.13.

EXAMPLE 182

6-[4-(3,4-Dichloro-phenylsulfoximino)-butoxy]-4,4-dimethyl-4H-3,1-benzoxazin-2-one An amount of 3.3 gm (0.0075 mol) of 6-[4-(3,4-dichlorophenyl-sulfinyl)-butoxy]-4,4-dimethyl-4H-3,1-benzoxazin-2-one is stirred into 50 ml of polyphosphoric acid at 45° C. After it has virtually all dissolved, 0.65 gm (0.01 mol) of sodium azide are gradually added thereto over a period of 30 minutes. A slight development of nitrogen gas can be observed. The beige, creamy-foamy mass is stirred for three hours at 45° to 50° C., and then 150 gm of ice are added. The resultant cloudy solution is adjusted to a pH of 8 with concentrated ammonia, and the resinous product precipitated is extracted with chloroform. The oily evaporation residue is recrystallized from ethyl acetate/diisopropyl ether. White crystals are obtained.

M.p.: 166°–167° C.,
Yield: 2.0 gm (58.6% of theory).

EXAMPLE 183

6-[4-(3,4-Dichloro-phenylsulfimino)-butoxy]-4,4-dimethyl-4H-3,1-benzoxazin-2-one Prepared analogously to Example 6 from 6-[4-(3,4-dichloro-phenylmercapto)-butoxy]-4,4-dimethyl-4H-3,1-benzoxazin-2-one and ethyl O-mesitylenesulfonyl-acethydroxamate.

M.p.: 165°–166° C.,
Yield: 10% of theory.

EXAMPLE 184

6-[3-(3,4-Dimethoxy-phenylsulfoximino)-propoxy]-4-isopropyl-4H-3,1-benzoxazin-2-one Prepared analogously to Example 6 from 6-[3-(3,4-dimethoxy-phenylsulfinyl)-propoxy]-4-isopropyl-4H-3,1-benzoxazin-2-one and ethyl O-mesitylenesulfonyl-acethydroxamate.

M.p.: 123°–125° C.,
Yield: 77.3% of theory.

EXAMPLE 185

6-[4-(3,4-Dichloro-N-p-toluenesulfonyl-phenylsulfimino)-butoxy]-4,4-dimethyl-4H-3,1-benzoxazin-2-one A quantity of 4.26 gm (0.01 mol) of 6-[4-(3,4-dichlorophenylmercapto)-butoxy]-4,4-dimethyl-4H-3,1-benzoxazin-2-one is suspended in 50 ml of methanol, and enough chloroform is added to produce a clear solution (about 80 ml). Then, a solution of 3.38 gm (0.012 mol) of the sodium salt of N-chloro-p-toluenesulfonic acid in 30 ml of methanol is added thereto under stirring, and the mixture is left to stand for four hours at ambient temperature. About 1 ml of glacial acetic acid is added to the reaction solution, and the solvents are distilled off in a rotary evaporator (bath temperature: <20° C.). The viscous light-brown residue is purified over a silica gel column [eluant: ethyl acetate/cyclohexane (4:1)]. The uniform fractions are evaporated to dryness in the rotary evaporator, and the residue is recrystallized once from ethyl acetate/isopropanol.

M.p.: 162°-163° C.,
Yield: 2.0 gm (33.6% of theory).

EXAMPLE 186

6-[4-(3,4-Dichloro-N-p-toluenesulfonyl-phenylsulfoximino)-butoxy]-4,4-dimethyl-4H-3,1-benzoxazin-2-one An amount of 0.6 gm (0.001 mol) of 6-[4-(3,4-dichloro-N-p-toluenesulfonyl-phenylsulfimino)-butoxy]-4,4-dimethyl-4H-3,1-benzoxazin-2-one is suspended in 10 ml of methanol, mixed with 1 ml of 2N sodium hydroxide solution and 0.2 ml (0.002 mol) of 30% hydrogen peroxide, and refluxed for eight hours. A clear solution is obtained, which is evaporated to dryness when the reaction has ended. The residue is purified over a silica gel column (chloroform). The uniform fractions are concentrated by evaporation and recrystallized once from ethanol.

M.p.: 174°-175° C.,
Yield: 0.27 gm (44.1% of theory).

EXAMPLE 187

6-[3-(3,4-Dichloro-phenylsulfoximino)-propoxy]-4-isopropyl-4H-3,1-benzoxazin-2-one Prepared analogously to Example 6 from 6-[3-(3,4-dichloro-phenylsulfinyl)-propoxy]-4-isopropyl-4H-3,1-benzoxazin-2-one and ethyl O-mesitylenesulfonyl-acethydroxamate. Resin, RF value: 0.45 [silica gel plate; chloroform/ethanol (19:1)].

Yield: 43.7% of theory.
$C_{20}H_{22}Cl_2N_2O_4S$: (457.38) Calc.: C: 52.52, H: 4.85, S: 7.01. Found C: 52.49, H: 5.12, S: 6.63.

EXAMPLE 188

6-[3-(3,4-Dimethoxy-N-acetyl-phenylsulfoximino)-propoxy]-4-isopropyl-4H-3,1-benzoxazin-2-one Prepared analogously to Example 143 from 6-[3,4-dimethoxy-phenylsulfoximino)-propoxy]-4-isopropyl-4H-3,1-benzoxazin-2-one and acetic anhydride.

M.p.: 73°-75° C.,
Yield: 81.4% of theory.

EXAMPLE 189

6-[4-(4-Cyclohexyl-phenylmercapto)-butoxy]-4,4-diethyl-4H-3,1-benzoxazin-2-one

Prepared analogously to Example 1 from 6-(4-chlorobutoxy)-4,4-diethyl-4H-3,1-benzoxazin-2-one and 4-cyclohexyl-thiophenol.

M.p.: 85°-88° C.,
Yield: 69.1% of theory.

EXAMPLE 190

6-[4-(3,4-Dichloro-phenylmercapto)-butoxy]-4,4-diethyl-4H-3,1-benzoxazin-2-one

Prepared analogously to Example 1 from 6-(4-chlorobutoxy)-4,4-diethyl-4H-3,1-benzoxazin-2-one and 3,4-dichloro-thiophenol.

M.p.: 143°-145° C.,
Yield: 58.7% of theory.

EXAMPLE 191

6-(4-Phenylmercapto-butoxy)-4,4-diethyl-4H-3,1-benzoxazin-2-one

Prepared analogously to Example 1 from 6-(4-chlorobutoxy-4,4-diethyl-4H-3,1-benzoxazin-2-one and thiophenol.

M.p.: 104°-106° C.,
Yield: 69.8% of theory.

EXAMPLE 192

6-[4-(3,4-Dimethyl-phenylmercapto)-butoxy]-4,4-diethyl-4H-3,1-benzoxazin-2-one

Prepared analogously to Example 1 from 6-(4-chlorobutoxy)-4,4-diethyl-4H-3,1-benzoxazin-2-one and 3,4-dimethyl-thiophenol.

M.p.: 124°-125° C.,
Yield: 83.4% of theory.

EXAMPLE 193

6-[4-(3,4-Dimethoxy-phenylmercapto)-butoxy]-4,4-diethyl-4H-3,1-benzoxazin-2-one

Prepared analogously to Example 1 from 6-(4-chlorobutoxy)-4,4-diethyl-4H-3,1-benzoxazin-2-one and 3,4-dimethoxy-thiophenol.

M.p.: 110°-111° C.,
Yield: 72.6% of theory.

EXAMPLE 194

6-[4-(4-Acetamido-phenylmercapto)-butoxy]-4,4-diethyl-4H-3,1-benzoxazin-2-one

Prepared analogously to Example 1 from 6-(4-chlorobutoxy)-4,4-diethyl-4H-3,1-benzoxazin-2-one and 4-acetamido-thiophenol.

M.p.: 90°-92° C.,
Yield: 62.9% of theory.

EXAMPLE 195

6-[4-(3,4-Dichloro-phenylmercapto)-butoxy]-4-methyl-4H-3,1-benzoxazin-2-one

Prepared analogously to Example 1 from 6-(4-chlorobutoxy)-4-methyl-4H-3,1-benzoxazin-2-one and 3,4-dichloro-thiophenol.

M.p.: 117°-119° C.,
Yield: 50.5% of theory.

EXAMPLE 196

6-[4-(4-Methyl-phenylmercapto)-butoxy]-4-methyl-4H-3,1-benzoxazin-2-one

Prepared analogously to Example 1 from 6-(4-chlorobutoxy)-4-methyl-4H-3,1-benzoxazin-2-one and 4-methyl-thiophenol.
M.p.: 111°–113° C.,
Yield: 54.4% of theory.

EXAMPLE 197

6-[4-(4-Acetamino-phenylmercapto)-butoxy]-4-methyl-4H-3,1-benzoxazin-2-one

Prepared analogously to Example 1 from 6-(4-chlorobutoxy)-4-methyl-4H-3,1-benzoxazin-2-one and 4-acetamido-thiophenol.
M.p.: 122°–124° C.,
Yield: 44.2% of theory.

EXAMPLE 198

6-[4-(2-Benzothiazolylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 2-mercapto-benzothiazole.
M.p.: 183°–184° C.,
Yield: 56.3% of theory.

EXAMPLE 199

6-[4-(4,6-Dimethyl-2-pyrimidinylmercapto)-butoxy]-4,4-dimethyl-4H-3,1-benzoxazin-2-one Prepared analogously to Example 1 from 6-(4-chlorobutoxy)-4,4-dimethyl-4H-3,1-benzoxazin-2-one and 4,6-dimethyl-2-mercapto-pyrimidine.
M.p.: 125°–127° C.,
Yield: 65.9% of theory.

EXAMPLE 200

6-[4-(1-Oxido-2-pyridylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 2-mercapto-pyridine-1-oxide.
M.p.: 154°–156° C.,
Yield: 14.6% of theory.

EXAMPLE 201

6-[4-(1,2,4-Triazol-3-yl-mercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 3-mercapto-1,2,4-triazole.
M.p.: 181°–183° C.,
Yield: 42.2% of theory.

EXAMPLE 202

6-[4-(2-Pyrimidinylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 2-mercapto-pyrimidine.
M.p.: 142°–144° C.,
Yield: 53.9% of theory.

EXAMPLE 203

6-[4-(4-Pyridylmercapto)-butoxy]-4,4-dimethyl-4H-3,1-benzoxazin-2-one

Prepared analogously to Example 1 from 6-(4-chlorobutoxy)-4,4-dimethyl-4H-3,1-benzoxazin-2-one and 4-mercapto-pyridine.
M.p.: 153°–155° C.,
Yield: 64.2% of theory.

EXAMPLE 204

8-[4-(4-Cyclohexyl-phenylmercapto)-butoxy]-4,4-dimethyl-4H-3,1-benzoxazin-2-one

Prepared analogously to Example 1 from 8-(4-chlorobutoxy)-4,4-dimethyl-4H-3,1-benzoxazin-2-one and 4-cyclohexyl-thiophenol.
M.p.: 109°–110° C.,
Yield: 70.5% of theory.

EXAMPLE 205

8-[4-(3,4-Dichloro-phenylmercapto)-butoxy]-4,4-dimethyl-4H-3,1-benzoxazin-2-one

Prepared analogously to Example 1 from 8-(4-chlorobutoxy)-4,4-dimethyl-4H-3,1-benzoxazin-2-one and 3,4-dichloro-thiophenol.
M.p.: 137°–138° C.,
Yield: 74.5% of theory.

EXAMPLE 206

8-(4-Phenylmercapto-butoxy)-4,4-dimethyl-4H-3,1-benzoxazin-2-one

Prepared analogously to Example 1 from 8-(4-chlorobutoxy)-4,4-dimethyl-4H-3,1-benzoxazin-2-one and thiophenol.
M.p.: 98°–100° C.,
Yield: 87.9% of theory.

EXAMPLE 207

8-[4-(3,4-Dimethyl-phenylmercapto)-butoxy]-4,4-dimethyl-4H-3,1-benzoxazin-2-one

Prepared analogously to Example 1 from 8-(4-chlorobutoxy)-4,4-dimethyl-4H-3,1-benzoxazin-2-one and 3,4-dimethyl-thiophenol.
M.p.: 137°–139° C.,
Yield: 90.7% of theory.

EXAMPLE 208

8-[4-(3,4-Dimethoxy-phenylmercapto)-butoxy]-4,4-dimethyl-4H-3,1-benzoxazin-2-one Prepared analogously to Example 1 from 8-(4-chlorobutoxy)-4,4-dimethyl-4H-3,1-benzoxazin-2-one and 3,4-dimethoxy-thiophenol.
M.p.: 116°–117° C.,
Yield: 93.8% of theory.

EXAMPLE 209

8-[4-(4-Acetamido-phenylmercapto)-butoxy]-4,4-dimethyl-4H-3,1-benzoxazin-2-one

Prepared analogously to Example 1 from 8-(4-chlorobutoxy)-4,4-dimethyl-4H-3,1-benzoxazin-2-one and 4-acetamido-thiophenol.
M.p.: 166°–167° C.,
Yield: 63.6% of theory.

EXAMPLE 210

6-[4-(3,4-Dimethyl-phenylmercapto)-butoxy]-7-nitro-4,4-dimethyl-4H-3,1-benzoxazin-2-one Quantities of 9.1 gm (0.0234 mol) of 6-(4-methanesulfonyloxy-butoxy)-7-nitro-4,4-dimethyl-4H-3,1-benzoxazin-2-one and 3.5 gm (0.025 mol) 3,4-dimethyl-thiophenol are dissolved in 80 ml of dimethylformamide. Then, 6.9 gm (0.05 mol) of potassium carbonate and finally 4 ml of water are added, under stirring. The reaction mixture heats up briefly, and, after the heat effect has died away, the mixture is stirred for a further two hours at ambient temperature. After addition of ice water, the mixture is extracted with chloroform, the organic phase is washed with water and dried with sodium sulfate, and the solvent is distilled off in vacuo. The residue is purified over a silica gel column [eluant: chloroform/ethanol (40:1)], Oil, RF value: 0.4 [silica gel plate; chloroform/ethanol (9:1)], Yield: 7.6 gm (75.4% of theory).

$C_{22}H_{26}N_2O_5S$: (430.52) Calc.: C: 61.38, H: 6.09, N: 6.51, S: 7.45. Found: C: 61.10, H: 6.07, N: 6.24, S: 7.28.

EXAMPLE 211

6-[4-(4-Acetamido-phenylmercapto)-butoxy]-7-nitro-4,4-dimethyl-4H-3,1-benzoxazin-2-one Prepared analogously to Example 210 from 6-(4-methanesulfonyloxy-butoxy)-7-nitro-4,4-dimethyl-4H-3,1-benzoxazin-2-one and 4-acetamido-thiophenol.

M.p.: 203°–205° C.,
Yield: 69.2% of theory.

EXAMPLE 212

6-[4-(4-Chloro-phenylmercapto)-butoxy]-7-nitro-4,4-dimethyl-4H-3,1-benzoxazin-2-one Prepared analogously to Example 210 from 6-(4-methanesulfonyloxy-butoxy)-7-nitro-4,4-dimethyl-4H-3,1-benzoxazin-2-one and 4-chloro-thiophenol.

M.p.: 155°–156° C.,
Yield: 69.5% of theory.

EXAMPLE 213

6-[4-(2-Pyridylmercapto)-butoxy]-7-nitro-4,4-dimethyl-4H-3,1-benzoxazin-2-one

Prepared analogously to Example 210 from 6-(4-methanesulfonyloxy-butoxy)-7-nitro-4,4-dimethyl-4H-3,1-benzoxazin-2-one and 2-mercapto-pyridine.

M.p.: 98°–100° C.,
Yield: 59.3% of theory.

EXAMPLE 214

6-[4-(4-Methyl-phenylmercapto)-butoxy]-7-nitro-4,4-dimethyl-4H-3,1-benzoxazin-2-one Prepared analogously to Example 210 from 6-(4-methanesulfonyloxy-butoxy)-7-nitro-4,4-dimethyl-4H-3,1-benzoxazin-2-one and 4-methyl-thiophenol.

M.p.: 128°–129° C.,
Yield: 77.7% of theory.

EXAMPLE 215

6-[4-(3,4-Dimethoxy-phenylmercapto)-butoxy]-7-nitro-4,4-dimethyl-4H-3,1-benzoxazin-2-one Prepared analogously to Example 210 from 6-(4-methanesulfonyloxy-butoxy)-7-nitro-4,4-dimethyl-4H-3,1-benzoxazin-2-one and 3,4-dimethoxy-thiophenol.

M.p.: 115°–117° C.,
Yield: 82.5% of theory.

EXAMPLE 216

7-[4-(3,4-Dimethyl-phenylmercapto)-butoxy]-4,4-dimethyl-4H-3,1-benzoxazin-2-one

Prepared analogously to Example 210 from 6-(4-methanesulfonyloxy-butoxy)-4,4-dimethyl-4H-3,1-benzoxazin-2-one and 3,4-dimethyl-thiophenol.

M.p.: 120°–122° C.,
Yield: 84.5% of theory.

EXAMPLE 217

7-[4-(4-Acetamido-phenylmercapto)-butoxy]-4,4-dimethyl-4H-3,1-benzoxazin-2-one

Prepared analogously to Example 210 from 7-(4-methanesulfonyloxy-butoxy)-4,4-dimethyl-4H-3,1-benzoxazin-2-one and 4-acetamido-thiophenol.

M.p.: 162°–164° C.,
Yield: 97.7% of theory.

EXAMPLE 218

7-[4-(2-Pyridylmercapto)-butoxy]-4,4-dimethyl-4H-3,1-benzoxazin-2-one

Prepared analogously to Example 210 from 7-(4-methanesulfonyloxy-butoxy)-4,4-dimethyl-4H-3,1-benzoxazin-2-one and 2-mercapto-pyridine.

M.p.: 125°–127° C.,
Yield: 75.4% of theory.

EXAMPLE 219

7-[4-(4-Methyl-phenylmercapto)-butoxy]-4,4-dimethyl-4H-3,1-benzoxazin-2-one

Prepared analogously to Example 210 from 6-(4-methanesulfonyloxy-butoxy)-4,4-dimethyl-4H-3,1-benzoxazin-2-one and 4-methyl-thiophenol.

M.p.: 120°–122° C.,
Yield: 80.7% of theory.

EXAMPLE 220

7-[4-(4-Chloro-phenylmercapto)-butoxy)-4,4-dimethyl-4H-3,1-benzoxazin-2-one

Prepared analogously to Example 210 from 7-(4-methanesulfonyloxy-butoxy)-4,4-dimethyl-4H-3,1-benzoxazin-2-one and 4-chlorothiophenol.

M.p.: 117°–119° C.,
Yield: 86.7% of theory.

EXAMPLE 221

7-[4-(3,4-Dichloro-phenylmercapto)-butoxy]-4,4-dimethyl-4H-3,1-benzoxazin-2-one

Prepared analogously to Example 210 from 7-(4-methanesulfonyloxy-butoxy)-4,4-dimethyl-4H-3,1-benzoxazin-2-one and 3,4-dichloro-thiophenol.

M.p.: 104°–106° C.,
Yield: 79.7% of theory.

EXAMPLE 222

7-(4-Phenylmercapto-butoxy)-4,4-dimethyl-4H-3,1-benzoxazin-2-one

Prepared analogously to Example 210 from 7-(4-methanesulfonyloxy-butoxy)-4,4-dimethyl-4H-3,1-benzoxazin-2-one and thiophenol.
M.p.: 123°–125° C.,
Yield: 89.5% of theory.

EXAMPLE 223

7-[4-(3,4-Dimethoxy-phenylmercapto)-butoxy]-4,4-dimethyl-4H-3,1-benzoxazin-2-one Prepared analogously to Example 210 from 6-(4-methanesulfonyloxy-butoxy)-4,4-dimethyl-4H-3,1-benzoxazin-2-one and 3,4-dimethoxy-thiophenol.
Oil, RF value: 0.6 [silica gel plate; ethylene chloride/ethanol (9:1)],
Yield: 80.7% of theory.
$C_{22}H_{27}NO_5S$: (417.53) Calc.: C: 63.29, H: 6.52, N: 3.35. Found: C: 63.00, H: 6.54, N: 3.38.

EXAMPLE 224

7-[4-(3,4-Dichloro-phenylsulfinyl)-butoxy]-4,4-dimethyl-4H-3,1-benzoxazin-2-one

Prepared analogously to Example 2 from 7-[4-(3,4-dichloro-phenylmercapto)-butoxy]-4,4-dimethyl-4H-3,1-benzoxazin-2-one and hydrogen peroxide.
M.p.: 82°–84° C.,
Yield: 92.1% of theory.

EXAMPLE 225

7-(4-Phenylsulfinyl-butoxy)-4,4-dimethyl-4H-3,1-benzoxazin-2-one

Prepared analogously to Example 2 from 7-(4-phenylmercapto-butoxy)-4,4-dimethyl-4H-3,1-benzoxazin-2-one and hydrogen peroxide.
M.p.: 117°–119° C.,
Yield: 96.7% of theory.

EXAMPLE 226

7-[4-(3,4-Dimethyl-phenylsulfinyl)-butoxy]-4,4-dimethyl-4H-3,1-benzoxazin-2-one-hydrate Prepared analogously to Example 2 from 7-[4-(3,4-dimethyl-phenylmercapto)-butoxy]-4,4-dimethyl-4H-3,1-benzoxazin-2-one and hydrogen peroxide.
Oil, RF value: 0.6 [silica gel plate; ethylene chloride/ethanol (9:1)],
Yield: 95.5% of theory,
$C_{22}H_{29}NO_5S$: (419.54) Calc.: C: 62.98, H: 6.97, N: 3.34, S: 7.64. Found: C: 63.24, H: 6.85, N: 3.40, S: 7.64.

EXAMPLE 227

7-[4-(4-Acetamido-phenylsulfinyl)-butoxy]-4,4-dimethyl-4H-3,1-benzoxazin-2-one

Prepared analogously to Example 2 from 7-[4-(4-acetamido-phenylmercapto)-butoxy]-4,4-dimethyl-4H-3,1-benzoxazin-2-one and hydrogen peroxide.
M.p.: 145°–147° C.,
Yield: 77.8% of theory.

EXAMPLE 228

7-[4-(2-Pyridylsulfinyl)-butoxy]-4,4-dimethyl-4H-3,1-benzoxazin-2-one

Prepared analogously to Example 2 from 7-[4-(2-pyridylmercapto)-butoxy]-4,4-dimethyl-4H-3,1-benzoxazin-2-one and hydrogen peroxide.
M.p.: 153°–155° C.,
Yield: 64.9% of theory.

EXAMPLE 229

7-[4-(4-Methyl-phenylsulfinyl)-butoxy]-4,4-dimethyl-4H-3,1-benzoxazin-2-one

Prepared analogously to Example 2 from 7-[4-(4-methylphenylmercapto)-butoxy]-4,4-dimethyl-4H-3,1-benzoxazin-2-one and hydrogen peroxide.
M.p.: 128°–130° C.,
Yield: 94.4% of theory.

EXAMPLE 230

7-[4-(4-Chloro-phenylsulfinyl)-butoxy]-4,4-dimethyl-4H-3,1-benzoxazin-2-one

Prepared analogously to Example 2 from 7-[4-(4-chlorophenylmercapto)-butoxy]-4,4-dimethyl-4H-3,1-benzoxazin-2-one and hydrogen peroxide.
M.p.: 140°–142° C.,
Yield: 91.6% of theory.

EXAMPLE 231

7-[4-(3,4-Dimethoxy-phenylsulfinyl)-butoxy]-4,4-dimethyl-4H-3,1-benzoxazin-2-one Prepared analogously to Example 2 from 7-[4-(3,4-dimethoxy-phenylmercapto)-butoxy]-4,4-dimethyl-4H-3,1-benzoxazin-2-one and hydrogen peroxide.
Resin, RF value: 0.4 [silica gel plate; ethylene chloride/ethanol (9:1)],
Yield: 40.8% of theory.
$C_{22}H_{27}NO_6S$: (433.53) Calc.: C: 60.95, H: 6.28, N: 3.32, S: 7.40. Found: C: 60.70, H: 6.25, N: 3.03, S: 7.53.

EXAMPLE 232

8-[4-(4-Cyclohexyl-phenylsulfinyl)-butoxy]-4,4-dimethyl-4H-3,1-benzoxazin-2-one

Prepared analogously to Example 2 from 8-[4-(4-cyclohexyl-phenylmercapto)-butoxy]-4,4-dimethyl-4H-3,1-benzoxazin-2-one and hydrogen peroxide.
M.p.: 144°–145° C.,
Yield: 71.9% of theory.

EXAMPLE 233

8-[4-(3,4-Dichloro-phenylsulfinyl)-butoxy]-4,4-dimethyl-4H-3,1-benzoxazin-2-one

Prepared analogously to Example 2 from 8-[4-(3,4-dichloro-phenylmercapto-butoxy]-4,4-dimethyl-4H-3,1-benzoxazin-2-one and hydrogen peroxide.
M.p.: 113°–114° C.,
Yield: 81.0% of theory.

EXAMPLE 234

8-(4-Phenylsulfinyl-butoxy]-4,4-dimethyl-4H-3,1-benzoxazin-2-one

Prepared analogously to Example 2 from 8-(4-phenylmercapto-butoxy)-4,4-dimethyl-4H-3,1-benzoxazin-2-one and hydrogen peroxide.
M.p.: 162°–163° C., Yield: 91.6% of theory.

EXAMPLE 235

8-[4-(4-Acetamido-phenylsulfinyl)-butoxy]-4,4-dimethyl-4H-3,1-benzoxazin-2-one

Prepared analogously to Example 2 from 8-[4-(4-acetamidophenylmercapto)-butoxy]-4,4-dimethyl-4H-3,1-benzoxazin-2-one and hydrogen peroxide.
M.p.: 166°–167° C.,
Yield: 63.2% of theory.

EXAMPLE 236

8-[4-(3,4-Dimethyl-phenylsulfinyl)-butoxy]-4,4-dimethyl-4H-3,1-benzoxazin-2-one

Prepared analogously to Example 2 from 8-[4-(3,4-dimethyl-phenylmercapto)-butoxy]-4,4-dimethyl-4H-3,1-benzoxazin-2-one and hydrogen peroxide.
M.p.: 111°–112° C.,
Yield: 63.9% of theory.

EXAMPLE 237

8-[4-(3,4-Dimethoxy-phenylsulfinyl)-butoxy]-4,4-dimethyl-4H-3,1-benzoxazin-2-one Prepared analogously to Example 2 from 8-[4-(3,4-dimethoxy-phenylmercapto)-butoxy]-4,4-dimethyl-4H-3,1-benzoxazin-2-one and hydrogen peroxide.
M.p.: 102°–103° C.,
Yield: 90.2% of theory.

EXAMPLE 238

6-[4-(4-Cyclohexyl-phenylsulfinyl)-butoxy]-4,4-diethyl-4H-3,1-benzoxazin-2-one

Prepared analogously to Example 2 from 6-[4-(4-cyclohexyl-phenylmercapto)-butoxy]-4,4-diethyl-4H-3,1-benzoxazin-2-one and hydrogen peroxide.
M.p.: 168°–170° C.,
Yield: 82.7% of theory.

EXAMPLE 239

6-[4-(3,4-Dichloro-phenylsulfinyl)-butoxy]-4,4-diethyl-4H-3,1-benzoxazin-2-one

Prepared analogously to Example 2 from 6-[4-(3,4-dichloro-phenylmercapto)-butoxy]-4,4-diethyl-4H-3,1-benzoxazin-2-one and hydrogen peroxide.
M.p.: 91°–93° C.,
Yield: 70.9% of theory.

EXAMPLE 240

6-(4-Phenylsulfinyl-butoxy)-4,4-diethyl-4H-3,1-benzoxazin-2-one

Prepared analogously to Example 2 from 6-(4-phenylmercapto-butoxy)-4,4-diethyl-4H-3,1-benzoxazin-2-one and hydrogen peroxide.
Resin, RF value: 0.6 [silica gel plate; chloroform/ethanol (9:1)],
Yield: 94.3% of theory.
$C_{22}H_{27}NO_4S$: (401.53) Calc.: C: 65.81, H: 6.78, N: 3.49, S: 7.98. Found: C: 65.55, H: 6.75, N: 3.40, S: 7.71.

EXAMPLE 241

6-[4-(3-4-Dimethyl-phenylsulfinyl)-butoxy]-4,4-diethyl-4H-3,1-benzoxazin-2-one

Prepared analogously to Example 2 from 6-[4-(3,4-dimethyl-phenylmercapto)-butoxy]-4,4-diethyl-4H-3,1-benzoxazin-2-one and hydrogen peroxide.
M.p.: 137°–138° C.,
Yield: 83.1% of theory.

EXAMPLE 242

6-[4-(3,4-Dimethoxy-phenylsulfinyl)-butoxy]-4,4-diethyl-4H-3,1-benzoxazin-2-one

Prepared analogously to Example 2 from 6-[4-(3,4-dimethoxy-phenylmercapto)-butoxy]-4,4-diethyl-4H-3,1-benzoxazin-2-one and hydrogen peroxide.
M.p.: 161°–163° C.,
Yield: 87.7% of theory.

EXAMPLE 243

6-[4-(4-Acetamido-phenylsulfinyl)-butoxy]-4,4-diethyl-4H-3,1-benzoxazin-2-one

Prepared analogously to Example 2 from 6-[4-(4-acetamidophenylmercapto)-butoxy]-4,4-diethyl-4H-3,1-benzoxazin-2-one and hydrogen peroxide.
M.p.: 69°–70° C.,
Yield: 92.6% of theory.

EXAMPLE 244

6-[4-(4-Pyridylsulfinyl)-butoxy]-4,4-dimethyl-4H-3,1-benzoxazin-2-one

Prepared analogously to Example 2 from 6-[4-(4-pyridylmercapto)-butoxy]-4,4-dimethyl-4H-3,1-benzoxazin-2-one and hydrogen peroxide.
M.p.: 141°–143° C.,
Yield: 36.9% of theory.

EXAMPLE 245

6-[4-(4,6-Dimethyl-2-pyrimidinylsulfinyl)-butoxy]-4,4-dimethyl-4H-3,1-benzoxazin-2-one Prepared analogously to Example 2 from 6-[4-(4,6-dimethyl-2-pyrimidinylmercapto)-butoxy]-4,4-dimethyl-4H-3,1-benzoxazin-2-one and hydrogen peroxide.
Resin, RF value: 0.4 [silica gel plate; ethylene chloride/ethanol (9:1)],
Yield: 15.0% of theory.
$C_{20}H_{25}N_3O_4S$: (403.50) Calc.: C: 59.53, H: 6.25, S: 7.95. Found: C: 59.30, H: 5.99, S: 7.88.

EXAMPLE 246

6-[4-(3,4-Dichloro-phenylsulfinyl)-butoxy]-4-methyl-4H-3,1-benzoxazin-2-one

Prepared analogously to Example 2 from 6-[4-(3,4-dichloro-phenylmercapto)-butoxy]-4-methyl-4H-3,1-benzoxazin-2-one and hydrogen peroxide.
M.p.: 138°–139° C.,
Yield: 86.0% of theory.

EXAMPLE 247

6-[4-(4-Methyl-phenylsulfinyl)-butoxy]-4-methyl-4H-3,1-benzoxazin-2-one

Prepared analogously to Example 2 from 6-[4-(4-methylphenylmercapto)-butoxy]-4-methyl-4H-3,1-benzoxazin-2-one and hydrogen peroxide.
M.p.: 120°–121° C.,
Yield: 58.4% of theory.

EXAMPLE 248

6-[4-(4-Acetamido-phenylsulfinyl)-butoxy]-4-methyl-4H-3,1-benzoxazin-2-one

Prepared analogously to Example 2 from 6-[4-(4-acetamido-phenylmercapto)-butoxy]-4-methyl-4H-3,1-benzoxazin-2-one and hydrogen peroside.
M.p.: 124°–126° C.,
Yield: 60.4% of theory.

EXAMPLE 249

6-[4-(2-Benzothiazolylsulfonyl)-butoxy]-4,4-dimethyl-4H-3,1-benzoxazin-2-one

Prepared analogously to Example 3 from 6-[4-(2-benzothiazolylmercapto)-butoxy]-4,4-dimethyl-4H-3,1-benzoxazin-2-one and hydrogen peroxide/glacial acetic acid.
M.p.: 177°–179° C.,
Yield: 55.9% of theory.

EXAMPLE 250

6-[4-(1,2,4-Thiazolyl-3-sulfonyl)-butoxy]-4,4-dimethyl-4H-3,1-benzoxazin-2-one

Prepared analogously to Example 3 from 6-[4-(1,2,4-triazolyl-3-mercapto)-butoxy]-4,4-dimethyl-4H-3,1-benzoxazin-2-one and hydrogen peroxide/glacial acetic acid.
M.p.: 197°–199° C.,
Yield: 83.0% of theory.

EXAMPLE 251

6-[4-(2-Pyrimidinylsulfonyl)-butoxy]-4,4-dimethyl-4H-3,1-benzoxazin-2-one

Prepared analogously to Example 3 from 6-[4-(2-pyrimidinylmercapto)-butoxy]-4,4-dimethyl-4H-3,1-benzoxazin-2-one and hydrogen peroxide/glacial acetic acid.
M.p.: 184°–186° C.,
Yield: 69.0% of theory.

EXAMPLE 252

5-[4-(3,4-Dichloro-phenylsulfinyl)-butoxy]-4,4-dimethyl-4H-3,1-benzoxazin-2-one

Prepared analogously to Example 4 from 5-hydroxy-4,4-dimethyl-4H-3,1-benzoxazin-2-one and 4-(3,4-dichloro-phenylsulfinyl)-butylbromide.
M.p.: 89°–90° C.,
Yield: 73.2% of theory.

EXAMPLE 253

5-[4-(3,4-Dichloro-phenylsulfoximino)-butoxy]-4,4-dimethyl-4H-3,1-benzoxazin-2-one Prepared analogously to Example 6 from 5-[4-(3,4-dichloro-phenylsulfinyl)-butoxy]-4,4-dimethyl-4H-3,1-benzoxazin-2-one and ethyl O-mesitylenesulfonyl-acethydroxamate.
M.p.: 127°–128° C.,
Yield: 50% of theory.

EXAMPLE 254

7-[4-(3,4-Dichloro-phenylsulfoximino)-butoxy]-4,4-dimethyl-4H-3,1-benzoxazin-2-one Prepared analogously to Example 6 from 7-[4-(3,4-dichloro-phenylsulfinyl)-butoxy]-4,4-dimethyl-4H-3,1-benzoxazin-2-one and ethyl O-mesitylenesulfonyl-acethydroxamate. Resin, RF value: 0.4 [silica gel plate; ethylene chloride/ethanol (9:1)],
Yield: 39.2% of theory.
$C_{20}H_{22}Cl_2N_2O_4S$: (457.39) Calc.: C: 52.52, H: 4.85, Cl: 15.50, N: 6.12, S: 7.01. Found: C: 52.34, H: 4.80, Cl: 15.50, N: 6.16, S: 7.01

EXAMPLE 255

7-[4-(3,4-Dimethyl-phenylsulfoximino)-butoxy]-4,4-dimethyl-4H-3,1-benzoxazin-2-one Prepared analogously to Example 6 from 7-[4-(3,4-dimethyl-phenylsulfinyl)-butoxy]-4,4-dimethyl-4H-3,1-benzoxazin-2-one and ethyl O-mesitylenesulfonyl-acethydroxamate.
M.p.: 161°–163° C.,
Yield: 77.2% of theory.

EXAMPLE 256

7-[4-(4-Acetamido-phenylsulfoximino)-butoxy]-4,4-dimethyl-4H-3,1-benzoxazin-2-one Prepared analogously to Example 6 from 7-[4-(4-acetamido-phenylsulfinyl)-butoxy]-4,4-dimethyl-4H-3,1-benzoxazin-2-one and ethyl O-mesitylenesulfonyl-acethydroxamate.
M.p.: 197°–198° C.,
Yield: 29.2% of theory.

EXAMPLE 257

7-[4-(4-Methyl-phenylsulfoximino)-butoxy]-4,4-dimethyl-4H-3,1-benzoxazin-2-one

Prepared analogously to Example 6 from 7-[4-(4-methyl-phenylsulfinyl)-butoxy]-4,4-dimethyl-4H-3,1-benzoxazin-2-one and ethyl O-mesitylenesulfonyl-acethydroxamate.
M.p.: 122°–124° C.,
Yield: 54.6% of theory.

EXAMPLE 258

7-[4-(4-Chloro-phenylsulfoximino)-butoxy]-4,4-dimethyl-4H-3,1-benzoxazin-2-one

Prepared analogously to Example 6 from 7-[4-(4-chloro-phenylsulfinyl)-butoxy]-4,4-dimethyl-4H-3,1-benzoxazin-2-one and ethyl O-mesitylenesulfonyl-acethydroxamate.
M.p.: 103°–105° C.,
Yield: 53.8% of theory.

EXAMPLE 259

7-(4-Phenylsulfoximino-butoxy)-4,4-dimethyl-4H-3,1-benzoxazin-2-one

Prepared analogously to Example 6 from 7-(4-phenylsulfinyl-butoxy)-4,4-dimethyl-4H-3,1-benzoxazin-2-one and ethyl O-mesitylenesulfonyl-acethydroxamate.
M.p.: 130°–132° C.,
Yield: 75.1% of theory.

EXAMPLE 260

7-[4-(3,4-Dimethoxy-phenylsulfoximino)-butoxy]-4,4-dimethyl-4H,3,1-benzoxazin-2-one Prepared analogously to Example 6 from 7-[4-(3,4-dimethoxy-phenylsulfinyl)-butoxy]-4,4-dimethyl-4H-3,1-benzoxazin-2-one and ethyl O-mesitylenesulfonyl-acethydroxamate.
M.p.: 110°–112° C.,

EXAMPLE 261

8-[4-(4-Cyclohexyl-phenylsulfoximino)-butoxy]-4,4-dimethyl-4H-3,1-benzoxazin-2-one Prepared analogously to Example 6 from 8-[4-(4-cyclohexyl-phenylsulfinyl)-butoxy]-4,4-dimethyl-4H-3,1-benzoxazin-2-one and ethyl O-mesitylenesulfonyl-acethydroxamate.
M.p.: 115°–116° C.,
Yield: 47.9% of theory.

EXAMPLE 262

8-[4-(3,4-Dimethyl-phenylsulfoximino)-butoxy]-4,4-dimethyl-4H-3,1-benzoxazin-2-one Prepared analogously to Example 6 from 8-[4-(3,4-dimethyl-phenylsulfinyl)-butoxy]-4,4-dimethyl-4H-3,1-benzoxazin-2-one and ethyl O-mesitylenesulfonyl-acethydroxamate.
M.p.: 130°–131° C.,
Yield: 89.6% of theory.

EXAMPLE 263

8-[4-(3,4-Dichloro-phenylsulfoximino)-butoxy]-4,4-dimethyl-4H-3,1-benzoxazin-2-one Prepared analogously to Example 6 from 8-[4-(3,4-dichloro-phenylsulfinyl)-butoxy]-4,4-dimethyl-4H-3,1-benzoxazin-2-one and ethyl O-mesitylenesulfonyl-acethydroxamate.
M.p.: 144°–145° C.,
Yield: 59.6% of theory.

EXAMPLE 264

8-(4-Phenylsulfoximino-butoxy)-4,4-dimethyl-4H-3,1-benzoxazin-2-one

Prepared analogously to Example 6 from 8-(4-phenylsulfinyl-butoxy)-4,4-dimethyl-4H-3,1-benzoxazin-2-one and ethyl O-mesitylenesulfonyl-acethydroxamate.
M.p.: 103°–104° C.,
Yield: 60% of theory.

EXAMPLE 265

8-[4-(3,4-Dimethoxy-phenylsulfoximino)-butoxy]-4,4-dimethyl-4H-3,1-benzoxazin-2-one Prepared analogously to Example 6 from 8-[4-(3,4-dimethoxy-phenylsulfinyl)-butoxy]-4,4-dimethyl-4H-3,1-benzoxazin-2-one and ethyl O-mesitylenesulfonyl-acethydroxamate.
M.p.: 120°–121° C.,
Yield: 74.3% of theory.

EXAMPLE 266

8-[4-(4-Acetamido-phenylsulfoximino)-butoxy]-4,4-dimethyl-4H-3,1-benzoxazin-2-one Prepared analogously to Example 6 from 8-[4-(4-acetamido-phenylsulfinyl)-butoxy]-4,4-dimethyl-4H-3,1-benzoxazin-2-one and ethyl O-mesitylenesulfonyl-acethydroxamate.
M.p.: 166°–167° C.,
Yield: 56.6% of theory.

EXAMPLE 267

6-[4-(3,4-Dimethyl-phenylsulfoximino)-butoxy]-4,4-diethyl-4H-3,1-benzoxazin-2-one Prepared analogously to Example 6 from 6-[4-(3,4-dimethyl-phenylsulfinyl)-butoxy]-4,4-diethyl-4H-3,1-benzoxazin-2-one and ethyl O-mesitylenesulfonyl-acethydroxamate.
M.p.: 104°–105° C.,
Yield: 52.7% of theory.

EXAMPLE 268

6-[4-(3,4-Dimethoxy-phenylsulfoximino)-butoxy]-4,4-diethyl-4H-3,1-benzoxazin-2-one Prepared analogously to Example 6 from 6-[4-(3,4-dimethoxy-phenylsulfinyl)-butoxy]-4,4-diethyl-4H-3,1-benzoxazin-2-one and ethyl O-mesitylenesulfonyl-acethydroxamate.
M.p.: 93°–95° C.,
Yield: 36.9% of theory.

EXAMPLE 269

6-[4-(4-Cyclohexyl-phenylsulfoximino)-butoxy]-4,4-diethyl-4H-3,1-benzoxazin-2-one Prepared analogously to Example 6 from 6-[4-(4-cyclohexyl-phenylsulfinyl)-butoxy]-4,4-diethyl-4H-3,1-benzoxazin-2-one and ethyl O-mesitylenesulfonyl-acethydroxamate.
M.p.: 158°–160° C.,
Yield: 36.6% of theory.

EXAMPLE 270

6-[4-(4-Acetamido-phenylsulfoximino)-butoxy]-4,4-diethyl-4H-3,1-benzoxazin-2-one Prepared analogously to Example 6 from 6-[4-(4-acetamido-phenylsulfinyl)-butoxy]-4,4-diethyl-4H-3,1-benzoxazin-2-one and ethyl O-mesitylenesulfonyl-acethydroxamate.
M.p.: 144°–146° C.,
Yield: 64.0% of theory.

EXAMPLE 271

6-[4-(3,4-Dichloro-phenylsulfoximino)-butoxy]-4,4-diethyl-4H-3,1-benzoxazin-2-one Prepared analogously to Example 6 from 6-[4-(3,4-dichloro-phenylsulfinyl)-butoxy]-4,4-diethyl-4H-3,1-benzoxazin-2-one and ethyl O-mesitylenesulfonyl-acethydroxamate.
M.p.: 136°–138° C.,
Yield: 68.7% of theory.

EXAMPLE 272

6-(4-Phenylsulfoximino-butoxy)-4,4-diethyl-4H-3,1-benzoxazin-2-one

Prepared analogously to Example 6 from 6-(4-phenylsulfinyl-butoxy)-4,4-diethyl-4H-3,1-benzoxazin-2-one and ethyl O-mesitylenesulfonyl-acethydroxamate.
M.p.: 134°–135° C.,
Yield: 69.6% of theory.

EXAMPLE 273

6-[4-(3,4-Dichloro-phenylsulfoximino)-butoxy]-4-methyl-4H-3,1-benzoxazin-2-one

Prepared analogously to Example 6 from 6-[4-(3,4-dichloro-phenylsulfinyl)-butoxy]-4-methyl-4H-3,1-benzoxazin-2-one and ethyl O-mesitylenesulfonyl-acethydroxamate.
M.p.: 179°–180° C.,
Yield: 67.6% of theory.

EXAMPLE 274

6-[4-(4-Methyl-phenylsulfoximino)-butoxy]-4-methyl-4H-3,1-benzoxazin-2-one

Prepared analogously to Example 6 from 6-[4-(4-methyl-phenylsulfinyl)-butoxy]-4-methyl-4H-3,1-benzoxazin-2-one and ethyl O-mesitylenesulfonyl-acethydroxamate.
M.p.: 121°–123° C.,
Yield: 45.5% of theory.

EXAMPLE 275

6-[4-(4-Acetamido-phenylsulfoximino)-butoxy]-4-methyl-4H-3,1-benzoxazin-2-one

Prepared analogously to Example 6 from 6-[4-(4-acetamido-phenylsulfinyl)-butoxy]-4-methyl-4H-3,1-benzoxazin-2-one and ethyl O-mesitylenesulfonyl-acethydroxamate.
M.p.: 123°–125° C.,
Yield: 45.2% of theory.

EXAMPLE 276

7-[4-(3,4-Dimethyl-N-acetyl-phenylsulfoximino)-butoxy]-4,4-dimethyl-4H-3,1-benzoxazin-2-one Prepared analogously to Example 143 from 7-[4-(3,4-dimethyl-phenylsulfoximino)-butoxy]-4,4-dimethyl-4H-3,1benzoxazin-2-one and acetic anhydride.
M.p.: 151°–153° C.,
Yield: 70.0% of theory.

EXAMPLE 277

7-[4-(4-Acetamido-N-acetyl-phenylsulfoximino)-butoxy]-4,4-dimethyl-4H-3,1-benzoxazin-2-one Prepared analogously to Example 143 from 7-[4-(4-acetamido-phenylsulfoximino)-butoxy]-4,4-dimethyl-4H-3,1-benzoxazin-2-one and acetic anhydride.
M.p.: 136°–138° C.,
Yield: 38.8% of theory.

EXAMPLE 278

7-[4-(4-Methyl-N-acetyl-phenylsulfoximino)-butoxy]-4,4-dimethyl-4H-3,1-benzoxazin-2-one Prepared analogously to Example 143 from 7-[4-(4-methylphenylsulfoximino)-butoxy]-4,4-dimethyl-4H-3,1-benzoxazin-2-one and acetic anhydride.
M.p.: 142°–144° C.,
Yield: 50.7% of theory.

EXAMPLE 279

7-[4-(4-Chloro-N-acetyl-phenylsulfoximino)-butoxy]-4,4-dimethyl-4H-3,1-benzoxazin-2-one Prepared analogously to Example 143 from 7-[4-(4-chlorophenylsulfoximino)-butoxy]-4,4-dimethyl-4H-3,1-benzoxazin-2-one and acetic anhydride.
M.p.: 127°–129° C.,
Yield: 85.0% of theory.

EXAMPLE 280

7-[4-(3,4-Dichloro-N-acetyl-phenylsulfoximino)-butoxy]-4,4-dimethyl-4H-3,1-benzoxazin-2-one Prepared analogously to Example 143 from 7-[4-(3,4-dichloro-phenylsulfoximino)-butoxy]-4,4-dimethyl-4H-3,1-benzoxazin-2-one and acetic anhydride.
M.p.: 130°–132° C.,
Yield: 95.6% of theory.

EXAMPLE 281

7-[4-(N-acetyl-phenylsulfoximino)-butoxy]-4,4-dimethyl-4H-3,1-benzoxazin-2-one

Prepared analogously to Example 143 from 7-(4-phenylsulfoximino-butoxy)-4,4-dimethyl-4H-3,1-benzoxazin-2-one and acetic anhydride.
M.p.: 123°–125° C.,
Yield: 84.3% of theory.

EXAMPLE 282

7-[4-(3,4-Dimethoxy-N-acetyl-phenylsulfoximino)-butoxy]-4,4-dimethyl-4H-3,1-benzoxazin-2-one Prepared analogously to Example 143 from 7-[4-(3,4-dimethoxy-phenylsulfoximino)-butoxy]-4,4-dimethyl-4H-3,1-benzoxazin-2-one and acetic anhydride.
M.p.: 202°–204° C.,
Yield: 82.5% of theory.

EXAMPLE 283

8-[4-(4-Cyclohexyl-N-acetyl-phenylsulfoximino)-butoxy]-4,4-dimethyl-4H-3,1-benzoxazin-2-one Prepared analogously to Example 143 from 8-[4-(4-cyclohexyl-phenylsulfoximino)-butoxy]-4,4-dimethyl-4H-3,1-benzoxazin-2-one and acetic anhydride.
M.p.: 167°–168° C.,
Yield: 92.9% of theory.

EXAMPLE 284

8-[4-(3,4-Dichloro-N-acetyl-phenylsulfoximino)-butoxy]-4,4-dimethyl-4H-3,1-benzoxazin-2-one Prepared analogously to Example 143 from 8-[4-(3,4-dichloro-phenylsulfoximino)-butoxy]-4,4-dimethyl-4H-3,1-benzoxazin-2-one and acetic anhydride.
M.p.: 170°–171° C.,
Yield: 100% of theory.

EXAMPLE 285

8-[4-(3,4-Dimethyl-N-acetyl-phenylsulfoximino)-butoxy]-4,4-dimethyl-4H-3,1-benzoxazin-2-one Prepared analogously to Example 143 from 8-[4-(3,4-dimethyl-phenylsulfoximino)-butoxy]-4,4-dimethyl-4H-3,1-benzoxazin-2-one and acetic anhydride.
M.p.: 145°–146° C.,
Yield: 93.9% of theory.

EXAMPLE 286

8-[4-(N-acetyl-phenylsulfoximino)-butoxy]-4,4-dimethyl-4H-3,1-benzoxazin-2-one

Prepared analogously to Example 143 from 8-(4-phenylsulfoximino-butoxy)-4,4-dimethyl-4H-3,1-benzoxazin-2-one and acetic anhydride.
M.p.: 113°–114° C.,
Yield: 75.6% of theory.

EXAMPLE 287

8-[4-(3,4-Dimethoxy-N-acetyl-phenylsulfoximino)-butoxy]-4,4-dimethyl-4H-3,1-benzoxazin-2-one Prepared analogously to Example 143 from 8-[4-(3,4-dimethoxy-phenylsulfoximino)-butoxy]-4,4-dimethyl-4H-3,1-benzoxazin-2-one and acetic anhydride.
M.p.: 137°–138° C.,
Yield: 90.2% of theory.

EXAMPLE 288

8-[4-(4-Acetamido-N-acetyl-phenylsulfoximino)-butoxy]-4,4-dimethyl-4H-3,1-benzoxazin-2-one Prepared analogously to Example 143 from 8-[4-(4-acetamido-phenylsulfoximino)-butoxy]-4,4-dimethyl-4H-3,1-benzoxazin-2-one and acetic anhydride.
M.p.: 183°–184° C.,
Yield: 88.6% of theory.

EXAMPLE 289

6-[4-(4-Cyclohexyl-N-acetyl-phenylsulfoximino)-butoxy]-4,4-diethyl-4H-3,1-benzoxazin-2-one Prepared analogously to Example 143 from 6-[4-(4-cyclohexyl-phenylsulfoximino)-butoxy]-4,4-diethyl-4H-3,1-benzoxazin-2-one and acetic anhydride.
M.p.: 176°–178° C.,
Yield: 87.3% of theory.

EXAMPLE 290

6-[4-(3,4-Dimethyl-N-acetyl-phenylsulfoximino)-butoxy]-4,4-diethyl-4H-3,1-benzoxazin-2-one Prepared analogously to Example 143 from 6-[4-(3,4-dimethyl-phenylsulfoximino)-butoxy]-4,4-diethyl-4H-3,1-benzoxazin-2-one and acetic anhydride.
Resin, RF value: 0.52 [silica gel plate; chloroform/ethanol (9:1)],
Yield: 87.7% of theory.
$C_{26}H_{34}N_2O_5S$: (486.64) Calc.: C: 64.17, H: 7.04, N: 5.76, S: 6.59. Found: C: 63.90, H: 6.90, N: 5.51, S: 6.94.

EXAMPLE 291

6-[4-(4-Acetamido-N-acetyl-phenylsulfoximino)-butoxy]-4,4-diethyl-4H-3,1-benzoxazin-2-one Prepared analogously to Example 143 from 6-[4-(4-acetamidophenylsulfoximino)-butoxy]-4,4-diethyl-4H-3,1-benzoxazin-2-one and acetic anhydride.
M.p.: 146°–149° C.,
Yield: 88.6% of theory.

EXAMPLE 292

6-[4-(3,4-Dimethoxy-N-acetyl-phenylsulfoximino)-butoxy]-4,4-diethyl-4H-3,1-benzoxazin-2-one Prepared analogously to Example 143 from 6-[4-(3,4-dimethoxy-phenylsulfoximino)-butoxy]-4,4-diethyl-4H-3,1-benzoxazin-2-one and acetic anhydride.
Resin, RF value: 0.5 [silica gel plate; chloroform/ethanol (9:1)],
Yield: 87.2% of theory.
$C_{26}H_{34}N_2O_7S$: (518.64) Calc.: C: 60.21, H: 6.61, N: 5.40, S: 6.18. Found: C: 59.95, H: 6.58, N: 5.19, S: 6.31.

EXAMPLE 293

6-[4-(3,4-Dichloro-N-acetyl-phenylsulfoximino)-butoxy]-4,4-diethyl-4H-3,1-benzoxazin-2-one Prepared analogously to Example 143 from 6-[4-(3,4-dichloro-phenylsulfoximino)-butoxy]-4,4-diethyl-4H-3,1-benzoxazin-2-one and acetic anhydride.
M.p.: 164°–166° C.,
Yield: 86.6% of theory.

EXAMPLE 294

6-[4-(N-Acetyl-phenylsulfoximino)-butoxy]-4,4-diethyl-4H-3,1-benzoxazin-2-one

Prepared analogously to Example 143 from 6-(4-phenylsulfoximino-butoxy)-4,4-diethyl-4H-3,1-benzoxazin-2-one and acetic anhydride.
M.p.: 120°–122° C.,
Yield: 89.4% of theory.

EXAMPLE 295

6-[4-(3,4-Dichloro-phenylsulfoximino)-butoxy]-4,4-dimethyl-4H-3,1-benzoxazin-2-one Prepared analogously to Example 4 from 6-hydroxy-4,4-dimethyl-4H-3,1-benzoxazin-2-one and 4-(3,4-dichloro-phenylsulfoximino)-butylbromide-mesitylenesulfonate (m.p.: 170°–173° C.).
M.p.: 164°–166° C.,
Yield: 35.4% of theory.

EXAMPLE 296

6-[4-(3,4-Dichloro-N-acetyl-phenylsulfoximino)-butoxy]-4,4-dimethyl-4H-3,1-benzoxazin-2-one Prepared analogously to Example 4 from 6-hydroxy-4,4-dimethyl-4H-3,1-benzoxazin-2-one and 4-(3,4-dichloro-N-acetyl-phenylsulfoximino)-butylbromide (m.p.: 78°–79° C.).
M.p.: 156°–158° C.,
Yield: 66.5% of theory.

EXAMPLE 297

6-(4-Phenylsulfinyl-butoxy)-4H-3,1-benzoxazin-2-one

An amount of 4.2 gm (0.0133 mol) of 2-amino-5-(4-phenylsulfinylbutoxy)-benzyl alcohol [prepared from 2-nitro-5-(4-phenylsulfinyl-butoxy)-benzyl alcohol by catalytic hydrogenation] is dissolved in 150 ml of chloroform and mixed with 6.9 gm (0.05 mol) of potassium carbonate. Ten milliliters of a 20% solution of phosgene in toluene is slowly added dropwise to this mixture under stirring. After further stirring for two hours, the solution is washed with water and dried with sodium sulfate, and the solvents are distilled off in vacuo. The residue is recrystallized from ethyl acetate/cyclohexane.
M.p.: 115°–116° C.,
Yield: 2.1 gm (45.8% of theory).

EXAMPLE 298

7-(4-Phenylsulfoximino-butoxy)-4,4-dimethyl-4H-3,1-benzoxazin-2-one

A quantity of 1.56 gm (2.78 mmol) of potassium hydroxide is dissolved in 10 ml of methanol and mixed with 0.8 gm (1.86 mmol) of 7-[4-(N-acetyl-phenylsulfoximino)-butoxy]-4,4-dimethyl-4H-3,1-benzoxazin-2-one, under stirring, at ambient temperature. The clear solution obtained is left to stand overnight. Then, water is added, and the precipitate is subjected to suction filtration, washed with water and diisopropylether, and dried at 60° C.
M.p.: 130°–132° C.,
Yield: 0.65 gm (90% of theory).

EXAMPLE 299

7,8-Dibromo-6-[4-(4-methyl-phenylmercapto)-butoxy]-4,4-dimethyl-4H-3,1-benzoxazin-2-one Prepared analogously to Example 4 from 7,8-dibromo-6-hydroxy-4,4-dimethyl-4H-3,1-benzoxazin-2-one and 4-(4-methylphenylmercapto)-butylchloride.
M.p.: 114°–115° C.,
Yield: 45.4% of theory.

EXAMPLE 300

6-(4-Phenylsulfinyl-butoxy)-4,4,7-trimethyl-4H-3,1-benzoxazin-2-one

Prepared analogously to Example 4 from 6-hydroxy-4,4,7-trimethyl-4H-3,1-benzoxazin-2-one and 4-phenylsulfinylbutylbromide.
M.p.: 124°–125° C.,
Yield: 51.6% of theory.

EXAMPLE 301

6-[4-(3,4-Dichloro-phenylsulfinyl)-butoxy]-4,4,7-trimethyl-4H-3,1-benzoxazin-2-one Prepared analogously to Example 4 from 6-hydroxy-4,4,7-trimethyl-4H-3,1-benzoxazin-2-one and 4-(3,4-dichlorophenylsulfinyl)-butylbromide.
M.p.: 151°–152° C.,
Yield: 42.3% of theory.

EXAMPLE 302

6-[4-(4-Methyl-phenylmercapto)-butoxy]-4,4,8-trimethyl-4H-3,1-benzoxazin-2-one

Prepared analogously to Example 1 from 6-(4-chlorobutoxy-4,4,8-trimethyl-4H-3,1-benzoxazin-2-one and 4-methyl-thiophenol.
M.p.: 125°–126° C.,
Yield: 78.4% of theory.

EXAMPLE 303

6-[4-(3,4-Dichloro-phenylmercapto)-butoxy]-4,4,8-trimethyl-4H-3,1-benzoxazin-2-one Prepared analogously to Example 1 from 6-(4-chlorobutoxy)-4,4,8-trimethyl-4H-3,1-benzoxazin-2-one and 3,4-dichlorothiophenol.
M.p.: 136°–137° C.,
Yield: 68.8% of theory.

EXAMPLE 304

6-[4-(4-Acetamido-phenylmercapto)-butoxy]-4,4,8-trimethyl-4H-3,1-benzoxazin-2-one Prepared analogously to Example 1 from 6-(4-chlorobutoxy)-4,4,8-trimethyl-4H-3,1-benzoxazin-2-one and 4-acetamido-thiophenol.
M.p.: 167°–168° C.,
Yield: 64.2% of theory.

EXAMPLE 305

6-[4-(2-Pyridylmercapto)-butoxy]-4,4,8-trimethyl-4H-3,1-benzoxazin-2-one

Prepared analogously to Example 1 from 6-(4-chlorobutoxy)-4,4,8-trimethyl-4H-3,1-benzoxazin-2-one and 2-mercaptopyridine.
M.p.: 144°–145° C.,
Yield: 64.0% of theory.

EXAMPLE 306

6-[4-(4-Chloro-phenylmercapto)-butoxy]-4,4,8-trimethyl-4H-3,1-benzoxazin-2-one

Prepared analogously to Example 1 from 6-(4-chlorobutoxy)-4,4,8-trimethyl-4H-3,1-benzoxazin-2-one and 4-chloro-thiophenol.
M.p.: 141°–142° C.,
Yield: 63.5% of theory.

EXAMPLE 307

6-(4-Phenylmercapto-butoxy)-4,4,8-trimethyl-4H-3,1-benzoxazin-2-one

Prepared analogously to Example 1 from 6-(4-chlorobutoxy)-4,4,8-trimethyl-4H-3,1-benzoxazin-2-one and thiophenol.
M.p.: 125°–126° C.,
Yield: 83.1% of theory.

EXAMPLE 308

6-[4-(3,4-Dimethyl-phenylmercapto)-butoxy]-4,4,8-trimethyl-4H-3,1-benzoxazin-2-one Prepared analogously to Example 1 from 6-(4-chlorobutoxy)-4,4,8-trimethyl-4H-3,1-benzoxazin-2-one and 3,4-dimethyl-thiophenol.
M.p.: 146°–147° C.,
Yield: 78.1% of theory.

EXAMPLE 309

6-[4-(3,4-Dimethyl-phenylmercapto)-butoxy]-4,4,8-trimethyl-4H-3,1-benzoxazin-2-one Prepared analogously to Example 1 from 6-(4-chlorobutoxy)-4,4,8-trimethyl-4H-3,1-benzoxazin-2-one and 3,4-dimethoxy-thiophenol.
M.p.: 130°–131° C.,
Yield: 73.3% of theory.

EXAMPLE 310

6-[4-(4-Acetamido-phenylsulfinyl)-butoxy]-7-nitro-4,4-dimethyl-4H-3,1-benzoxazin-2-one Prepared analogously to Example 2 from 6-[4-(4-acetamido-phenylmercapto)-butoxy]-7-nitro-4,4-dimethyl-4H-3,1-benzoxazin-2-one and hydrogen peroxide.
M.p.: 240°–241° C.,
Yield: 72.6% of theory.

EXAMPLE 311

6-[4-(4-Chloro-phenylsulfinyl)-butoxy]-7-nitro-4,4-dimethyl-4H-3,1-benzoxazin-2-one Prepared analogously to Example 2 from 6-[4-(4-chlorophenylmercapto)-butoxy]-7-nitro-4,4-dimethyl-4H-3,1-benzoxazin-2-one and hydrogen peroxide.
M.p.: 159°–160° C.,
Yield: 83.4% of theory.

EXAMPLE 312

6-[4-(2-Pyridylsulfinyl)-butoxy]-7-nitro-4,4-dimethyl-4H-3,1-benzoxazin-2-one

Prepared analogously to Example 2 from 6-[4-(2-pyridylmercapto)-butoxy]-7-nitro-4,4-dimethyl-4H-3,1-benzoxazin-2-one and hydrogen peroxide.
M.p.: 156°–157° C.,
Yield: 69.1% of theory.

EXAMPLE 313

6-[4-(4-Methyl-phenylsulfinyl)-butoxy]-7-nitro-4,4-dimethyl-4H-3,1-benzoxazin-2-one Prepared analogously to Example 2 from 6-[4-(4-methylphenylmercapto)-butoxy]-7-nitro-4,4-dimethyl-4H-3,1-benzoxazin-2-one and hydrogen peroxide.
M.p.: 176°–177° C.,
Yield: 76.1% of theory.

EXAMPLE 314

6-[4-(3,4-Dimethoxy-phenylsulfinyl)-butoxy]-7-nitro-4,4-dimethyl-4H-3,1-benzoxazin-2-one Prepared analogously to Example 2 from 6-[4-(3,4-dimethoxy-phenylmercapto)-butoxy]-7-nitro-4,4-dimethyl-4H-3,1-benzoxazin-2-one and hydrogen peroxide.
M.p.: 190°–192° C.,
Yield: 84.3% of theory.

EXAMPLE 315

6-[4-(3,4-Dimethyl-phenylsulfinyl)-butoxy]-7-nitro-4,4-dimethyl-4H-3,1-benzoxazin-2-one Prepared analogously to Example 2 from 6-[4-(3,4-dimethyl-phenylmercapto)-butoxy]-7-nitro-4,4-dimethyl-4H-3,1-benzoxazin-2-one and hydrogen peroxide.
M.p.: 146°–147° C.,
Yield: 68.2% of theory.

EXAMPLE 316

8-Chloro-6-[4-(4-methyl-phenylsulfinyl)-butoxy]-4,4-dimethyl-4H-3,1-benzoxazin-2-one Prepared analogously to Example 2 from 8-chloro-6-[4-(4-methyl-phenylmercapto)-butoxy]-4,4-dimethyl-4H-3,1-benzoxazin-2-one and hydrogen peroxide.
M.p.: 113°–114° C.,
Yield: 90.3% of theory.

EXAMPLE 317

7-Chloro-6-[4-(4-methyl-phenylsulfinyl)-butoxy]-4,4-dimethyl-4H-3,1-benzoxazin-2-one Prepared analogously to Example 2 from 7-chloro-6-[4-(4-methyl-phenylmercapto)-butoxy]-4,4-dimethyl-4H-3,1-benzoxazin-2-one and hydrogen peroxide.
M.p.: 143°–144° C.,
Yield: 85.3% of theory.

EXAMPLE 318

6-[4-(4-Chloro-phenylsulfinyl)-butoxy]-8-chloro-4,4-dimethyl-4H-3,1-benzoxazin-2-one Prepared analogously to Example 2 from 8-chloro-6-[4-(4-chloro-phenylmercapto)-butoxy]-4,4-dimethyl-4H-3,1-benzoxazin-2-one and hydrogen peroxide.
M.p.: 83°–85° C.,
Yield: 78.1% of theory.

EXAMPLE 319

6-[4-(4-Chloro-phenylsulfinyl)-butoxy]-7-chloro-4,4-dimethyl-4H-3,1-benzoxazin-2-one Prepared analogously to Example 2 from 7-chloro-6-[4-(4-chloro-phenylmercapto)-butoxy]-4,4-dimethyl-4H-3,1-benzoxazin-2-one and hydrogen peroxide.
M.p.: 162°–163° C.,
Yield: 86% of theory.

EXAMPLE 320

7-Bromo-6-[4-(4-methyl-phenylsulfinyl)-butoxy]-4,4-dimethyl-4H-3,1-benzoxazin-2-one Prepared analogously to Example 2 from 7-bromo-6-[4-(4-methyl-phenylmercapto)-butoxy]-4,4-dimethyl-4H-3,1-benzoxazin-2-one and hydrogen peroxide.
M.p.: 143°–145° C.,
Yield: 78.5% of theory.

EXAMPLE 321

8-Bromo-6-[4-methyl-phenylsulfinyl)-butoxy]-4,4-dimethyl-4H-3,1-benzoxazin-2-one Prepared analogously to Example 2 from 8 bromo-6-[4-(4-methyl-phenylmercapto)-butoxy]-4,4-dimethyl-4H-3,1-benzoxazin-2-one and hydrogen peroxide.
M.p.: 123°–124° C.,
Yield: 86.4% of theory.

EXAMPLE 322

6-[4-(4-Methyl-phenylsulfinyl)-butoxy]-4,4,7-trimethyl-4H-3,1-benzoxazin-2-one

Prepared analogously to Example 2 from 6-[4-(4-methyl-phenylmercapto)-butoxy]-4,4,7-trimethyl-4H-3,1-benzoxazin-2-one and hydrogen peroxide.
M.p.: 152°–153° C.,
Yield: 87.2% of theory.

EXAMPLE 323

7,8-Dibromo-6-[4-(4-methyl-phenylsulfinyl)-butoxy]-4,4-dimethyl-4H-3,1-benzoxazin-2-one Prepared analogously to Example 2 from 7,8-dibromo-6-[4-(4-methyl-phenylmercapto)-butoxy]-4,4-dimethyl-4H-3,1-benzoxazin-2-one and hydrogen peroxide.
M.p.: 138°–139° C.,
Yield: 70.0% of theory.

EXAMPLE 324

6-[4-(3,4-Dichloro-phenylsulfinyl)-butoxy]-4,4,8-trimethyl-4H-3,1-benzoxazin-2-one Prepared analogously to Example 2 from 6-[4-(3,4-dichloro-phenylmercapto)-butoxy]-4,4,8-trimethyl-4H-3,1-benzoxazin-2-one and hydrogen peroxide.
M.p.: 158° C.,
Yield: 68% of theory.

EXAMPLE 325

6-[4-(4-Methyl-phenylsulfinyl)-butoxy]-4,4,8-trimethyl-4H-3,1-benzoxazin-2-one

Prepared analogously to Example 2 from 6-[4-(4-methyl-phenylmercapto)-butoxy]-4,4,8-trimethyl-4H-3,1-benzoxazin-2-one and hydrogen peroxide.
M.p.: 137°–138° C.,
Yield: 40% of theory.

EXAMPLE 326

6-[4-(4-Chloro-phenylsulfinyl)-butoxy]-4,4,8-trimethyl-4H-3,1-benzoxazin-2-one

Prepared analogously to Example 2 from 6-[4-(4-chloro-phenylmercapto)-butoxy]-4,4,8-trimethyl-4H-3,1-benzoxazin-2-one and hydrogen peroxide.
M.p.: 163°–164° C.,
Yield: 66.2% of theory.

EXAMPLE 327

6-[4-(3,4-Dimethoxy-phenylsulfinyl)-butoxy]-4,4,8-trimethyl-4H-3,1-benzoxazin-2-one Prepared analogously to Example 2 from 6-[4-(3,4-dimethoxy-phenylmercapto)-butoxy]-4,4,8-trimethyl-4H-3,1-benzoxazin-2-one and hydrogen peroxide.
M.p.: 142°–143° C.,
Yield: 70.5% of theory.

EXAMPLE 328

6-[4-(3,4-Dimethyl-phenylsulfinyl)-butoxy]-4,4,8-trimethyl-4H-3,1-benzoxazin-2-one Prepared analogously to Example 2 from 6-[4-(3,4-dimethyl-phenylmercapto)-butoxy]-4,4,8-trimethyl-4H-3,1-benzoxazin-2-one and hydrogen peroxide.
M.p.: 113°–114° C.,
Yield: 72.9% of theory.

EXAMPLE 329

6-(4-Phenylsulfinyl-butoxy)-4,4,8-trimethyl-4H-3,1-benzoxazin-2-one

Prepared analogously to Example 2 from 6-(4-phenylmercapto-butoxy)-4,4,8-trimethyl-4H-3,1-benzoxazin-2-one and hydrogen peroxide.
M.p.: 143°–144° C.,
Yield: 77.6% of theory.

EXAMPLE 330

6-[4-(4-Acetamido-phenylsulfinyl)-butoxy]-4,4,8-trimethyl-4H-3,1-benzoxazin-2-one Prepared analogously to Example 2 from 6-[4-(4-acetamido-phenylmercapto)-butoxy]-4,4,8-trimethyl-4H-3,1-benzoxazin-2-one and hydrogen peroxide.
M.p.: 212°–213° C.,
Yield: 57.9% of theory.

EXAMPLE 331

6-[4-(2-Pyridysulfinyl)-butoxy]-4,4,8-trimethyl-4H-3,1-benzoxazin-2-one

Prepared analogously to Example 2 from 6-[4-(2-pyridylmercapto)-butoxy]-4,4,8-trimethyl-4H-3,1-benzoxazin-2-one and hydrogen peroxide.
M.p.: 163°–164° C.,
Yield: 65.8% of theory.

EXAMPLE 332

6-[4-(3,4-Dimethoxy-phenylsulfoximino)-butoxy]-4,4,8-trimethyl-4H-3,1-benzoxazin-2-one Prepared analogously to Example 6 from 6-[4-(3,4-dimethoxy-phenylsulfinyl)-butoxy]-4,4,8-trimethyl-4H-3,1-benzoxazin-2-one and ethyl O-mesitylenesulfonyl-acethydroxamate.
M.p.: 175°–176° C.,
Yield: 58.7% of theory.

EXAMPLE 333

6-[4-(3,4-Dimethyl-phenylsulfoximino)-butoxy]-4,4,8-trimethyl-4H-3,1-benzoxazin-2-one Prepared analogously to Example 6 from 6-[4-(3,4-dimethyl-phenylsulfinyl)-butoxy]-4,4,8-trimethyl-4H-3,1-benzoxazin-2-one and ethyl O-mesitylenesulfonyl-acethydroxamate.
M.p.: 174°–175° C.,
Yield: 61.8% of theory.

EXAMPLE 334

6-(4-Phenylsulfoximino-butoxy)-4,4,8-trimethyl-4H-3,1-benzoxazin-2-one

Prepared analogously to Example 6 from 6-(4-phenylsulfinyl-butoxy)-4,4,8-trimethyl-4H-3,1-benzoxazin-2-one and ethyl O-mesitylenesulfonyl-acethydroxamate.
M.p.: 147°–148° C.,
Yield: 66.8% of theory.

EXAMPLE 335

6-[4-(3,4-Dichloro-phenylsulfoximino)-butoxy]-4,4,8-trimethyl-4H-3,1-benzoxazin-2-one Prepared analogously to Example 6 from 6-[4-(3,4-dichloro-phenylsulfinyl)-butoxy]-4,4,8-trimethyl-4H-3,1-benzoxazin-2-one and ethyl O-mesitylenesulfonyl-acethydroxamate.
M.p.: 116°–117° C.,
Yield: 50.0% of theory.

EXAMPLE 336

6-[4-(4-Chloro-phenylsulfoximino)-butoxy]-4,4,8-trimethyl-4H-3,1-benzoxazin-2-one Prepared analogously to Example 6 from 6-[4-(4-chloro-phenylsulfinyl)-butoxy]-4,4,8-trimethyl-4H-3,1-benzoxazin-2-one and ethyl O-mesitylenesulfonyl-acethydroxamate.
M.p.: 167°–168° C.,
Yield: 72.8% of theory.

EXAMPLE 337

6-[4-(4-Methyl-phenylsulfoximino)-butoxy]-4,4,8-trimethyl-4H-3,1-benzoxazin-2-one Prepared analogously to Example 6 from 6-[4-(4-methyl-phenysulfinyl)-butoxy]-4,4,8-trimethyl-4H-3,1-benzoxazin-2-one and ethyl O-mesitylenesulfonyl-acethydroxamate.
M.p.: 183°–184° C.,
Yield: 71.5% of theory.

EXAMPLE 338

6-[4-(4-Acetamido-phenylsulfoximino)-butoxy]-4,4,8-trimethyl-4H-3,1-benzoxazin-2-one Prepared analogously to Example 6 from 6-[4-(4-acetamido-phenylsulfinyl)-butoxy]-4,4-8-trimethyl-4H-3,1-benzoxazin-2-one and ethyl O-mesitylenesulfonyl-acethydroxamate.
M.p.: 168°–169° C.,
Yield: 66.1% of theory.

EXAMPLE 339

6-[4-(4-Acetamido-phenylsulfoximino)-butoxy]-4,4-dimethyl-7-nitro-4H-3,1-benzoxazin-2-one Prepared analogously to Example 6 from 6-[4-(4-acetamido-phenylsulfinyl)-butoxy]-4,4-dimethyl-7-nitro-4H-3,1-benzoxazin-2-one and ethyl O-mesitylenesulfonyl-acethydroxamate.
M.p.: 209°–211° C.,
Yield: 55.4% of theory.

EXAMPLE 340

6-[4-(4-Chloro-phenylsulfoximino)-butoxy]-4,4-dimethyl-7-nitro-4H-3,1-benzoxazin-2-one Prepared analogously to Example 6 from 6-[4-(4-chloro-phenylsulfinyl)-butoxy]-4,4-dimethyl-7-nitro-4H-3,1-benzoxazin-2-one and ethyl O-mesitylenesulfonyl-acethydroxamate.
M.p.: 116°–118° C.,
Yield: 88.3% of theory.

EXAMPLE 341

6-[4-(4-Methyl-phenylsulfoximino)-butoxy]-4,4-dimethyl-7-nitro-4H-3,1-benzoxazin-2-one Prepared analogously to Example 6 from 6-[4-(4-methyl-phenylsulfinyl)-butoxy]-4,4-dimethyl-7-nitro-4H-3,1-benzoxazin-2-one and ethyl O-mesitylenesulfonyl-acethydroxamate.
M.p.: 112°–114° C.,
Yield: 86.2% of theory.

EXAMPLE 342

6-[4-(3,4-Dimethoxy-phenylsulfoximino)-butoxy]-4,4-dimethyl-7-nitro-4H-3,1-benzoxazin-2-one Prepared analogously to Example 6 from 6-[4-(3,4-dimethoxy-phenylsulfinyl)-butoxy]-4,4-dimethyl-7-nitro-4H-3,1-benzoxazin-2-one and ethyl O-mesitylenesulfonyl-acethydroxamate.
M.p.: 147°–149° C.,
Yield: 41.4% of theory.

EXAMPLE 343

6-[4-(3,4-Dimethyl-phenylsulfoximino)-butoxy]-4,4-dimethyl-7-nitro-4H-3,1-benzoxazin-2-one Prepared analogously to Example 6 from 6-[4-(3,4-dimethyl-phenylsulfinyl)-butoxy]-4,4-dimethyl-7-nitro-4H-3,1-benzoxazin-2-one and ethyl O-mesitylenesulfonyl-acethydroxamate.
M.p.: 145°–146° C.,
Yield: 67% of theory.

EXAMPLE 344

8-Chloro-6-[4-(3,4-dichloro-phenylsulfoximino)-butoxy]-4,4-dimethyl-4H-3,1-benzoxazin-2-one Prepared analogously to Example 6 from 8-chloro-6-[4-(3,4-dichloro-phenylsulfinyl)-butoxy]-4,4-dimethyl-4H-3,1-benzoxazin-2-one and ethyl O-mesitylenesulfonyl-acethydroxamate.
M.p.: 135°–136° C.,
Yield: 74.3% of theory.

EXAMPLE 345

7-Chloro-6-[4-(3,4-dichloro-phenylsulfoximino)-butoxy]-4,4-dimethyl-4H-3,1-benzoxazin-2-one Prepared analogously to Example 6 from 7-chloro-6-[4-(3,4-dichloro-phenylsulfinyl)-butoxy]-4,4-dimethyl-4H-3,1-benzoxazin-2-one and ethyl O-mesitylenesulfonyl-acethydroxamate.
M.p.: 87° C.,
Yield: 58.3% of theory.

EXAMPLE 346

8-Chloro-6-[4-(4-methyl-phenylsulfoximino)-butoxy]-4,4-dimethyl-4H-3,1-benzoxazin-2-one Prepared analogously to Example 6 from 8-chloro-6-[4-(4-methyl-phenylsulfinyl)-butoxy]-4,4-dimethyl-4H-3,1-benzoxazin-2-one and ethyl O-mesitylenesulfonyl-acethydroxamate.
M.p.: 132°–133° C.,
Yield: 55.1% of theory.

EXAMPLE 347

7-Chloro-6-[4-(4-methyl-phenylsulfoximino)-butoxy]-4,4-dimethyl-4H-3,1-benzoxazin-2-one Prepared analogously to Example 6 from 7-chloro-6-[4-(4-methyl-phenylsulfinyl)-butoxy]-4,4-dimethyl-4H-3,1-benzoxazin-2-one and ethyl O-mesitylenesulfonyl-acethydroxamate.
M.p.: 115°–116° C.,
Yield: 55.1% of theory.

EXAMPLE 348

8-Chloro-6-[4-(4-chloro-phenylsulfoximino)-butoxy]-4,4-dimethyl-4H-3,1-benzoxazin-2-one Prepared analogously to Example 6 from 8-chloro-6-[4-(4-chloro-phenylsulfinyl)-butoxy]-4,4-dimethyl-4H-3,1-benzoxazin-2-one and ethyl O-mesitylenesulfonyl-acethydroxamate.
M.p.: 162°–163° C.,
Yield: 57% of theory.

EXAMPLE 349

7-Chloro-6-[4-(4-chloro-phenylsulfoximino)-butoxy]-4,4-dimethyl-4H-3,1-benzoxazin-2-one Prepared analogously to Example 6 from 7-chloro-6-[4-(4-chloro-phenylsulfinyl)-butoxy]-4,4-dimethyl-4H-3,1-benzoxazin-2-one and ethyl O-mesitylenesulfonyl-acethydroxamate.
M.p.: 132°–133° C.,
Yield: 65.8% of theory.

EXAMPLE 350

6-[4-(3,4-Dichloro-phenylsulfoximino)-butoxy]-4,4,7-trimethyl-4H-3,1-benzoxazin-2-one Prepared analogously to Example 6 from 6-[4-(3,4-dichloro-phenylsulfinyl)-butoxy]-4,4,7-trimethyl-4H-3,1-benzoxazin-2-one and ethyl O-mesitylenesulfonyl-acethydroxamate.
M.p.: 135°–137° C.,
Yield: 63.6% of theory.

EXAMPLE 351

6-(4-Phenylsulfoximino-butoxy)-4,4,7-trimethyl-4H-3,1-benzoxazin-2-one

Prepared analogously to Example 6 from 6-(4-phenylsulfinyl-butoxy)-4,4,7-trimethyl-4H-3,1-benzoxazin-2-one and ethyl O-mesitylenesulfonyl-acethydroxamate.
M.p.: 123°–124° C.,
Yield: 77% of theory.

EXAMPLE 352

6-[4-(4-Methyl-phenylsulfoximino)-butoxy]-4,4,7-trimethyl-4H-3,1-benzoxazin-2-one Prepared analogously to Example 6 from 6-[4-(4-methyl-phenylsulfinyl)-butoxy]-4,4,7-trimethyl-4H-3,1-benzoxazin-2-one and ethyl O-mesitylenesulfonyl-acethydroxamate.
M.p.: 153°–154° C.,
Yield: 57.6% of theory.

EXAMPLE 353

6-[4-(4-Acetamido-N-acetyl-phenylsulfoximino)-butoxy]-7-nitro-4,4-dimethyl-4H-3,1-benzoxazin-2-one Prepared analogously to Example 143 from 6-[4-(4-acetamido-phenylsulfoximino)-butoxy]-7-nitro-4,4-dimethyl-4H-3,1-benzoxazin-2-one and acetic anhydride.
M.p.: 250°–252° C.,
Yield: 92% of theory.

EXAMPLE 354

6-[4-(4-Chloro-N-acetyl-phenylsulfoximino)-butoxy]-7-nitro-4,4-dimethyl-4H-3,1-benzoxazin-2-one Prepared analogously to Example 143 from 6-[4-(4-chloro-phenylsulfoximino)-butoxy]-7-nitro-4,4-dimethyl-4H-3,1-benzoxazin-2-one and acetic anhydride.
M.p.: 211°–213° C.,
Yield: 82.4% of theory.

EXAMPLE 355

6-[4-(4-Methyl-N-acetyl-phenylsulfoximino)-butoxy]-7-nitro-4,4-dimethyl-4H-3,1-benzoxazin-2-one Prepared analogously to Example 143 from 6-[4-(4-methyl-phenylsulfoximino)-butoxy]-7-nitro-4,4-dimethyl-4H-3,1-benzoxazin-2-one and acetic anhydride.
M.p.: 214°–216° C.,
Yield: 85.8% of theory.

EXAMPLE 356

6-[4-(3,4-Dimethoxy-N-acetyl-phenylsulfoximino)-butoxy]-7-nitro-4,4-dimethyl-4H-3,1-benzoxazin-2-one Prepared analogously to Example 143 from 6-[4-(3,4-dimethoxy-phenylsulfoximino)-butoxy]-7-nitro-4,4-dimethyl-4H-3,1-benzoxazin-2-one and acetic anhydride.
M.p.: 120°–122° C.,
Yield: 82.2% of theory.

EXAMPLE 357

6-[4-(3,4-Dimethoxy-N-acetyl-phenylsulfoximino)-butoxy]-4,4,8-trimethyl-4H-3,1-benzoxazin-2-one Prepared analogously to Example 143 from 6-[4-(3,4-dimethoxy-phenylsulfoximino)-butoxy]-4,4,8-trimethyl-4H-3,1-benzoxazin-2-one and acetic anhydride.
M.p.: 123°–124° C.,
Yield: 76.5% of theory.

EXAMPLE 358

6-[4-(3,4-Dimethyl-N-acetyl-phenylsulfoximino)-butoxy]-4,4,8-trimethyl-4H-3,1-benzoxazin-2-one Prepared analogously to Example 143 from 6-[4-(3,4-dimethyl-phenylsulfoximino)-butoxy]-4,4,8-trimethyl-4H-3,1-benzoxazin-2-one and acetic anhydride.
M.p.: 146°–147° C.,
Yield: 83.1% of theory.

EXAMPLE 359

6-[4-(N-acetyl-phenylsulfoximino)-butoxy]-4,4,8-trimethyl-4H-3,1-benzoxazin-2-one Prepared analogously to Example 143 from 6-(4-phenylsulfoximino-butoxy)-4,4,8-trimethyl-4H-3,1-benzoxazin-2-one and acetic anhydride.
M.p.: 99°–100° C.,
Yield: 71.0% of theory.

EXAMPLE 360

6-[4-(3,4-Dichloro-N-acetyl-phenylsulfoximino)-butoxy]-4,4,8-trimethyl-4H-3,1-benzoxazin-2-one Prepared analogously to Example 143 from 6-[4-(3,4-dichloro-phenylsulfoximino)-butoxy]-4,4,8-trimethyl-4H-3,1-benzoxazin-2-one and acetic anhydride.
M.p.: 140°–141° C.,
Yield: 76.9% of theory.

EXAMPLE 361

6-[4-(4-Chloro-N-acetyl-phenylsulfoximino)-butoxy]-4,4,8-trimethyl-4H-3,1-benzoxazin-2-one Prepared analogously to Example 143 from 6-[4-(4-chlorophenylsulfoximino)-butoxy]-4,4,8-trimethyl-4H-3,1-benzoxazin-2-one and acetic anhydride.
M.p.: 178°–179° C.,
Yield: 79.9% of theory.

EXAMPLE 362

8-Chloro-6-[4-(3,4-dichloro-phenylsulfinyl)-butoxy]-4,4-dimethyl-4H-3,1-benzoxazin-2-one Prepared analogously to Example 4 from 8-chloro-6-hydroxy-4,4-dimethyl-4H-3,1-benzoxazin-2-one and 4-(3,4-dichloro-phenylsulfinyl)-butylbromide.
M.p.: 121°–122° C.,
Yield: 62.0% of theory.

EXAMPLE 363

7-Chloro-6-[4-(3,4-dichloro-phenylsulfinyl)-butoxy]-4,4-dimethyl-4H-3,1-benzoxazin-2-one Prepared analogously to Example 4 from 7-chloro-6-hydroxy-4,4-dimethyl-4H-3,1-benzoxazin-2-one and 4-(3,4-dichloro-phenylsulfinyl)-butylbromide.
M.p.: 125°–127° C.,
Yield: 41.5% of theory.

EXAMPLE 364

8-Chloro-6-[4-(4-methyl-phenylmercapto)-butoxy]-4,4-dimethyl-4H-3,1-benzoxazin-2-one Prepared analogously to Example 4 from 8-chloro-6-hydroxy-4,4-dimethyl-4H-3,1-benzoxazin-2-one and 4-(4-methylphenylmercapto)-butylchloride.
M.p.: 111°–112° C.,
Yield: 56.0% of theory.

EXAMPLE 365

8-Chloro-6-(4-phenylsulfinyl-butoxy)-4,4-dimethyl-4H-3,1-benzoxazin-2-one

Prepared analogously to Example 4 from 8-chloro-6-hydroxy-4,4-dimethyl-4H-3,1-benzoxazin-2-one and 4-phenylsulfinyl-butylbromide.
M.p.: 154°–155° C.,
Yield: 39.3% of theory.

EXAMPLE 366

7-Chloro-6-(4-phenylsulfinyl-butoxy)-4,4-dimethyl-4H-3,1-benzoxazin-2-one

Prepared analogously to Example 4 from 7-chloro-6-hydroxy-4,4-dimethyl-4H-3,1-benzoxazin-2-one and 4-phenylsulfinyl-butylbromide.
M.p.: 124°-125° C.,
Yield: 31.5% of theory.

EXAMPLE 367

7-Chloro-6-[4-(4-methyl-phenylmercapto)-butoxy]-4,4-dimethyl-4H-3,1-benzoxazin-2-one Prepared analogously to Example 4 from 7-chloro-6-hydroxy-4,4-dimethyl-4H-3,1-benzoxazin-2-one and 4-(4-methylphenylmercapto)-butylchloride.
M.p.: 118°-119° C.,
Yield: 52.6% of theory.

EXAMPLE 368

7-Bromo-6-[4-(3,4-dichloro-phenylsulfinyl)-butoxy]-4,4-dimethyl-4H-3,1-benzoxazin-2-one Prepared analogously to Example 4 from 7-bromo-6-hydroxy-4,4-dimethyl-4H-3,1-benzoxazin-2-one and 4-(3,4-dichloro-phenylsulfinyl)-butylbromide.
M.p.: 136°-138° C.,
Yield: 75.0% of theory.

EXAMPLE 369

7-Bromo-6-(4-phenylsulfinyl-butoxy)-4,4-dimethyl-4H-1,3-benzoxazin-2-one

Prepared analogously to Example 4 from 7-bromo-6-hydroxy-4,4-dimethyl-4H-3,1-benzoxazin-2-one and 4-phenylsulfinyl-butylbromide.
M.p.: 119°-120° C.,
Yield: 53.1% of theory.

EXAMPLE 370

8-Chloro-6-[4-(4-chloro-phenylmercapto)-butoxy]-4,4-dimethyl-4H-3,1-benzoxazin-2-one Prepared analogously to Example 4 from 8-chloro-6-hydroxy-4,4-dimethyl-4H-3,1-benzoxazin-2-one and 4-(4-chloro-phenylmercapto)-butylchloride.
M.p.: 138°-139° C.,
Yield: 56.7% of theory.

EXAMPLE 371

8-Bromo-6-[4-(3,4-dichloro-phenylsulfinyl)-butoxy]-4,4-dimethyl-4H-3,1-benzoxazin-2-one Prepared analogously to Example 4 from 8-bromo-6-hydroxy-4,4-dimethyl-4H-3,1-benzoxazin-2-one and 4-(3,4-dichloro-phenylsulfinyl)-butylbromide.
M.p.: 74° C.,
Yield: 82.5% of theory.

EXAMPLE 372

8-Bromo-6-(4-phenylsulfinyl-butoxy)-4,4-dimethyl-4H-3,1-benzoxazin-2-one

Prepared analogously to Example 4 from 8-bromo-6-hydroxy-4,4-dimethyl-4H-3,1-benzoxazin-2-one and 4-phenylsulfinyl-butylbromide.
M.p.: 129°-130° C.,
Yield: 44.1% of theory.

EXAMPLE 373

7-Chloro-6-[4-(4-chloro-phenylmercapto)-butoxy]-4,4-dimethyl-4H-3,1-benzoxazin-2-one Prepared analogously to Example 4 from 7-chloro-6-hydroxy-4,4-dimethyl-4H-3,1-benzoxazin-2-one and 4-(4-chloro-phenylmercapto)-butylchloride.
M.p.: 125°-126° C.
Yield: 45.2% of theory.

EXAMPLE 374

6-[4-(4-Methyl-phenylmercapto)-butoxy]-4,4,7-trimethyl-4H-3,1-benzoxazin-2-one

Prepared analogously to Example 4 from 6-hydroxy-4,4,7-trimethyl-4H-3,1-benzoxazin-2-one and 4-(4-methyl-phenylmercapto)-butylchloride.
M.p.: 114°-115° C.,
Yield: 51.9% of theory.

EXAMPLE 375

7-Bromo-6-[4-(4-methyl-phenylmercapto)-butoxy]-4,4-dimethyl-4H-3,1-benzoxazin-2-one Prepared analogously to Example 4 from 7-bromo-6-hydroxy-4,4-dimethyl-4H-3,1-benzoxazin-2-one and 4-(4-methyl-phenylmercapto)-butylchloride.
M.p.: 122°-123° C.,
Yield: 43.3% of theory.

EXAMPLE 376

8-Bromo-6-[4-(4-methyl-phenylmercapto)-butoxy]-4,4-dimethyl-4H-3,1-benzoxazin-2-one Prepared analogously to Example 4 from 8-bromo-6-hydroxy-4,4-dimethyl-4H-3,1-benzoxazin-2-one and 4-(4-methyl-phenylmercapto)-butylchloride.
M.p.: 115°-116° C.,
Yield: 43.3% of theory.

EXAMPLE 377

8-Chloro-6-[4-(4-methyl-phenylsulfinyl)-butoxy]-4H-3,1-benzoxazin-2-one

Prepared analogously to Example 2 from 8-chloro-6-[4-(4-methyl-phenylmercapto)-butoxy]-4H-3,1-benzoxazin-2-one and hydrogen peroxide.
M.p.: 114°-115° C.,
Yield: 72.7% of theory.

EXAMPLE 378

6-[4-(4-Acetamido-phenylsulfinyl)-butoxy]-4,4,7-trimethyl-4H-3,1-benzoxazin-2-one Prepared analogously to Example 2 from 6-[4-(4-acetamido-phenylmercapto)-butoxy]-4,4,7-trimethyl-4H-3,1-benzoxazin-2-one and hydrogen peroxide.
M.p.: 210°-211° C.,
Yield: 70.6% of theory.

EXAMPLE 379

6-[4-(4-Methyl-phenylsulfinyl)-butoxy]-4,4,7-trimethyl-4H-3,1-benzoxazin-2-one

Prepared analogously to Example 2 from 6-[4-(4-methylphenylmercapto)-butoxy]-4,4,7-trimethyl-4H-3,1-benzoxazin-2-one and hydrogen peroxide.
M.p.: 152°-153° C.,
Yield: 87.2% of theory.

EXAMPLE 380

8-Chloro-6-[4-(4-acetamido-phenylsulfinyl)-butoxy]-4H-3,1-benzoxazin-2-one

Prepared analogously to Example 2 from 8-chloro-6-[4-(4-acetamido-phenylmercapto)-butoxy]-4H-3,1-benzoxazin-2-one and hydrogen peroxide.
M.p.: 130°–132° C.,
Yield: 85.0% of theory.

EXAMPLE 381

5,7-Dimethyl-6-[4-(4-methyl-phenylmercapto)-butoxy]-4H-3,1-benzoxazin-2-one

Prepared analogously to Example 4 from 5,7-dimethyl-6-hydroxy-4H-3,1-benzoxazin-2-one and 4-(4-methyl-phenylmercapto)-butylchloride.
M.p.: 107°–109° C.,
Yield: 28.3% of theory.

EXAMPLE 382

6-[4-(4-Methyl-phenylsulfinyl)-butoxy]-5,7-dimethyl-4H-3,1-benzoxazin-2-one

Prepared analogously to Example 2 from 6-[4-(4-methylphenylmercapto)-butoxy]-5,7-dimethyl-4H-3,1-benzoxazin-2-one and hydrogen peroxide.
M.p.: 114°–116° C.,
Yield: 52.6% of theory.

EXAMPLE 383

6-[4-(3,4-Dichloro-phenylsulfinyl)-butoxy]-5,7-dimethyl-4H-3,1-benzoxazin-2-one

Prepared analogously to Example 2 from 6-[4-(3,4-dichloro-phenylmercapto)-butoxy]-5,7-dimethyl-4H-3,1-benzoxazin-2-one and hydrogen peroxide.
M.p.: 126°–128° C.,
Yield: 39.8% of theory.

EXAMPLE 384

7-Chloro-6-[4-(4-methyl-phenylsulfinyl)-butoxy]-4H-3,1-benzoxazin-2-one

Prepared analogously to Example 2 from 7-chloro-6-[4-(4-methyl-phenylmercapto)-butoxy]-4H-3,1-benzoxazin-2-one and hydrogen peroxide.
M.p.: 177°–178° C.,
Yield: 72.0% of theory.

EXAMPLE 385

5-Chloro-6-[4-(4-methyl-phenylsulfinyl)-butoxy]-4H-3,1-benzoxazin-2-one

Prepared analogously to Example 2 from 6-chloro-6-[4-(4-methyl-phenylmercapto)-butoxy]-4H-3,1-benzoxazin-2-one and hydrogen peroxide.
M.p.: 183°–185° C.,
Yield: 20.6% of theory.

EXAMPLE 386

5,7-Dichloro-6-[4-(4-methyl-phenylsulfinyl)-butoxy]-4,4-dimethyl-4H-3,1-benzoxazin-2-one Prepared analogously to Example 2 from 5,7-dichloro-6-[4-(4-methyl-phenylmercapto)-butoxy]-4,4-dimethyl-4H-3,1-benzoxazin-2-one and hydrogen peroxide.
M.p.: 169°–170° C.,
Yield: 75.0% of theory.

EXAMPLE 387

5,7-Dichloro-6-(4-phenylsulfinyl-butoxy)-4,4-dimethyl-4H-3,1-benzoxazin-2-one

Prepared analogously to Example 2 from 5,7-dichloro-6-(4-phenylmercapto-butoxy)-4,4-dimethyl-4H-3,1-benzoxazin-2-one and hydrogen peroxide.
M.p.: 186°–187° C.,
Yield: 74.0% of theory.

EXAMPLE 388

6-[4-(4-Acetamido-phenylmercapto)-butoxy]-4,4,7-trimethyl-4H-3,1-benzoxazin-2-one Prepared analogously to Example 4 from 6-hydroxy-4,4,7-trimethyl-4H-3,1-benzoxazin-2-one and 4-(4-acetamidophenylmercapto)-butylmesylate.
M.p.: 104°–106° C.,
Yield: 50.9% of theory.

EXAMPLE 389

7-Chloro-6-[4-(4-methyl-phenylmercapto)-butoxy]-4H-3,1-benzoxazin-2-one

Prepared analogously to Example 4 from 7-chloro-6-hydroxy-4H-3,1-benzoxazin-2-one and 4-(4-methylphenylmercapto)-butylchloride.
M.p.: 145°–147° C.,
Yield: 44% of theory.

EXAMPLE 390

7-Chloro-6-(4-phenylsulfinyl-butoxy)-4H-3,1-benzoxazin-2-one

Prepared analogously to Example 4 from 7-chloro-6-hydroxy-4H-3,1-benzoxazin-2-one and 4-phenylsulfinyl-butylchloride.
M.p.: 177°–179° C.,
Yield: 18.1% of theory.

EXAMPLE 391

5-Chloro-6-[4-(4-methyl-phenylmercapto)-butoxy]-4H-3,1-benzoxazin-2-one

Prepared analogously to Example 4 from 5-chloro-6-hydroxy-4H-3,1-benzoxazin-2-one and 4-(4-methylphenylmercapto)-butylchloride.
M.p.: 144°–145° C.,
Yield: 12.7% of theory.

EXAMPLE 392

5,7-Dichloro-6-[4-(4-methyl-phenylmercapto)-butoxy]-4,4-dimethyl-4H-3,1-benzoxazin-2-one Prepared analogously to Example 4 from 5,7-dichloro-6-hydroxy-4,4-dimethyl-4H-3,1-benzoxazin-2-one and 4-(4-methyl-phenylmercapto)-butylchloride.
M.p.: 127°–128° C.,
Yield: 50.0% of theory.

EXAMPLE 393

6-[4-(4-Acetamido-phenylsulfoximino)-butoxy]-4,4,7-trimethyl-4H-3,1-benzoxazin-2-one Prepared analogously to Example 6 from 6-[4-(4-acetamido-phenylsulfinyl)-butoxy]-4,4,7-trimethyl-4H-3,1-benzoxazin-2-one and ethyl O-mesitylenesulfonylacethydroxamate.
M.p.: 158°–161° C.,
Yield: 53.3% of theory.

The following examples illustrate a few pharmaceutical compositions comprising a compound of the present invention as an active ingredient and represent the best modes contemplated of using the invention. The compounds 6-[4-(3,4-dichloro-phenylsulfoximino)-butoxy]-4,4-dimethyl-4H-3,1-benzoxazin-2-one and 6-[4-(3,4-dimethyl-phenylsulfoximino)-butoxy]-4,4-dimethyl-4H-3,1-benzoxazin-2-one are designated Active Ingredient A and Active Ingredient B, respectively. It should be understood that one or more other compounds of Formula I can be used in place of Active Ingredient A or B.

EXAMPLE 394

Coated Tablets Containing 4 mg of Active Ingredient A

Each tablet core has the following composition:

| Component | Amount (mg) |
|---|---|
| (1) Active Substance A | 4.0 |
| (2) Lactose | 27.0 |
| (3) Corn starch | 14.5 |
| (4) Polyvinylpyrrolidone | 4.0 |
| (5) Magnesium stearate | 0.5 |
| Total: | 50.0 |

Preparation

Substances (1) to (3) are homogeneously moistened with an aqueous solution of (4), passed through a screen with a mesh size of 1 mm, dried, and again passed through a 1 mm mesh screen. After addition of (5), the mixture is compressed to form tablet cores.

Tablet cores: 5 mm $\phi$, biconvex, round.

Coating

Usual sugar coating to give a finished weight of 70 mg.

EXAMPLE 395

Tablets containing 8 mg of Active Ingredient A

Each tablet has the following composition:

| Component | Amount (mg) |
|---|---|
| Active Substance A | 8.0 |
| Lactose | 23.0 |
| Corn starch | 14.5 |
| Polyvinylpyrrolidone | 4.0 |
| Magnesium stearate | 0.5 |
| Total: | 50.0 |

Preparation

Analogously to the tablet core in Example 394.

Description of tablets

Weight: 50 mg
Diameter: 5 mm, biplanar, facetted on both sides.

EXAMPLE 396

Suppositories containing 25 mg of Active Ingredient A

Each suppository has the following composition:

| Component | Amount (mg) |
|---|---|
| Active Ingredient A | 25 |
| Suppository mass (e.g., WITEPSOL ® H19 or W45 available from Chemische Werke Witten GmbH) | 1675 |
| Total: | 1700 |

Preparation

The suppository mass is melted, and after the molten mass has been cooled to 38° C., ground Active Ingredient A is homogeneously dispersed therein. The molten mass is then cooled to 35° C. and poured into slightly chilled suppository molds.

Weight of one suppository: 1.7 gm.

EXAMPLE 397

Suspension Containing 1.6 mg/ml of Active Ingredient A

One hundred milliliters of suspension has the following composition:

| Component | Amount |
|---|---|
| Active Ingredient A | 0.16 gm |
| Carboxymethyl cellulose | 0.1 gm |
| Methyl p-hydroxybenzoate | 0.05 gm |
| Propyl p-hydroxybenzoate | 0.01 gm |
| Sucrose | 10.0 gm |
| Glycerin | 5.0 gm |
| 70% Sorbitol solution | 20.0 gm |
| Flavoring | 0.3 gm |
| Distilled water q.s. ad | 100.0 ml |

Preparation

Distilled water is heated to 70° C. The methyl and propyl p-hydroxybenzoates are dissolved therein, under stirring, together with the glycerin and carboxymethyl cellulose. The solution is cooled to ambient temperature, and the active ingredient is added and homogeneously dispersed therein with stirring. After the sugar, sorbitol, and flavoring have been added and dissolved, the suspension is evacuated, under stirring, to eliminate air.

EXAMPLE 398

Tablets Containing 100 mg of Active Ingredient B

Each tablet has the following composition:

| Component | Amount (mg) |
|---|---|
| Active Ingredient B | 100.0 |
| Lactose | 80.0 |
| Corn starch | 34.0 |
| Polyvinylpyrrolidone | 4.0 |
| Magnesium stearate | 2.0 |
| Total: | 220.0 |

Preparation

The active substance, lactose, and starch are mixed together and homogeneously moistened with an aqueous solution of the polyvinylpyrrolidone. After the moist masses have been screened (2.0 mm mesh size) and dried in a rack drier at 50° C., they are screened again (1.5 mm mesh size), and the lubricant is added. The finished mixture is made into tablets.

Weight of tablet: 220 mg

Diameter: 10 mm, biplanar, facetted on both sides and notched on one side.

EXAMPLE 399

Hard Gelatine Capsules containing 150 mg of Active Ingredient B

Each capsule contains the following:

| Component | Amount (mg) |
| --- | --- |
| Active Ingredient B | 150.0 |
| Dried corn starch | 180.0 (approx.) |
| Powdered lactose | 87.0 (approx.) |
| Magnesium stearate | 3.0 |
| Total: | 320.0 (approx.) |

Preparation

The active ingedient is mixed with the excipients, passed through a screen with a mesh size of 0.75 mm, and homogeneously mixed in a suitable apparatus. The final mixture is packed into size 1 hard gelatine capsules.
Capsule contents: about 320 mg
Capsule casing: hard gelatine capsule size 1.

EXAMPLE 400

Suppositories containing 150 mg of Active Ingredient B

Each suppository has the following composition:

| Component | Amount (mg) |
| --- | --- |
| Active Ingredient B | 150.0 |
| Polyethylene glycol 1500 | 550.0 |
| Polyethylene glycol 6000 | 460.0 |
| Polyethylene sorbitane monstearate | 840.0 |
| Total: | 2000.0 |

Preparation

After the suppository mass has been melted, the active ingredient is homogeneously distributed therein, and the melt is poured into chilled molds.

EXAMPLE 401

Suspension Containing 10 mg/ml of Active Ingredient B

| Component | Amount |
| --- | --- |
| Active Ingredient B | 1.0 gm |
| Sodium salt of carboxymethyl cellulose | 0.1 gm |
| Methyl p-hydroxybenzoate | 0.05 gm |
| Propyl p-hydroxybenzoate | 0.01 gm |
| Sucrose | 10.0 gm |
| Glycerin | 5.0 gm |
| 70% Sorbitol solution | 20.0 gm |
| Flavoring | 0.3 gm |
| Distilled water q.s. ad | 100.0 ml |

Preparation

Distilled water is heated to 70° C. The methyl and propyl p-hydroxybenzoates, the glycerin, and the sodium salt of carboxymethyl cellulose are dissolved therein under stirring. The solution is cooled to ambient temperature, and the active ingredient is added and homogeneously dispersed with stirring. After the sugar, sorbitol solution, and flavoring have been added and dissolved, the suspension is evacuated under stirring to eliminate air. Five milliliters of suspension contain 50 mg of active ingredient.

EXAMPLE 402

Tablet containing 150 mg of Active Ingredient B

Each tablet has the following composition:

| Component | Amount (mg) |
| --- | --- |
| Active Ingredient B | 150.0 |
| Powdered lactose | 89.0 |
| Corn starch | 40.0 |
| Colloidal silicic acid | 10.0 |
| Polyvinylpyrrolidone | 10.0 |
| Magnesium stearate | 1.0 |
| Total: | 300.0 |

Preparation

Active ingredient mixed with the lactose, corn starch, and silicic acid is moistened with a 20% aqueous polyvinylpyrrolidone solution and passed through a screen with a mesh size of 1.5 mm. The granulate, dried at 45° C., is passed through the same screen again and mixed with the specified quantity of magnesium stearate. Tablets are compressed from the mixture.
Weight of tablet: 300 mg
Punch: 10 mm, flat.

EXAMPLE 403

Coated Tablets Containing 75 mg of Active Ingredient B

Each tablet core has the following composition:

| Component | Amount (mg) |
| --- | --- |
| Active Ingredient B | 75.0 |
| Calcium phosphate | 93.0 |
| Corn starch | 35.5 |
| Polyvinylpyrrolidone | 10.0 |
| Hydroxypropylmethyl cellulose | 15.0 |
| Magnesium stearate | 1.5 |
| Total: | 230.0 |

Preparation

The active ingredient is mixed with calcium phosphate, corn starch, polyvinylpyrrolidone, hydroxypropylmethyl cellulose, and half the specified quantity of magnesium stearate. Compressed tablets with a diameter of about 13 mm are produced in a tablet-making machine, passed through a screen with a mesh size of 1.5 mm by suitable means, and mixed with the remainder of the magnesium stearate. This granulate is compressed, in a tablet-making machine, to form tablets of the desired shape.
Weight of core: 230 mg
Punch: 9 mm, convex.

The tablet cores thus produced are coated with a film consisting essentially of hydroxypropylmethyl cellulose. The finished film-coated tablets are polished with beeswax.
Weight of coated tablet: 245 mg.

While the present invention has been illustrated with the aid of certain specific embodiments thereof, it will be readily apparent to others skilled in the art that the invention is not limited to these particular embodiments, and that various changes and modifications may

We claim:

1. A compound of the formula

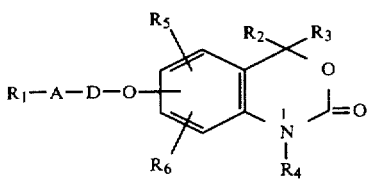

wherein

A is a sulfur atom or an SO, $SO_2$, R—N=S, or R—N=SO group where R is a hydrogen atom or a benzoyl or phenylsulfonyl group, optionally substituted by a methyl group, or an acetyl or propionyl group;

D is a linear or branched alkylene group having from 2 to 6 carbon atoms;

$R_1$ is an alkyl group having from 1 to 3 carbon atoms, optionally substituted by a phenyl group, or a phenyl group, each phenyl group being optionally substituted by an alkyl group having from 1 to 4 carbon atoms, a halogen atom, an alkoxy group having from 1 to 3 carbon atoms, a hydroxyl group, a cyclohexyl group, a phenyl group, an amino group, or an alkanoylamino group having from 1 to 3 carbon atoms; an alkyl group having from 4 to 8 carbon atoms; a cycloalkyl group having from 3 to 7 carbon atoms; a di-substituted or tri-substituted phenyl group of a mono-substituted or di-substituted hydroxyphenyl or aminophenyl group, the substituents, which may be the same or different, being selected from the group consisting of alkyl groups having from 1 to 4 carbon atoms, alkoxy groups having from 1 to 3 carbon atoms, and halogen atoms; a pyridyl-N-oxide group; or a 5-membered or 6-membered aromatic ring, optionally substituted by one or two alkyl groups each having from 1 to 3 carbon atoms, the aromatic ring containing from 1 to 3 nitrogen atoms or 1 nitrogen atom and 1 sulfur atom, while a phenyl group may optionally be fused onto the aromatic ring via two adjacent carbon atoms;

$R_2$ and $R_3$, which may be identical or different, are each a hydrogen atom, phenyl group, alkyl group having from 1 to 6 carbon atoms, or cycloalkyl group having from 3 to 7 carbon atoms;

$R_4$ is a hydrogen atom or an alkyl group having from 1 to 3 carbon atoms;

$R_5$ is a hydrogen or halogen atom, a nitro group, or an alkyl group having from 1 to 3 carbon atoms; and $R_6$ is a hydrogen or halogen atom or an alkyl group having from 1 to 3 carbon atoms.

2. A compound of claim 1, wherein

A is as defined in claim 1;

D is a linear alkylene group having from 2 to 6 carbon atoms;

$R_1$ is an alkyl group having from 1 to 8 carbon atoms; a cyclohexyl, benzyl, pyridyl, pyridyl-N-oxide, 2-benzothiazolyl, or 1,2,4-triazol-3-yl group; a 2-pyrimidinyl group optionally substituted by one or two methyl groups; a phenyl group optionally substituted by an alkyl group having from 1 to 4 carbon atoms, by a hydroxyl, methoxy, cyclohexyl, phenyl, or acetylamino group, or by a fluorine, chlorine, or bromine atom; a phenyl group di-substituted by chlorine or bromine atoms or by methyl or methoxy groups, where the substituents of the phenyl nucleus may be identical or different; or an aminophenyl or hydroxyphenyl group substituted by two alkyl groups, each having from 1 to 4 carbon atoms, or by two chlorine or bromine atoms;

$R_2$ and $R_3$, which may be the same or different, are each a hydrogen atom, an alkyl group having from 1 to 6 carbon atoms, or a phenyl or cyclohexyl group;

$R_4$ is a hydrogen atom or a methyl group;

$R_5$ is a hydrogen, fluorine, chlorine, or bromine atom or a nitro, methyl, or ethyl group; and $R_6$ is a hydrogen, chlorine, or bromine atom or a methyl or ethyl group.

3. A compound of claim 2 of the formula

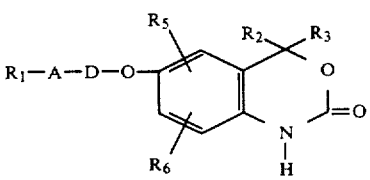

wherein A, D, $R_1$ to $R_3$, $R_5$, and $R_6$ are as defined in claim 2.

4. A compound of claim 3, wherein

A is an SO, $SO_2$, H—N=SO, $CH_3CO$—N=S, or $CH_3$—$C_6H_4SO_2N\alpha SO$ group;

D is an n-butylene group;

$R_1$ is a phenyl group optionally substituted by a fluorine, chlorine, or bromine atom or a methyl, hydroxyl, methoxy, cyclohexyl, phenyl, or acetamino group; a phenyl group di-substituted by chlorine or bromine atoms or by methyl or methoxy groups, the substituents of the phenyl nucleus being the same or different; or a f4-amino-3,5-dibromophenyl, 3,5-di-tert.butyl-4-hydroxyphenyl, or pyridyl group;

$R_2$ and $R_3$, which may be the same or different, each are a hydrogen atom or a methyl group;

$R_5$ is a hydrogen, chlorine, or bromine atom or a nitro or methyl group; and $R_6$ is a hydrogen, chlorine, or bromine atom or a methyl group.

5. A compound of claim 3, wherein

A is an SO, HN=SO, or $CH_3CO$—N=SO group;

D is an n-butylene group;

$R_1$ is a phenyl group, optionally substituted in the 4-position by a fluorine, chlorine, or bromine atom or by a methyl, cyclohexyl, phenyl, hydroxyl, or methoxy group, or a 3-methoxyphenyl, 3,4-dichlorophenyl, 3,4-dimethoxyphenyl, 4-bromo-3-methyl-phenyl, 4-amino-3,5-dibromo-phenyl, or 4-hydroxy-3,5-di-tert.butyl-phenyl group;

$R_2$ and $R_3$ are each a hydrogen atom or a methyl group;

$R_5$ is a hydrogen atom or, in the 7-position, a chlorine or bromine atom; and $R_6$ is a hydrogen atom.

6. 6-[4-(4-Biphenylylsulfinyl)-butoxy]-4,4-dimethyl-4H-3,1-benzoxazin-2-one.

7. 6-[4-(4-Bromo-phenylsulfinyl)-butoxy]-4,4-dimethyl-4H-3,1-benzoxazin-2-one.

8. A pharmaceutical composition for the prophylaxis or treatment of thrombo-embolic diseases, for the treatment of arteriosclerosis, or for the prophylaxis of metastasis which consists essentially of one or more inert pharmaceutical carriers and/or diluents and an effective amount of a compound of claim 1.

9. A pharmaceutical composition for the prophylaxis or treatment of thrombo-embolic diseases, for the treatment of arteriosclerosis, or for the prophylaxis of metastasis which consists essentially of one or more inert pharmaceutical carriers and/or diluents and an effective amount of the compound of claim 6.

10. A pharmaceutical composition for the prophylaxis or treatment of thrombo-embolic diseases, for the treatment of arteriosclerosis, or for the prophylaxis of metastasis which consists essentially of one or more inert pharmaceutical carriers and/or diluents and an effective amount of the compound of claim 7.

11. A method for the prophylaxis or treatment of thrombo-embolic diseases, for the treatment of arteriosclerosis, or for the prophylaxis of metastasis in a warm-blooded animal or human in need of such treatment which comprises perorally, parenterally, or rectally administering to said animal or human an effective amount of a compound of claim 1.

12. A method for the prophylaxis or treatment of thrombo-embolic diseases, for the treatment of arteriosclerosis, or for the prophylaxis of metastasis in a warm-blooded animal or human in need of such treatment which comprises perorally, parenterally, or rectally administering to said animal or human an effective amount of the compound of claim 10.

13. A method for the prophylaxis or treatment of thrombo-embolic diseases, for the treatment of arteriosclerosis, or for the prophylaxis of metastasis in a warm-blooded animal or human in need of such treatment which comprises perorally, parenterally, or rectally administering to said animal or human an effective amount of the compound of claim 7.

* * * * *

UNITED STATES PATENT AND TRADEMARK OFFICE
CERTIFICATE OF CORRECTION

PATENT NO. : 4,518,597

DATED : May 21, 1985

INVENTOR(S) : BERTHOLD NARR et al.

It is certified that error appears in the above-identified patent and that said Letters Patent is hereby corrected as shown below:

Column 36, line 22, the moiety "6-[4-tert.Butyl-" should read:
— 6-[4-(4-tert.Butyl- —.

Column 49, line 24, the moiety "-4,4-dimethyl-B" should read:
— -4,4-dimethyl- —.

Claim 4, line 3, "$CH_3-C_6H_4SO_2NaSO$" should read: — $CH_3-C_6H_4SO_2N=SO$ —.

Claim 4, line 11, the moiety "f4-amino-" should read — 4-amino- —.

Signed and Sealed this

Twentieth Day of May 1986

[SEAL]

Attest:

DONALD J. QUIGG

Attesting Officer

Commissioner of Patents and Trademarks